United States Patent [19]
Aggarwal

[11] Patent Number: 5,993,798
[45] Date of Patent: *Nov. 30, 1999

[54] ONCOINHIBIN AND METHODS OF PHARMACEUTICAL USE

[75] Inventor: Bharat B. Aggarwal, Houston, Tex.

[73] Assignee: Research Development Foundation, Carson City, Nev.

[ * ] Notice: This patent is subject to a terminal disclaimer.

[21] Appl. No.: 08/283,794

[22] Filed: Aug. 1, 1994

Related U.S. Application Data

[60] Continuation-in-part of application No. 08/010,087, Jan. 27, 1993, abandoned, which is a division of application No. 07/874,308, Apr. 24, 1992, Pat. No. 5,241,051.

[51] Int. Cl.$^6$ ............................ A61K 38/19; C07K 14/52
[52] U.S. Cl. ............................................ 424/85.1; 530/351
[58] Field of Search ................................. 530/351; 514/2

[56] References Cited

U.S. PATENT DOCUMENTS 5,241,051   8/1993   Aggarwal ................................ 530/351

*Primary Examiner*—Vasu S. Jagannathan
*Assistant Examiner*—K. Cochrane Carlson
*Attorney, Agent, or Firm*—Benjamin Aaron Adler

[57] ABSTRACT

The present invention provides a novel human cytokine termed Oncoinhibin. The protein Oncoinhibin is secreted by human erythroblastoid cells, has a molecular weight of approximately 28 kDa and exerts diverse neoplastic activity. The present invention also provides a method for treating neoplastic cells using human Oncoinhibin and a pharmaceutical composition comprised essentially of Oncoinhibin.

6 Claims, 47 Drawing Sheets

ONCOINHIBIN AND METHODS OF PHARMACEUTICAL USE

CROSS-REFERENCE TO RELATED APPLICATION

This application is a continuation in part of U.S. Ser. No. 08/010,087, filed Jan. 27, 1993, now abandoned, which is a divisional of U.S. Ser. No. 07/874,308, filed Apr. 24, 1992 now U.S. Pat. No. 5,241,051.

BACKGROUND OF THE INVENTION

1. Field of the Invention

The present invention relates generally to cytokines. More specifically, the present invention relates to a novel cytokine with broad anti-neoplastic activity.

2. Description of the Related Art

Cell growth appears to be regulated by a balance between growth stimulatory and growth inhibitory molecules. An imbalance in these growth regulatory cytokines has been proposed as one of the mechanisms of tumor growth.

Several cytokines which stimulate the growth of tumor and normal cells have been described. These include, e.g., epidermal growth factor (EGF), fibroblast growth factor (FGF), platelet derived growth factor (PDGF), insulin-like growth factors (IGF), interleukins (IL), colony stimulating factors (CSF) and transforming growth factors (TGF-α and TGF-β).

In contrast, other cytokines selectively inhibit the growth of certain tumor cells. These include, e.g., interferons (IFN), lymphotoxin (LT), tumor necrosis factor (TNF), oncostatin M, amphiregulin, interleukin-1 (IL-1), interleukin-6 (IL-6) and TGF-β.

These growth stimulatory and growth inhibitory cytokines can be differentiated from each other based on their source, their specificity against tumor targets, their physiochemical properties and their primary structure. Thus, the identification and characterization of growth regulatory cytokines is of critical importance in the understanding of cellular growth, including growth of neoplasms.

SUMMARY OF THE INVENTION

In one embodiment of the present invention, there is provided a novel composition of matter. This novel composition of matter, termed Oncoinhibin, is secreted by human erythroblastoid cells, has a molecular weight of approximately 28 kDa on SDA-PAGE and exhibits diverse anti-neoplastic activity.

In one embodiment the present invention provides a method for preparing a novel human cytokine termed Oncoinhibin. The method comprises incubating human erythroblastoid cells, inducing the production of Oncoinhibin and harvesting conditioned cell supernatants.

In yet another embodiment of the present invention, there is provided a method of purifying human Oncoinhibin. This method comprises the steps of ultrafiltering conditioned cells supernatants containing human Oncoinhibin. Subsequently in human Oncoinhibin and dialyzing the ultrafiltered supernatants. Subsequently DEAE Affigel blue chromatography, Sodium dodecyl Sulfate-polyacrylamide gel electrophoresis and reverse phase high performance liquid chromatography is performed to purify human Oncoinhibin.

In another embodiment of the present invention, there is provided a novel immunomodulator for activating lymphocytes, monocytes and neutrophils to kill tumor cells. The novel immunomodulator comprises human Oncoinhibin. Also provided is a novel growth factor for stimulating the growth of normal cells. This growth factor comprises human Oncoinhibin. In other embodiments of the present invention there are provided pharmaceutical compositions of Oncoinhibin and methods of treating a neoplastic cell comprising the administration of an effective dose of Oncoinhibin.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of this specification. It is to be noted, however, that the appended drawings illustrate preferred embodiments of the invention and therefore are not to be considered limiting of their scope. In the invention made of equally effective equivalent embodiments.

DETAILED DESCRIPTION OF THE INVENTION

Various cell lines including mouse connective tissue cell line L929 (CCL 1), K-562 (CCL-243), U-937 (CRL-1543), HL-60 (CCL-240), Raji (CCL-86), Jurkat (CRL-8163), BT 20 (HTB-1 9), MCF-7 (HTB-22), SK-BR-3 (HTB-30), ZR-75-1 (CRL-1500), RPMI 7951 (HTB-66), A375 (CRL-1619), A-431 (CRL-1555), ME-1 80 (HTB 83), OVCAR-3 (HTB-161), He La (CCL-2), Hep-2 (HB-8065), and NIH 3T3 (CRL-1618) were obtained from American Type Culture Collection, (Rockville, Md.). TNF-resistant NIH 3T3 cells were isolated as described by K. Totpal, R. LaPushin, H. N. Ananthaswamy and B. B. Aggarwal, *Lymphokine and Cytokine Res.* 10 (1991) 359–367. Cells were tested for mycoplasma contamination using the DNA-based assay kit purchased from Gen-Probe (San Diego, Calif.).

All cell cultures were maintained in continuous exponential growth by weekly passage. Some of the cells were subcultivated twice a week. Cells were routinely grown in RPMI 1640 medium supplemented with glutamine (2 mM), penicillin (100 units/ml), streptomycin (100 $\mu$g/ml), and fetal bovine serum (10%) in a humidified incubator in 5% $CO_2$ in air.

The conditioned supernatants of human erythroblastoid cell line K-562 produces an activity which is growth inhibitory to human breast tumor cell line MCF-7. Due to its ability to inhibit the growth of tumor cells and not that of normal cells, this activity is termed "Oncoinhibin".

For the production and induction of Oncoinhibin, human erythroblastoid cell line K-562 was grown in RPMI 1640 medium containing 10% fetal bovine serum supplemented with glutamine (2 mM), penicillin (100 units/ml), and streptomycin (100 $\mu$g/ml). Cells were harvested by centrifugation when a density of $0.8 \times 10^6$ cells/ml was reached, the cells were washed once with medium without serum and transferred to serum-free conditions in RPMI-1640 medium containing glutamine, penicillin and streptomycin. For production of Oncoinhibin, $1 \times 10^6$/ml of these cells were incubated for 48 hours in T175 flask (Falcon) under stationary culture conditions in RPMI 1640 medium without serum and then treated with phorbol ester (100 ng/ml) for 48 hours at 37° C. Thereafter, the conditioned cell supernatants were harvested by centrifugation, filtered through 0.22 micron filter (Falcon) and stored at 4° C. until further characterization. In order to concentrate the Oncoinhibin conditioned media from K-562 cell lines was ultrafiltered by PM-10 membrane (Amicon Corp.) and then dialyzed with 20 mM Tris, pH 8.0.

Figure 1A:
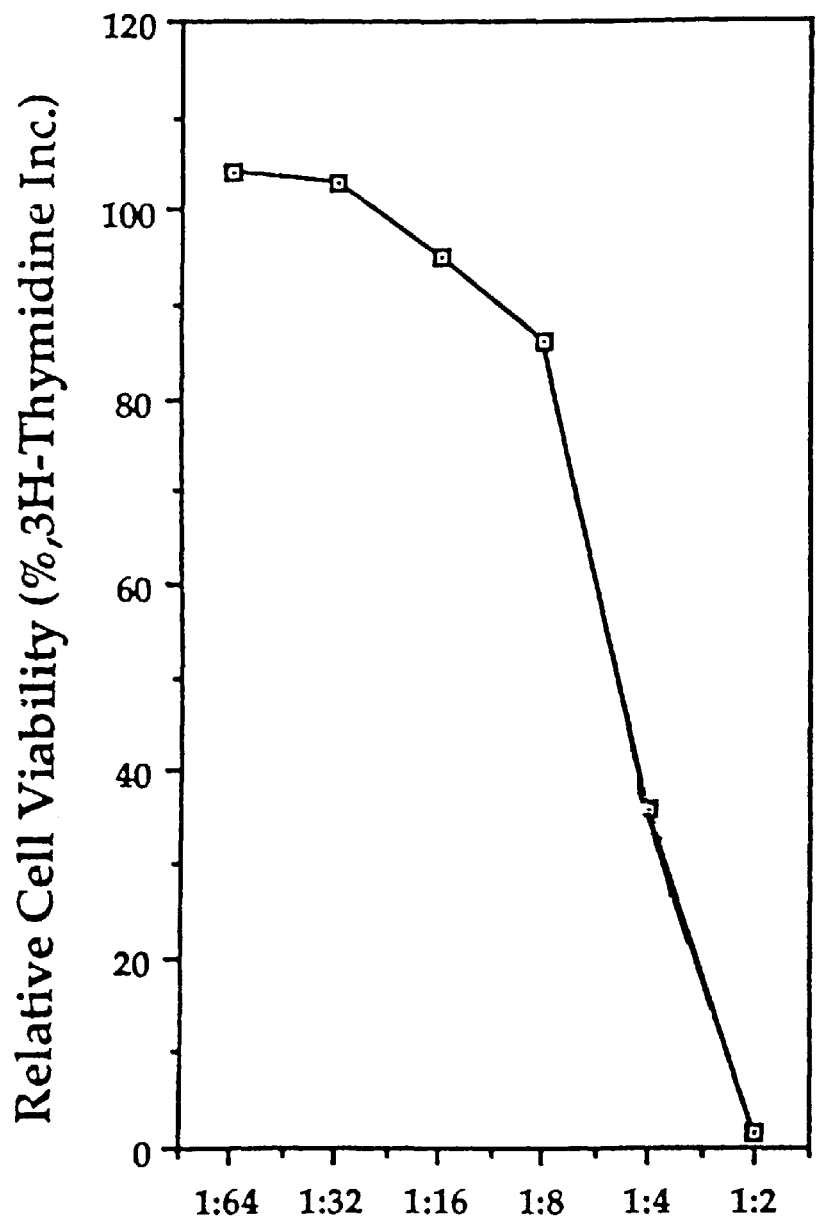
FIGS. 1A–1C illustrates that K-562 cell conditioned supernatants inhibit the growth of MCF-7 cells.
Figure 1B:
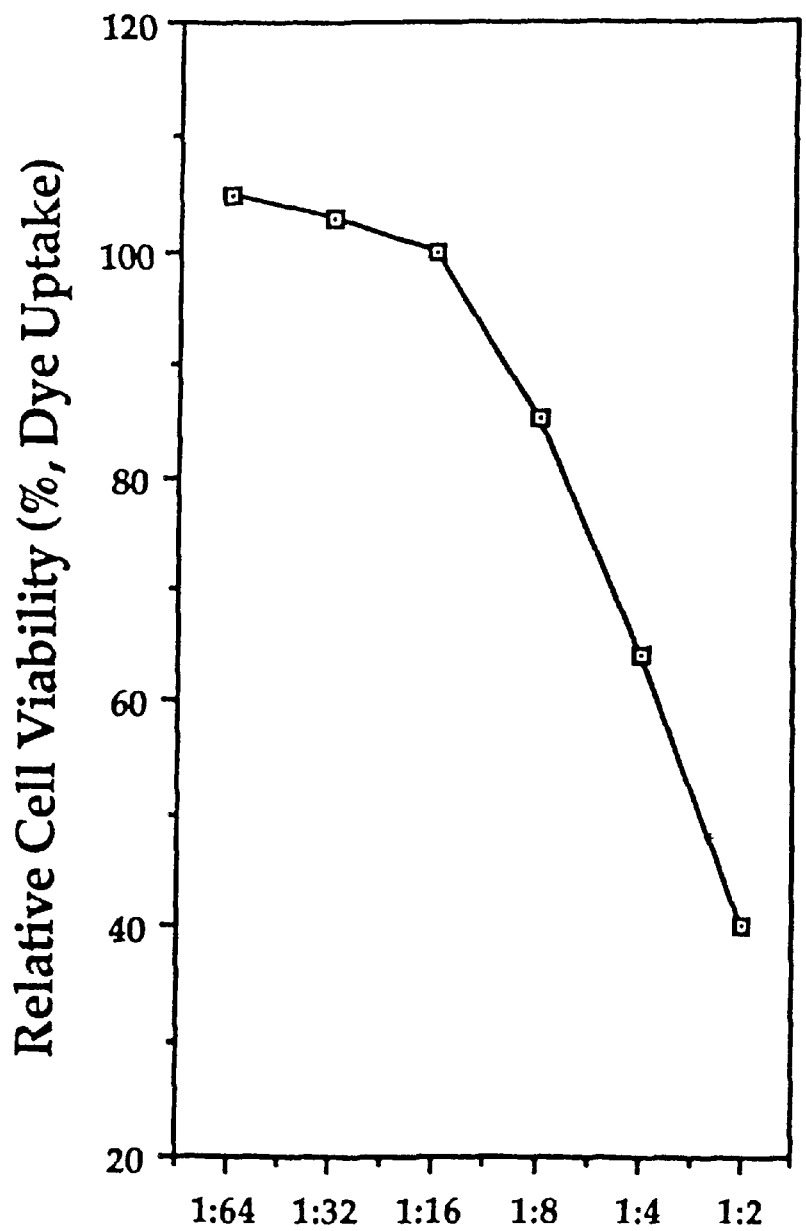
Figure 1C:
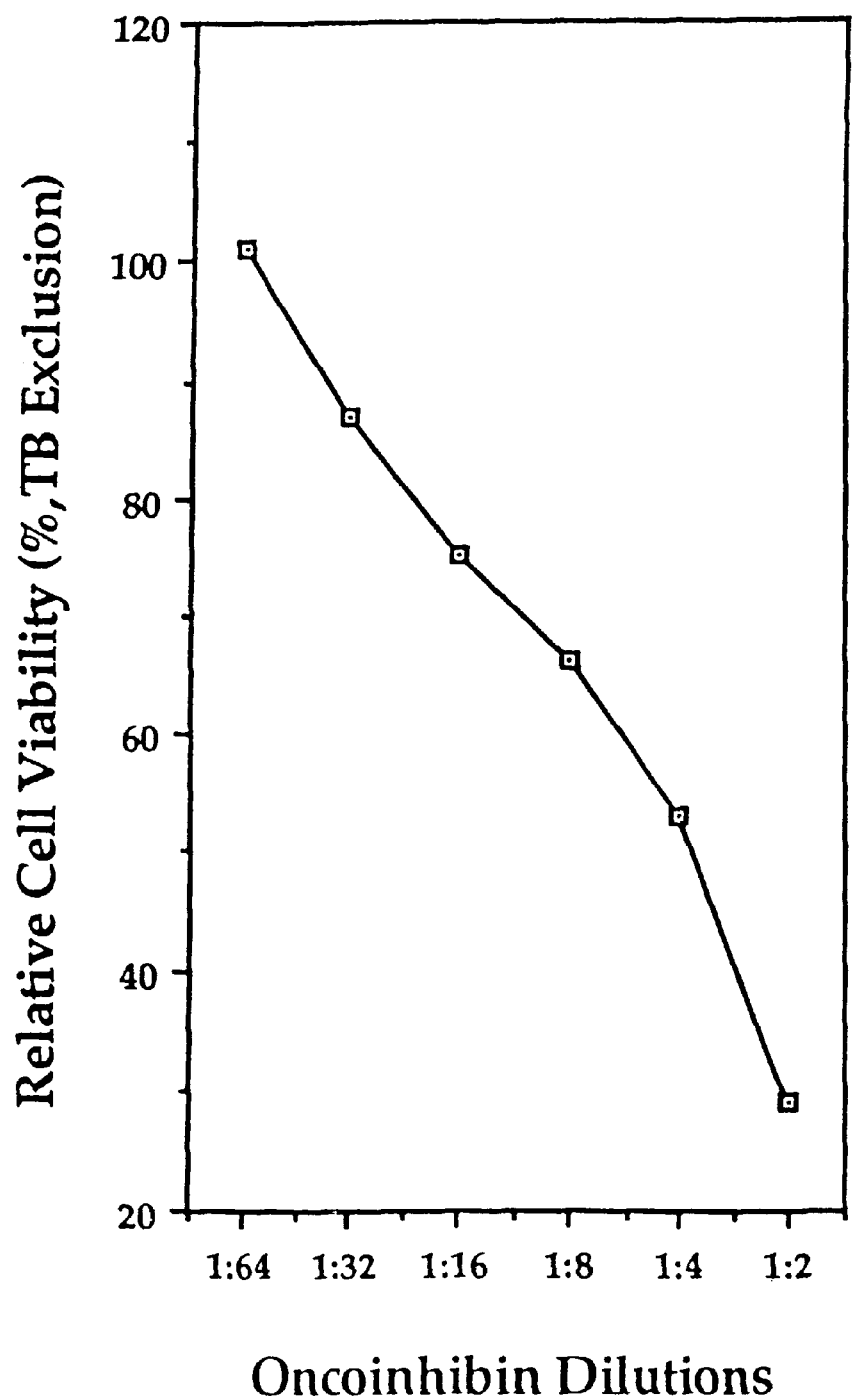

With reference to FIG. 1, inhibitory activity of Oncoinhibin on tumor cell growth was examined by three separate methods. These methods included (1) counting cells on hemocytometer after trypan blue staining; (2) crystal violet dye-uptake method; and (3) by tritiated thymidine incorporation method. Oncoinhibin clearly inhibits the growth of MCF-7 cells by all three methods in a dose dependent manner. Due to the convenience and sensitivity, MCF-7 cell line was used as a target to develop the bioassay for Oncoinhibin. The inhibition of tritiated thymidine incorporation by Oncoinhibin was found to be a highly sensitive method to detect this cytokine.

The bioassay for Oncoinhibin consists of plating $5 \times 10^3$ cells in 96 well flat bottom well plates in 0.1 ml of RPMI 1640 medium with 10% FCS overnight at 37° C. in a $CO_2$ incubator. Then the media is removed, a two-fold serial dilution of the test sample is added in a total final volume of 0.1 ml and incubation is continued for 24 hours at 37° C. During last 6 hours, tritiated thymidine (0.5 $\mu$Cl/0.05 mi/well) is added. At the end of 24 hours incubation period, media is poured-off and cells are detached with 0.1 ml of Trypsin (0.5%) and EDTA (5.3 mM) treatment for 30 minutes at 37° C. Cells are harvested by using PHD Cambridge cell harvester and cell-incorporated radioactivity is determined by beta counter. The data was expressed as % relative viability which is defined as amount of dpm taken up by cells in the presence of Oncoinhibin divided by the dpm incorporated in the presence of the media alone, multiplied by 100. The amount of Oncoinhibin required to inhibit the viability by 50% was defined as one unit of the cytokine. As is seen in FIG. 1, Oncoinhibin exerts a dose-dependent inhibition of tumor cell growth as illustrated by all three methods.

Figure 2:
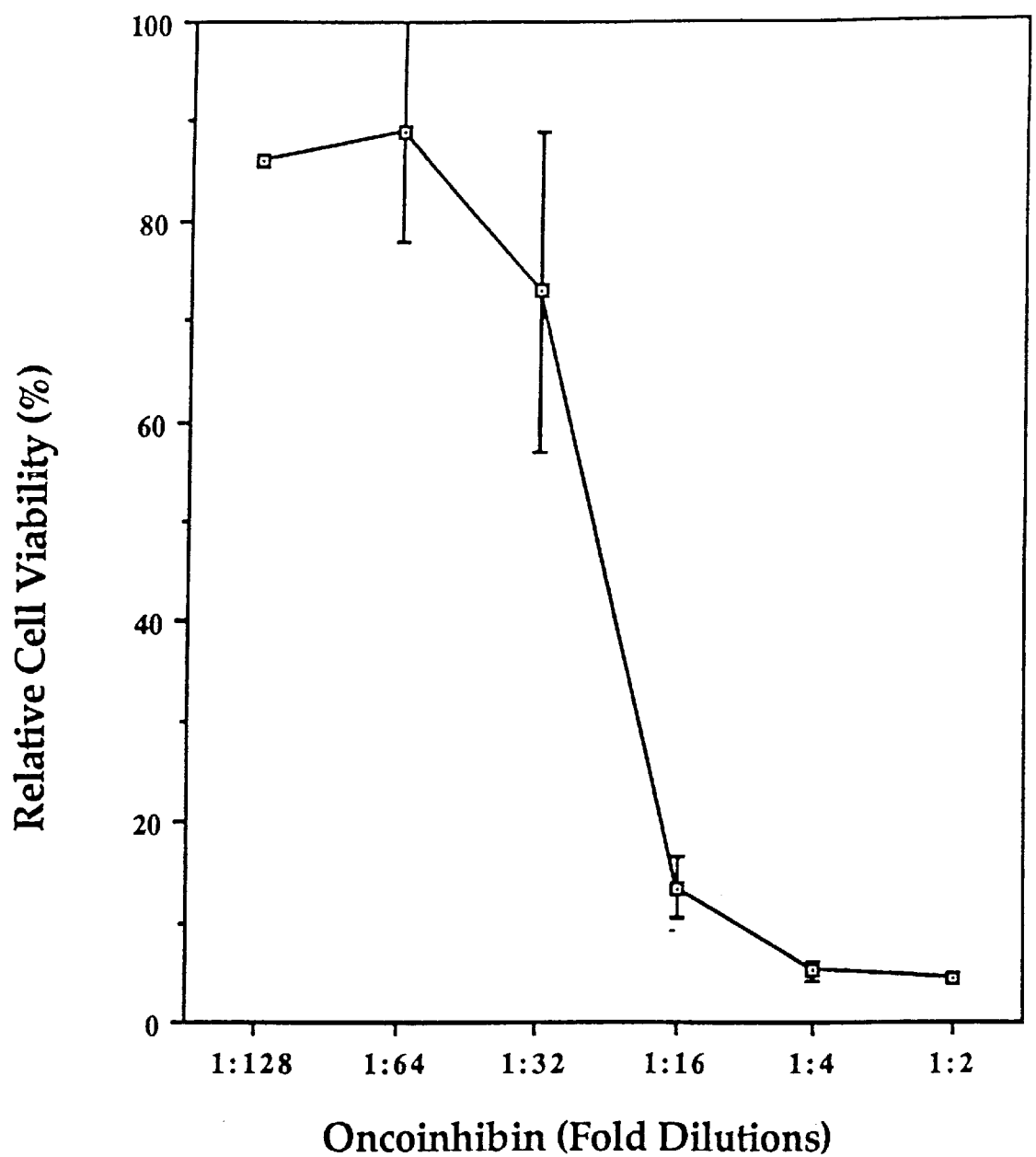
FIG. 2 depicts the standard bioassay for Oncoinhibin.

With reference to FIG. 2, a clear dose-dependent response by MCF-7 to Oncoinhibin could be observed within 24 hours. The reciprocal of the dilution of the sample needed to achieve 50% inhibition in thymidine incorporation was defined as one unit of Oncoinhibin.

Figure 3:
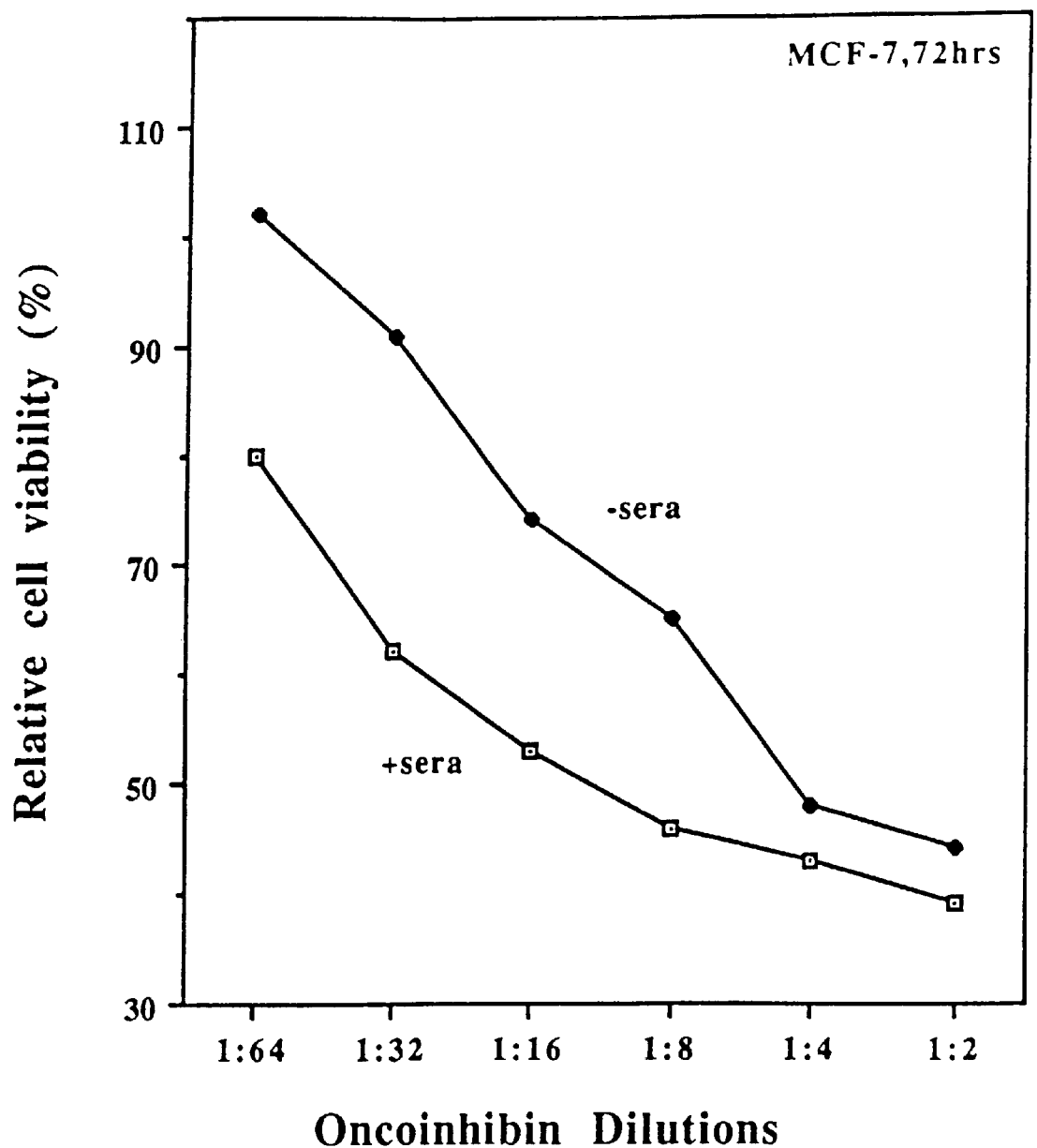
FIG. 3 shows the production of Oncoinhibin by K-562 cells in the presence and absence of serum.

With reference to FIG. 3, the production of Oncoinhibin under serum-free conditions was examined. Serum-free conditions were used due to the difficulty in purifying the proteins from samples containing serum. These results clearly indicate that the Oncoinhibin is secreted by K-562 cells even in the absence of serum.

Figure 4A:
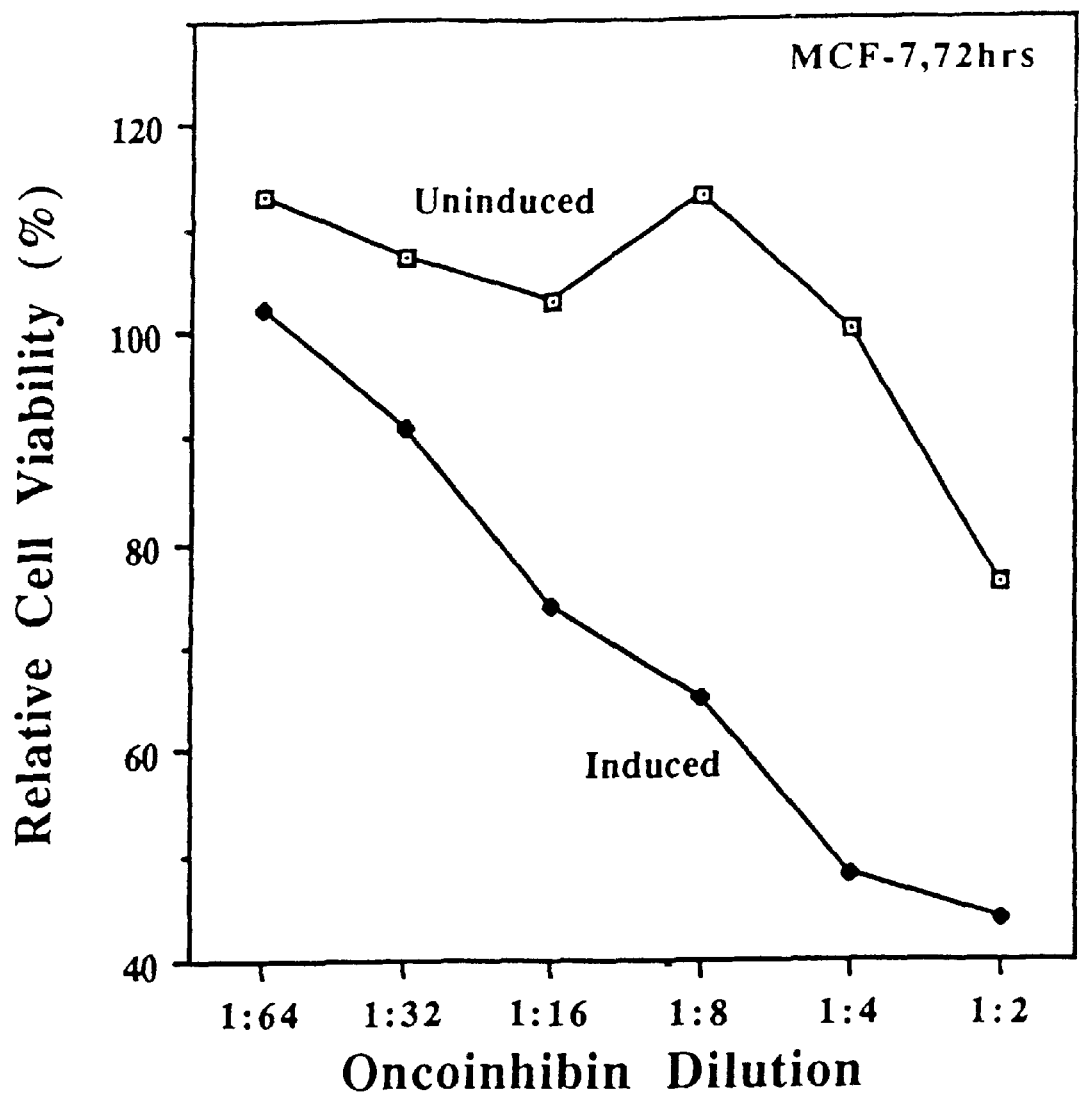
FIGS. 4A and 4B depict the effects of phorbol ester on the induction of Oncoinhibin.
Figure 4B:
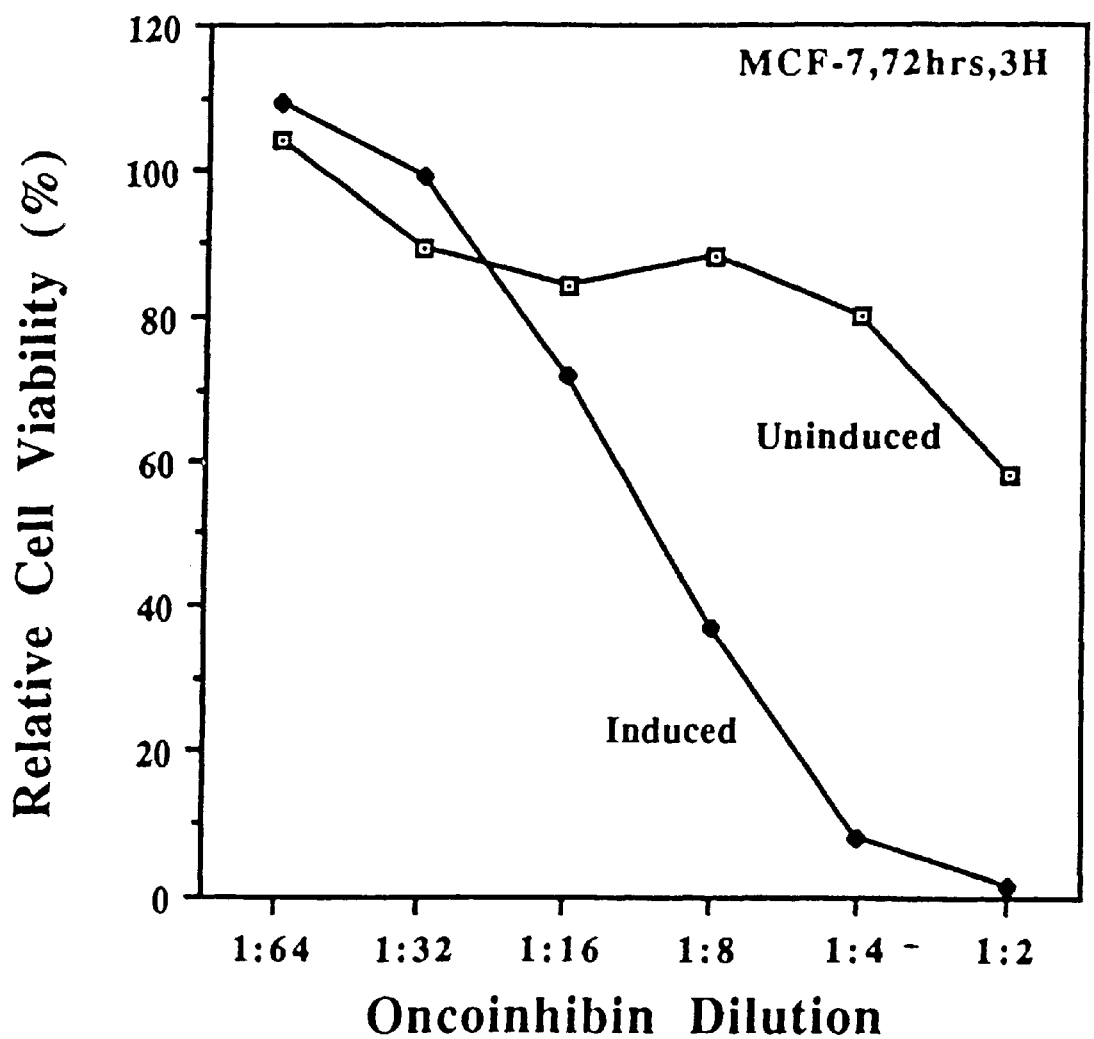

We examined whether different agents can induce production of Oncoinhibin. Calcium ionophore, Concanavalin A, Phytohemagglutinin, and phorbol ester were examined. FIG. 4 shows that phorbol ester can increase the production of Oncoinhibin. Thus, phorbal ester can be used to optimize the production of Oncoinhibin from K-562 cells. An approximately four fold increase in the production of Oncoinhibin was observed when cells were exposed to phorbol ester (100 ng/ml). Optimum induction of Oncoinhibin was observed when cells were incubated with phorbol ester for 48 hours (Table I) and at a cell-density of $1 \times 10^6$ cells per ml of the media (Table II).

TABLE I

Induction of Oncoinhibin from Human K-562 Cells by Phorbol Ester

| Time (hrs) | Uninduced | Induced |
|---|---|---|
| | Relative Cell Viability (%) | |
| 0 | 94 | — |
| 6 | 100 | 60 |
| 24 | 84 | 33 |
| 48 | 67 | 16 |
| 72 | 41 | 40 |

K-562 cells ($1 \times 10^6$/ml) were cultured in serum-free media (RPMI-1640) either in the presence or absence of the phorbol ester (100 ng/ml) at 37° C. in a $CO_2$ incubator for different times and then the conditioned media was harvested by centrifugation. Samples were tested on MCF-7 cells at 1:2 fold-serial dilutions as indicated in above.

TABLE II

Optimization of Production of Oncoinhibin in Presence and Absence of Phorbol Ester at Different Cell-Densities*

| Cell Number($\times 10^6$/ml) Relative Cell Viability (%) | Uninduced | Induced |
|---|---|---|
| 0.01 | 76 | 83 |
| 0.1 | 89 | 56 |
| 0.5 | 65 | 41 |
| 1.0 | 37 | 26 |
| 1.5 | 50 | 28 |

TABLE II-continued

Optimization of Production of Oncoinhibin in Presence and Absence of Phorbol Ester at Different Cell-Densities*

| Cell Number($\times 10^6$/ml) Relative Cell Viability (%) | Uninduced | Induced |
|---|---|---|

*K-562 cell were incubated at the indicated cell-density in serum-free media (RPMI-1640) for 72 hrs at 37° C. in a $CO_2$ incubator. The conditioned media was harvested by centrifugation and tested at two-fold serial dilution on MCF-7 cells as indicated above.

Figure 5:
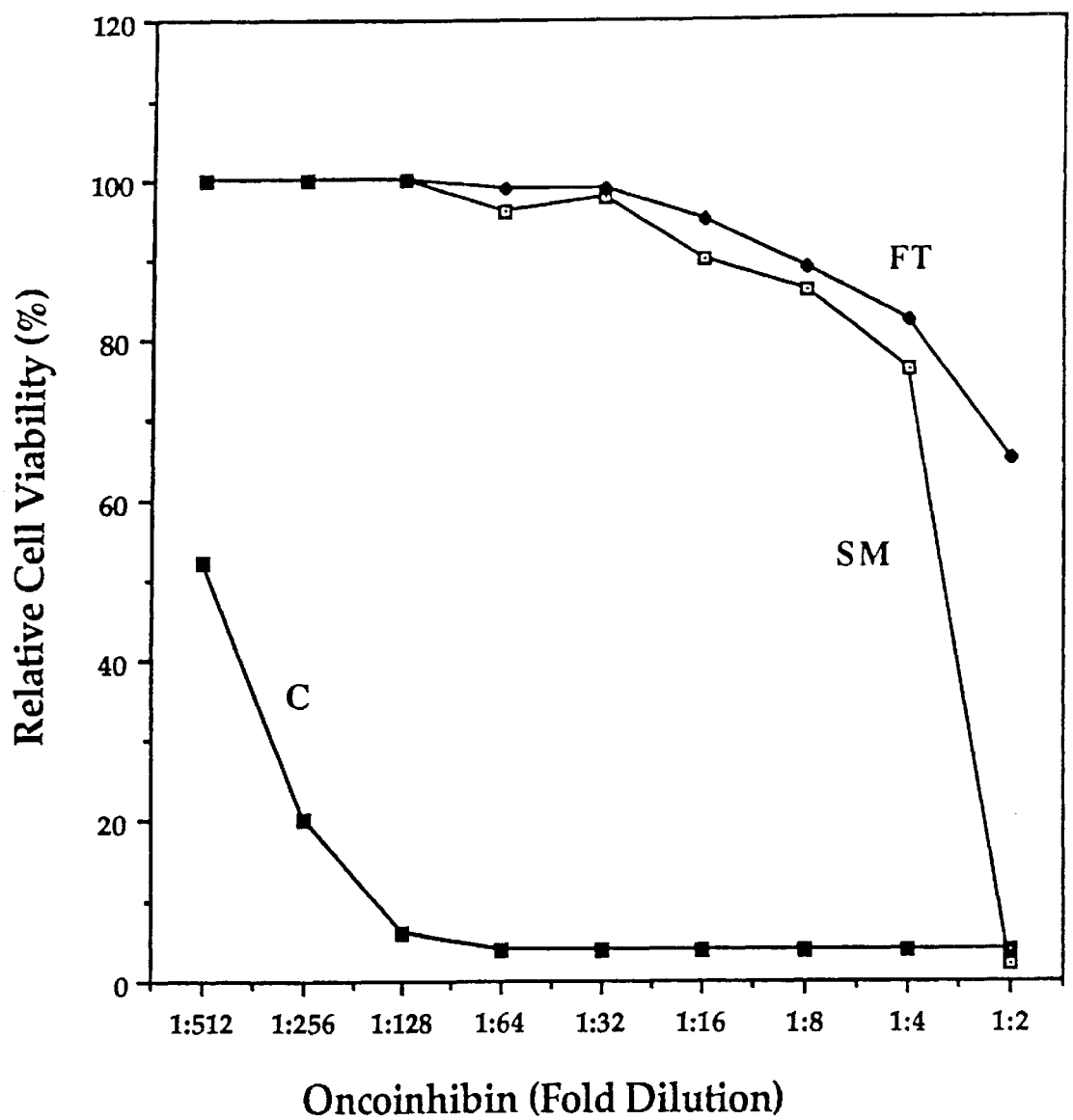
FIG. 5 shows the effects of ultrafiltration on Oncoinhibin activity.

With reference to FIG. 5, to purify and characterize Oncoinhibin, the cell conditioned media as concentrated by ultrafiltration using a 10,000 molecular weight cut-off (PM-10) membrane. The activity in the fraction not retained by the filter (Flow through or FT) was lower whereas that in the retained fraction or concentrate (C) was proportionately higher than that of the standard buffer (starting material, SM). The results indicate that Oncoinhibin activity is retained and concentrated. These results also indicate a molecular weight higher than 10,000 for Oncoinhibin.

Figure 6A:
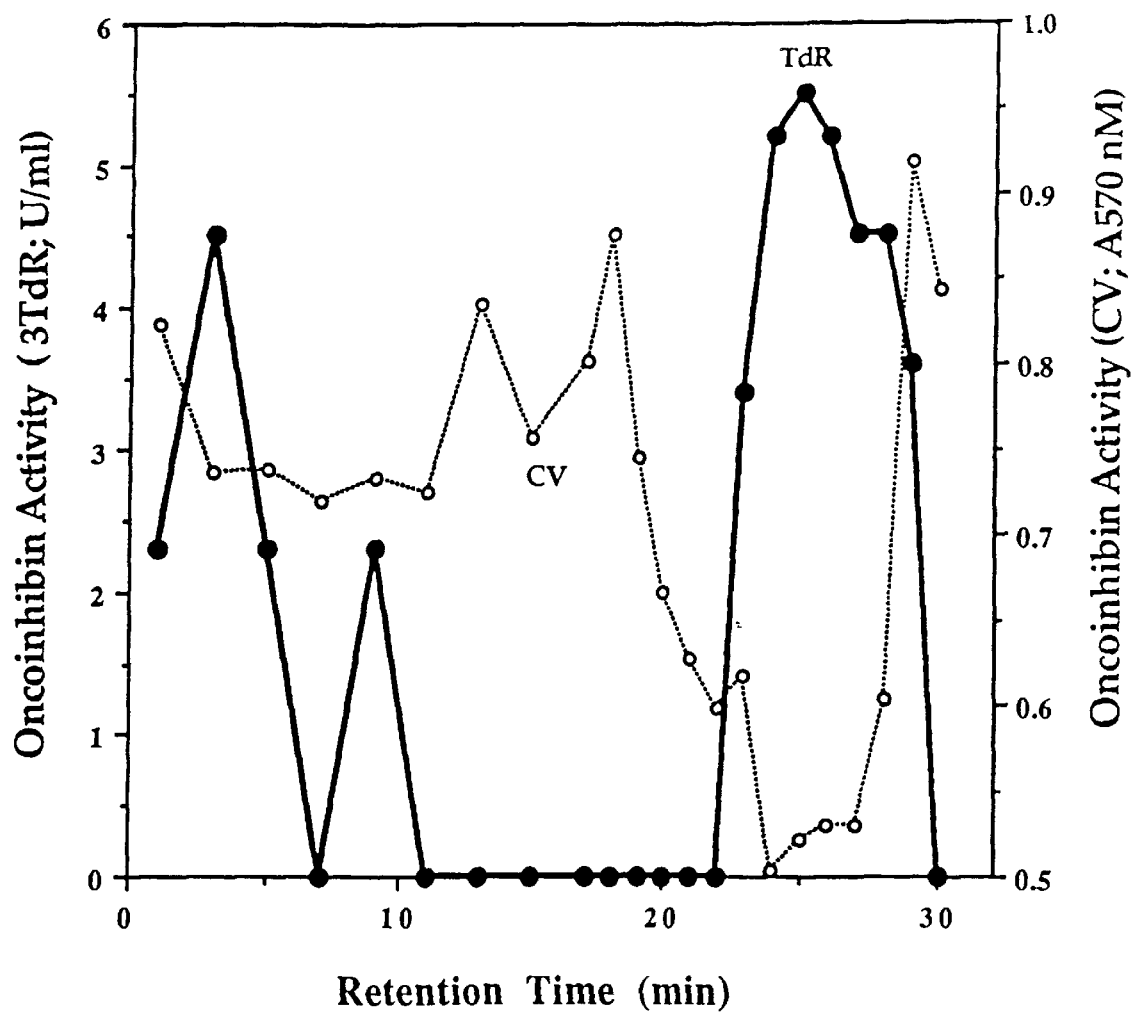
FIGS. 6A and 6B shows the characterization of Oncoinhibin by gel permeation chromatography.
Figure 6B:
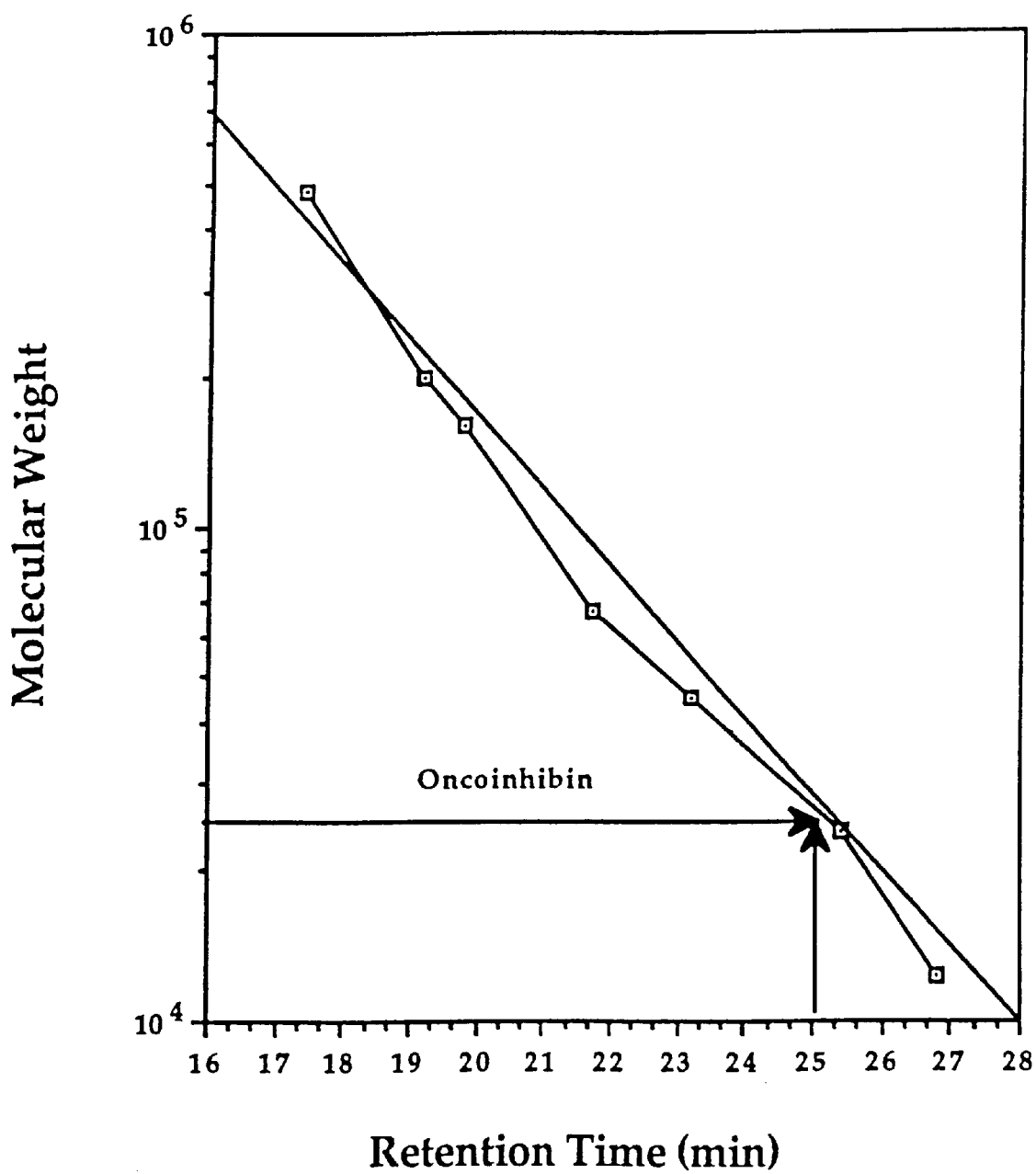

In the gel permeation fast protein liquid chromatographic experiment of FIGS. 6A and 6B, a sample of Oncoinhibin was applied onto a Superose-6 column (Pharmacia) pre-equilibrated with phosphate-buffered saline containing 0.1% bovine serum albumin and 0.01% sodium azide. The column was run at room temperature with a flow rate of 0.5 ml per minute and the size of each fraction was 0.5 ml. The column was calibrated with molecular weight standards (Schwarz/Mann, Cambridge, Mass.). The latter included Apoferritin (480 kDa), Alpha Amylase (20 kDa), Gamma-Globulin (160 kDa), Bovine Serum Albumin (67 kDa), Ovalalbumin (45 kDa), Chymotrypsinogen (24 kDa) and Cytochrome C (12.4 kDa).

With reference to FIG. 6, it appears that Oncoinhibin has an approximate molecular weight of 25 kDa. The molecular weight of Oncoinhibin was examined by gel permeation Fast Protein Liquid Chromatography on Superose-6 column under nondenaturing conditions. The results of gel filtration run in phosphate buffered saline, pH 7.4 show two major peaks of activity, one coinciding with the excluded volume and the second peak corresponding to an approximate molecular weight of around 25 kDa (FIG. 6B).

Figure 7:
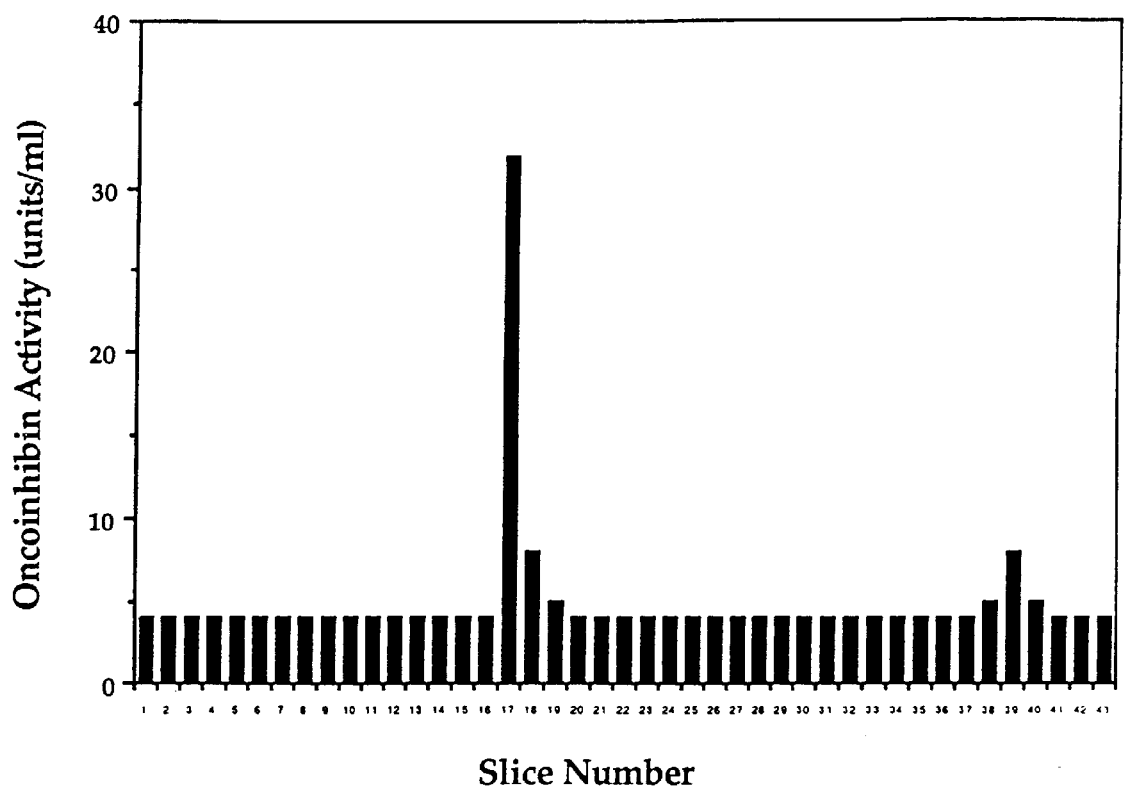
FIG. 7 shows the elution of Oncoinhibin activity from SDS polyacrylamide gel electrophoresis.
Figure 8:
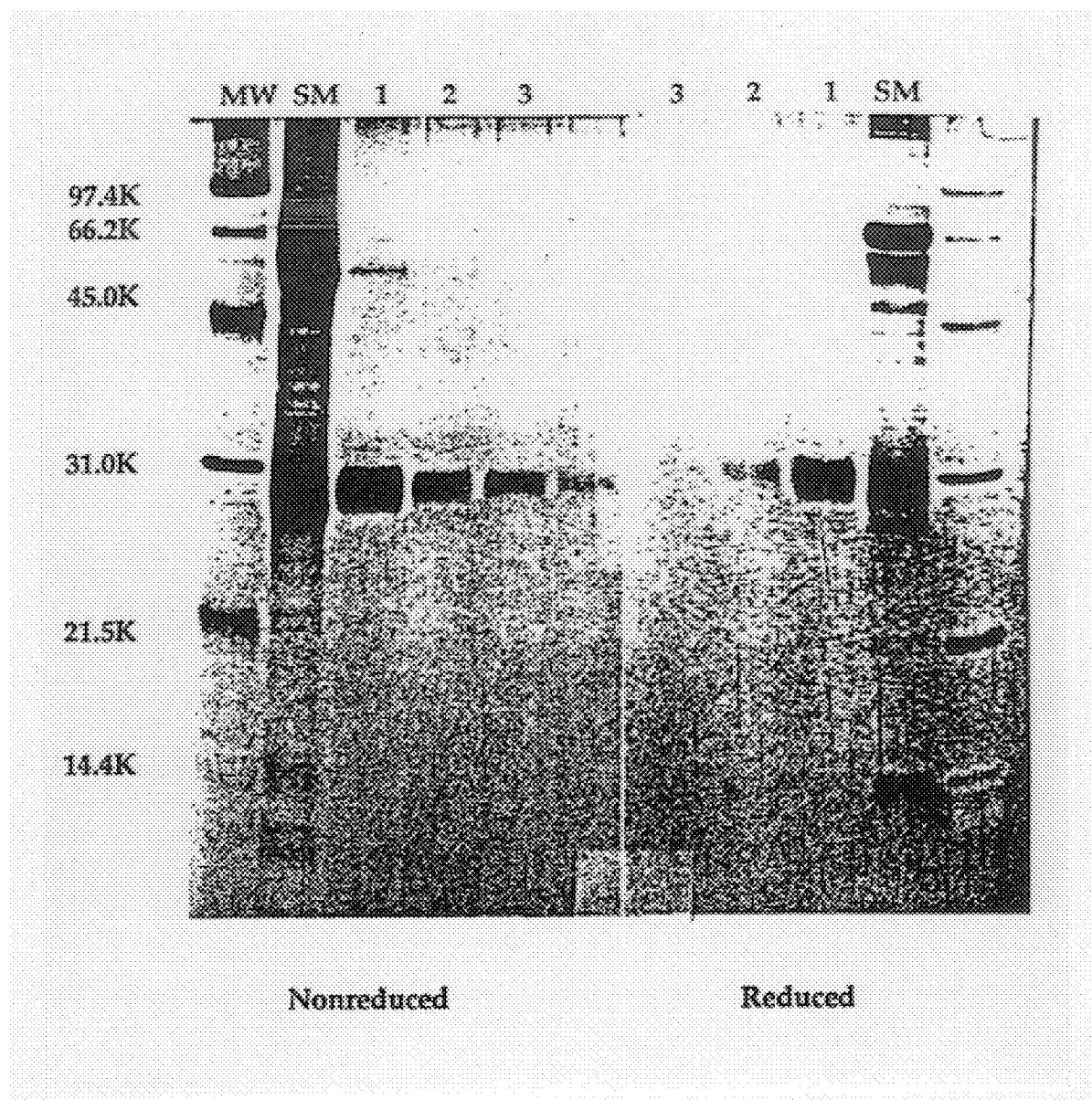
FIG. 8 depicts the SDS-PAGE analysis of Oncoinhibin.

In the sodium dodecyl sulfate polyacrylamide gel electrophoresis (SDS-PAGE) experiments of FIGS. 7 and 8, a 15% polyacrylamide gel was run essentially according to U. K. Laemmli (Nature 227 (1970) 680–685, incorporated by reference herein) and proteins were visualized by silver staining. For preparative gel electrophoresis and elution of activity, a portion of the gel before fixing and staining was sliced with a razor blade into over 40 different slices, eluted in a test tube with 50 mM ammonium bicarbonate by diffusion overnight, the fractions were dialyzed against 20 mM Tris, pH 8.0 and then assayed for biological activity.

With reference to FIG. 7, to further confirm the molecular weight of Oncoinhibin, SDS-PAGE analysis was performed. After electrophoresis, the gels were sliced, eluted in 50 mM ammonium bicarbonate overnight and assayed for Oncoinhibin activity. Greater than 50% of the applied Oncoinhibin activity was recovered in the molecular weight region of around 30 kDa. Less than 10% activity was also found in an area near the dye front.

With reference to FIG. 8, a rerun of the biologically active fraction on SDS-PAGE and silver staining of gels showed a single major band at a molecular weight of around 28 kDa.

Figure 9A:
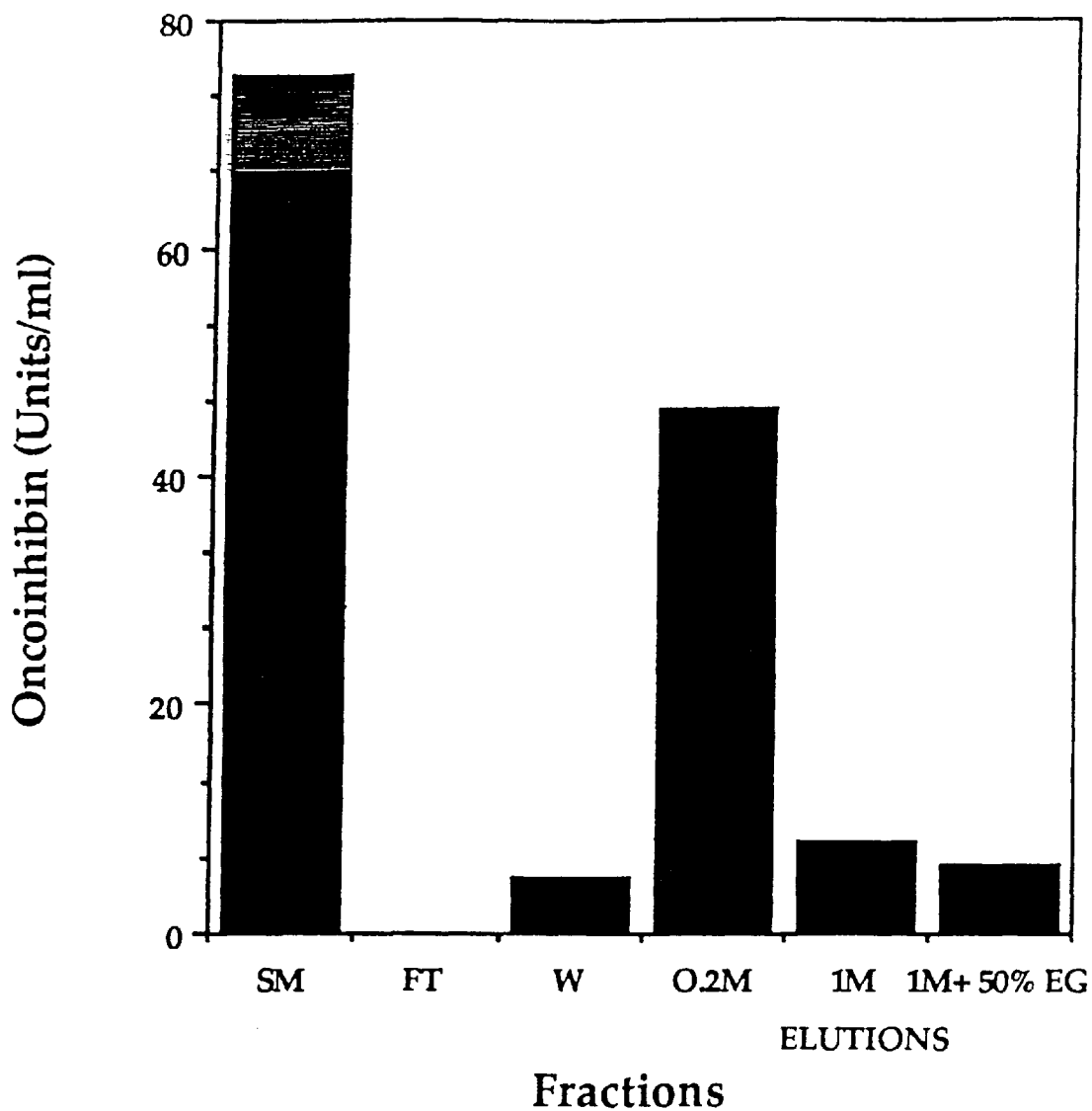
FIGS. 9A and 9B show the binding elution of Oncoinhibin activity from DEAE Affigel blue (upper panel) and from a Q-sepharose column (lower panel).
Figure 9B:
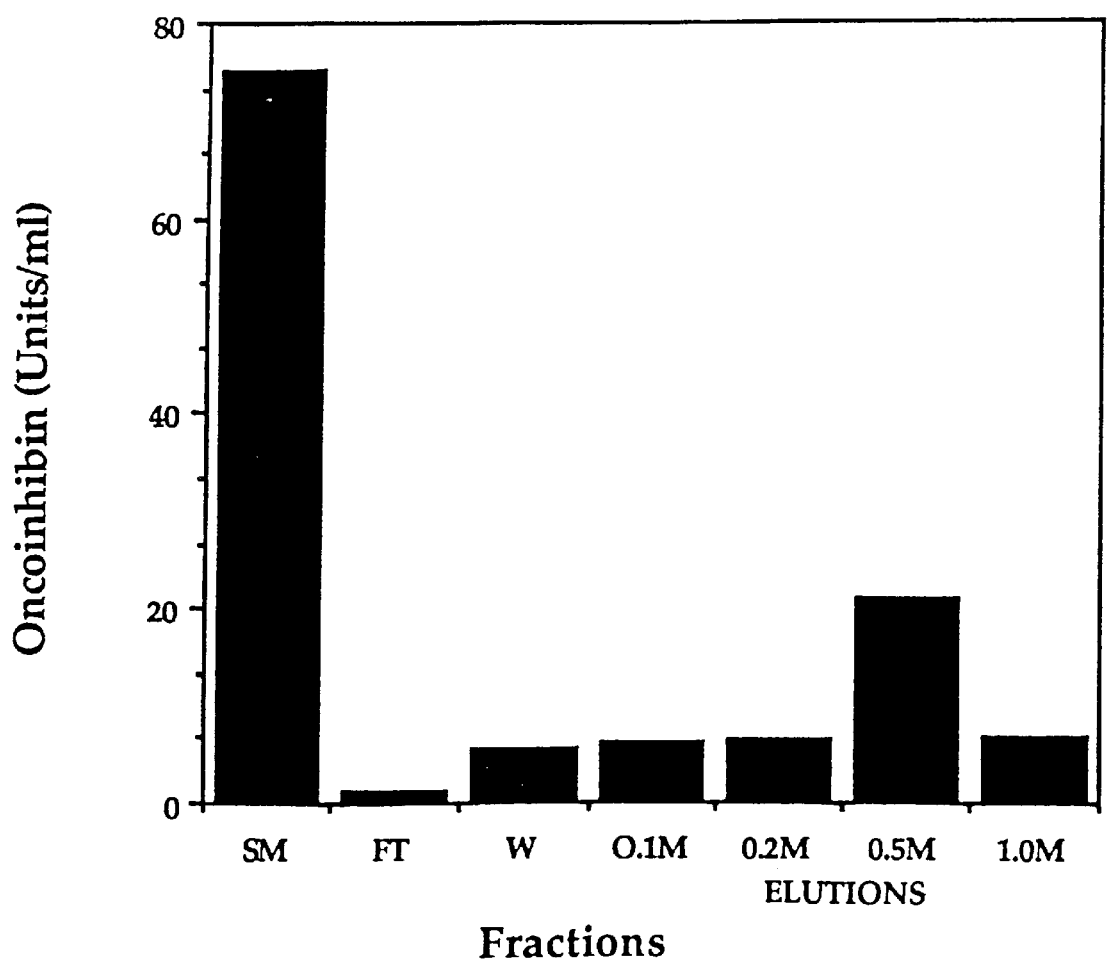
Figure 10B:
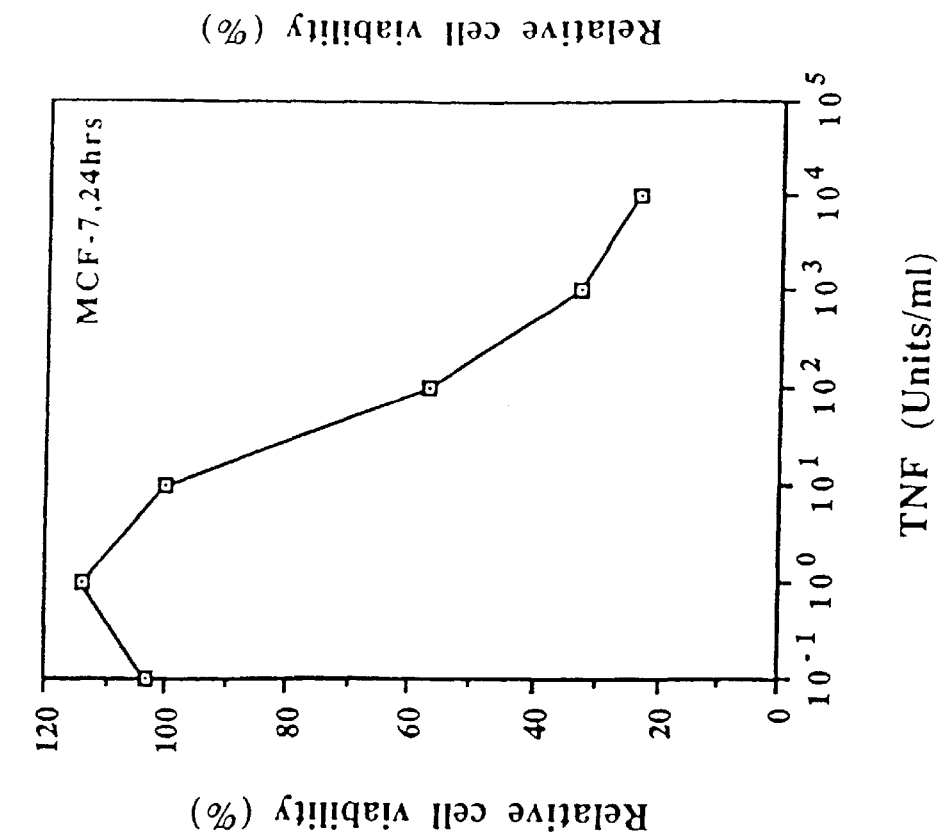
FIGS. 10A–10P illustrate the dose dependent antiproliferative effects of Oncoinhibin and TNF.
Figure 10A:
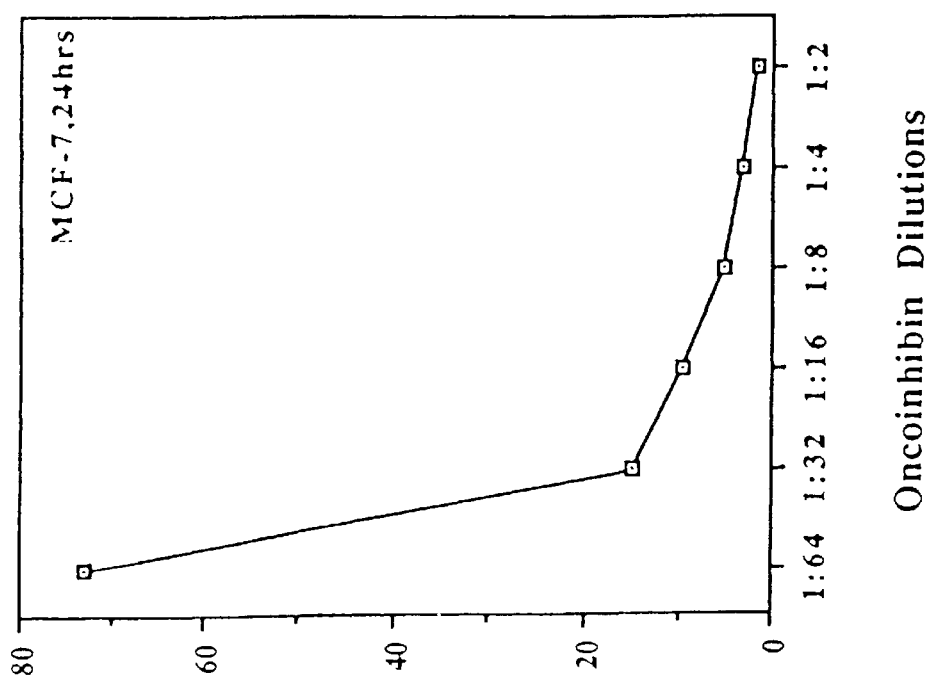
Figure 10D:
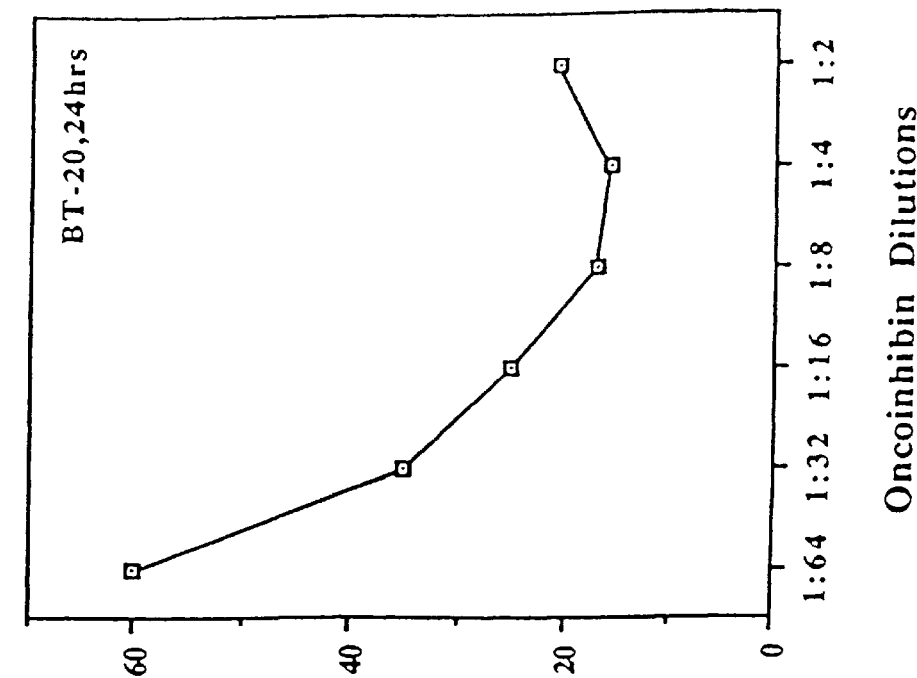
Figure 10C:
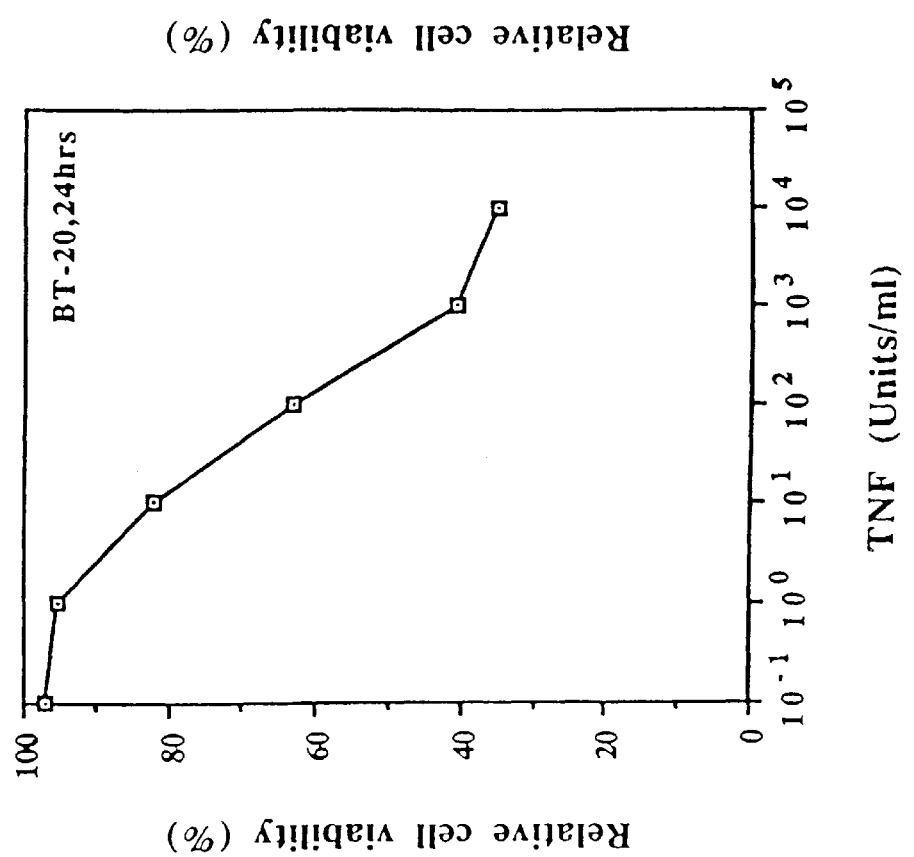
Figure 10F:
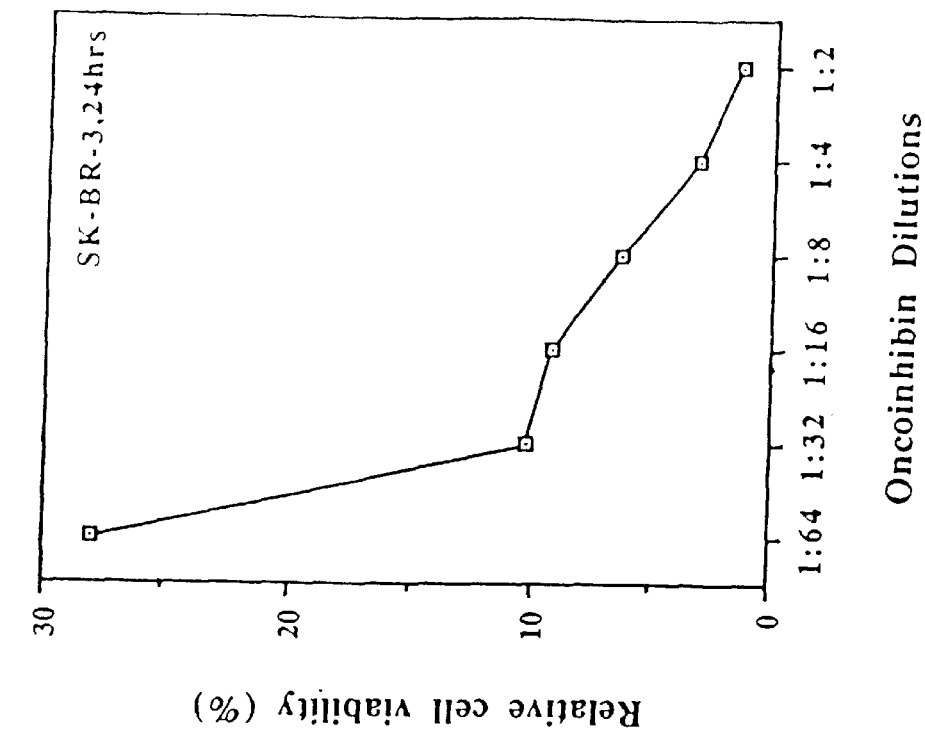
Figure 10E:
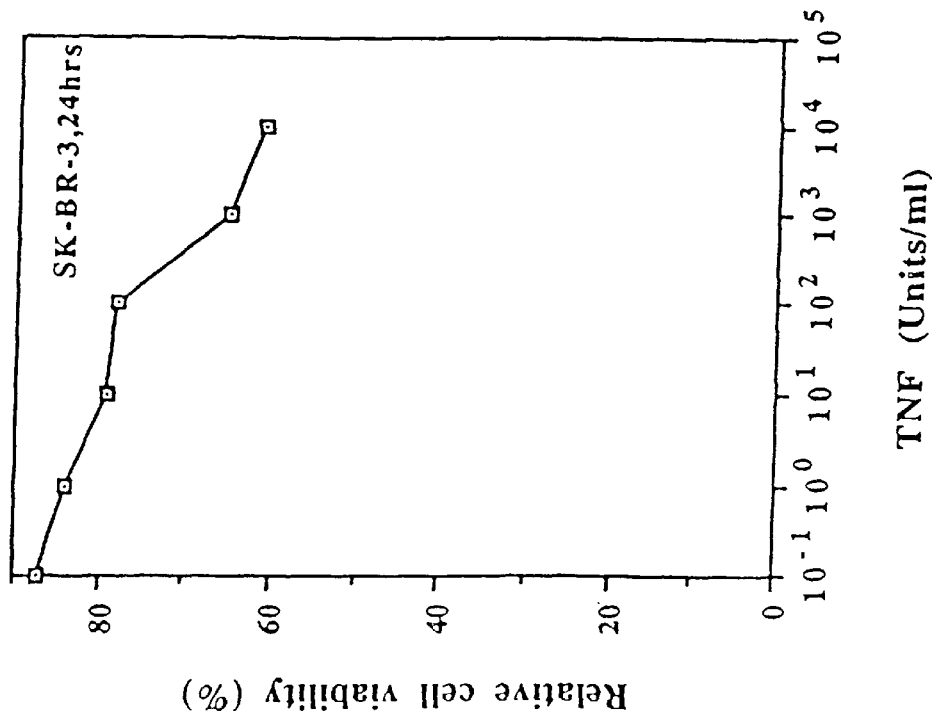
Figures 10G, 10H:
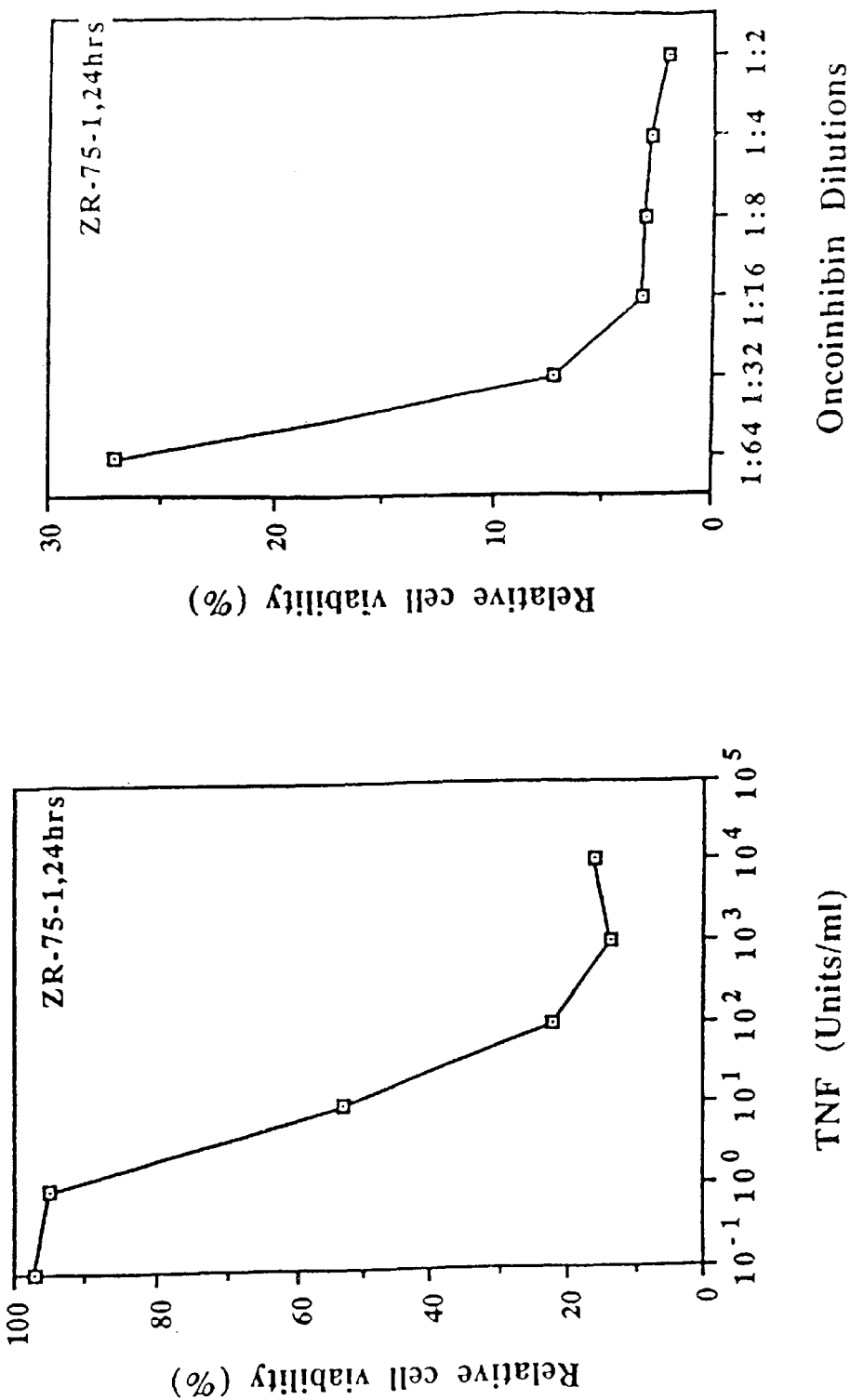
Figure 10J:
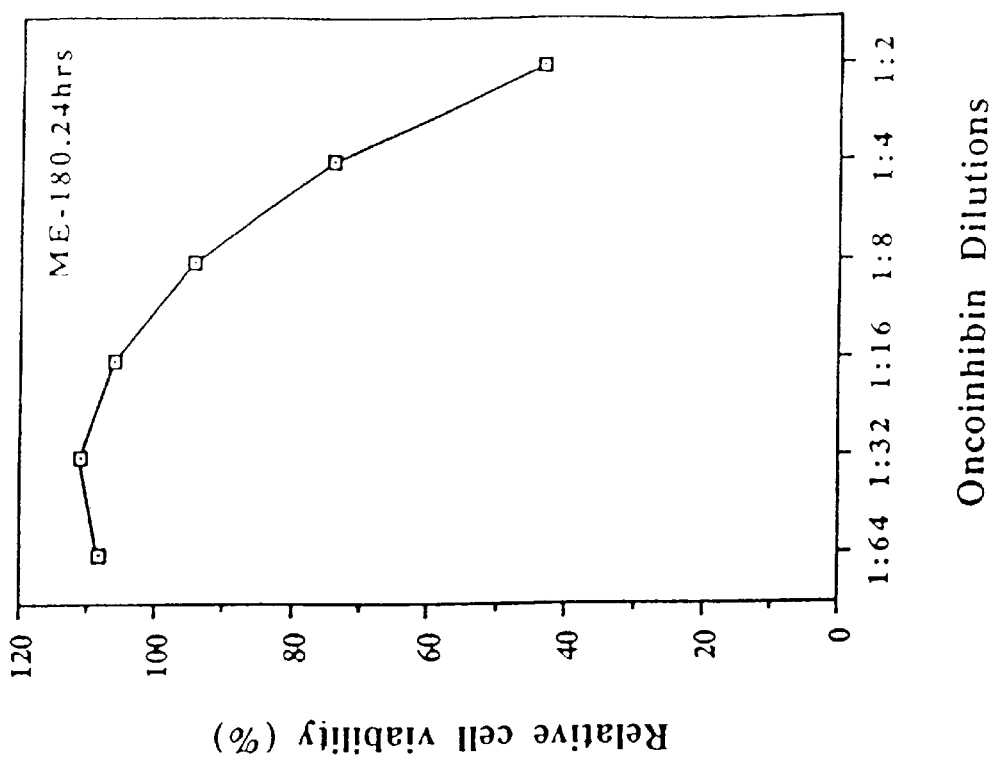
Figure 10I:
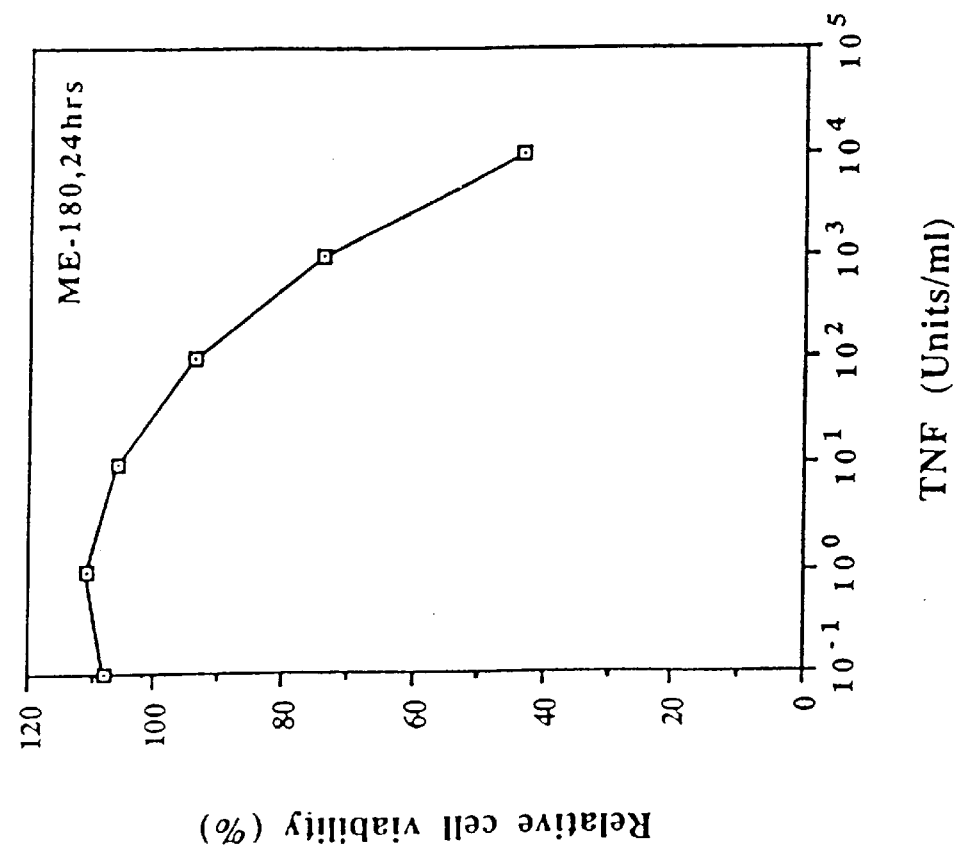
Figure 10L:
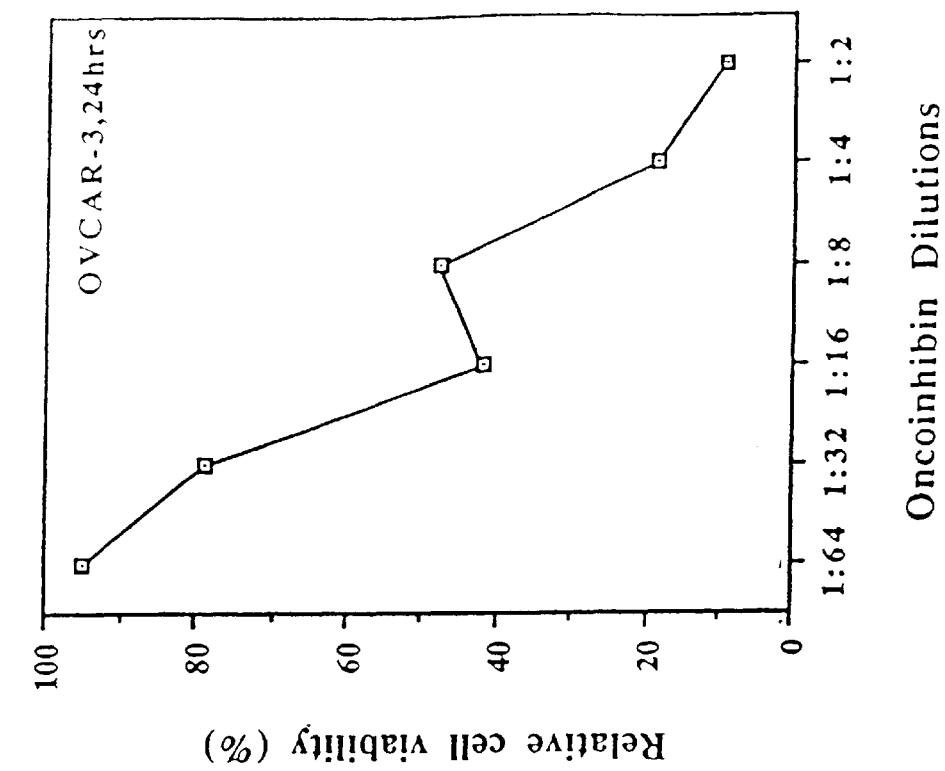
Figure 10K:
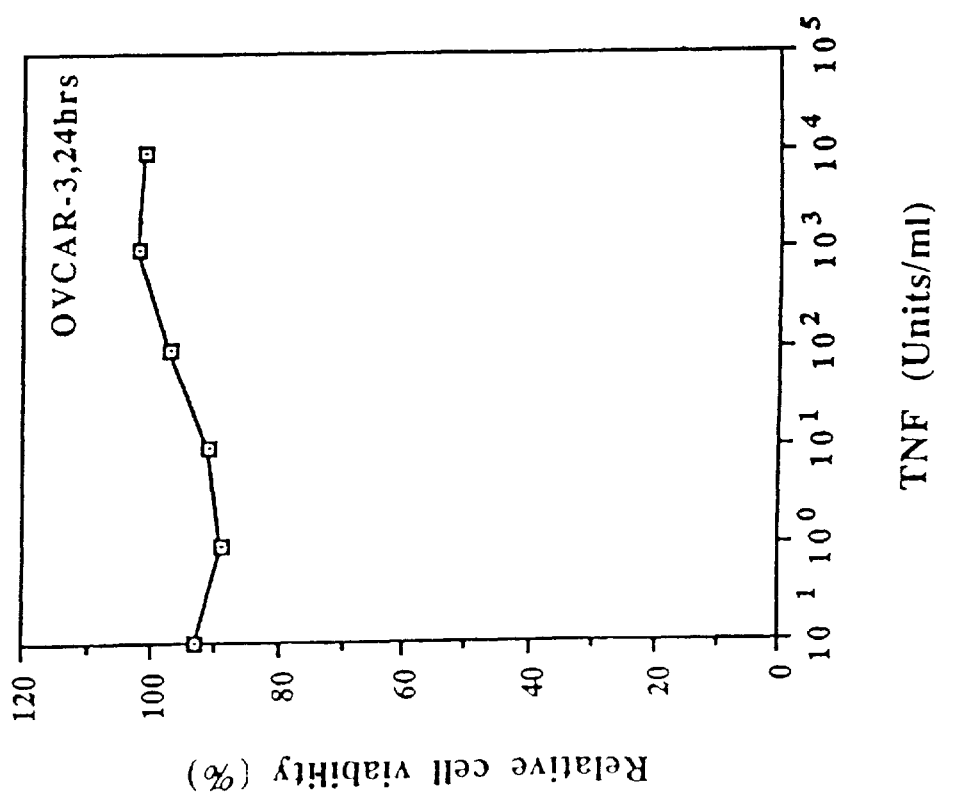
Figures 10M, 10N:
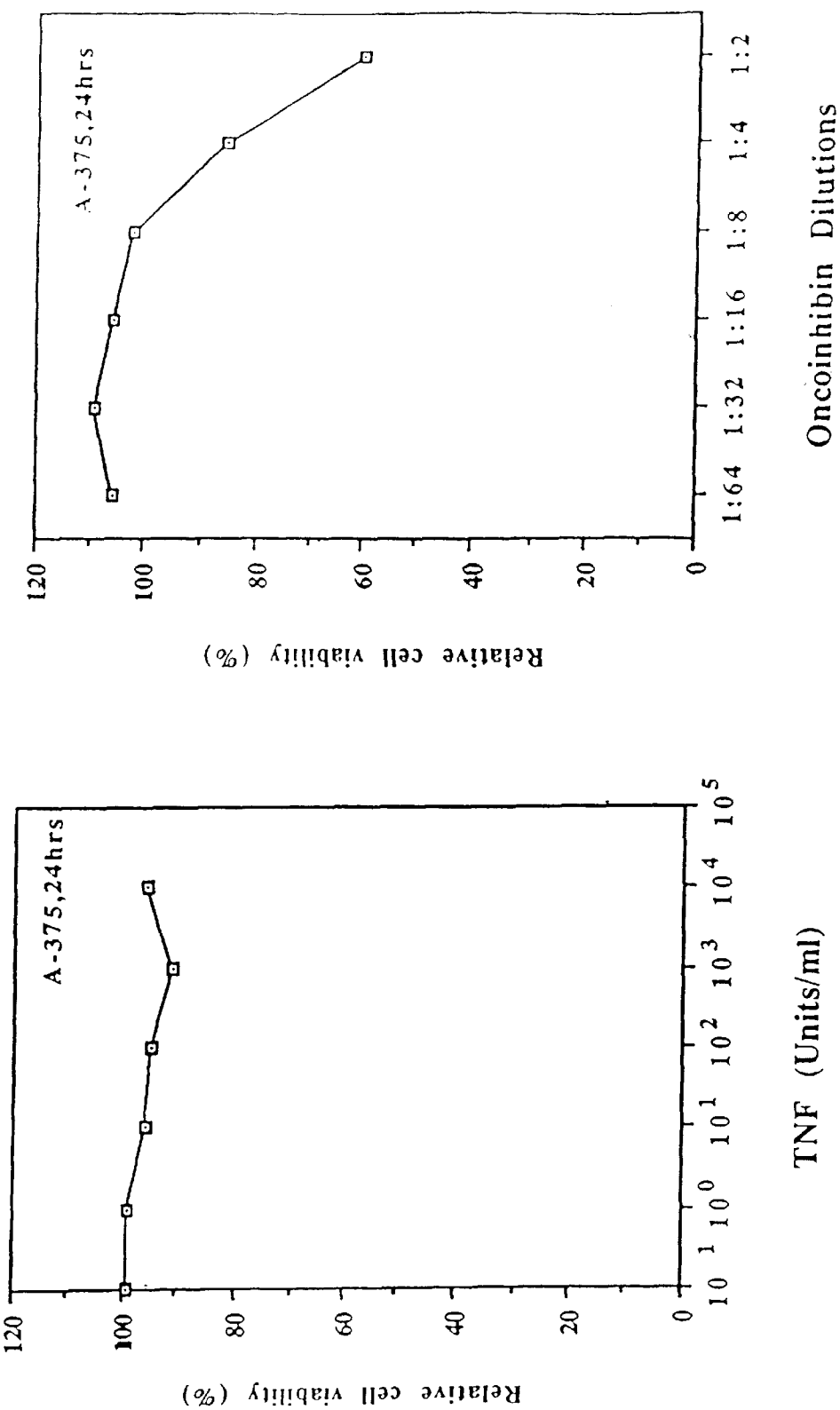
Figures 10O, 10P:
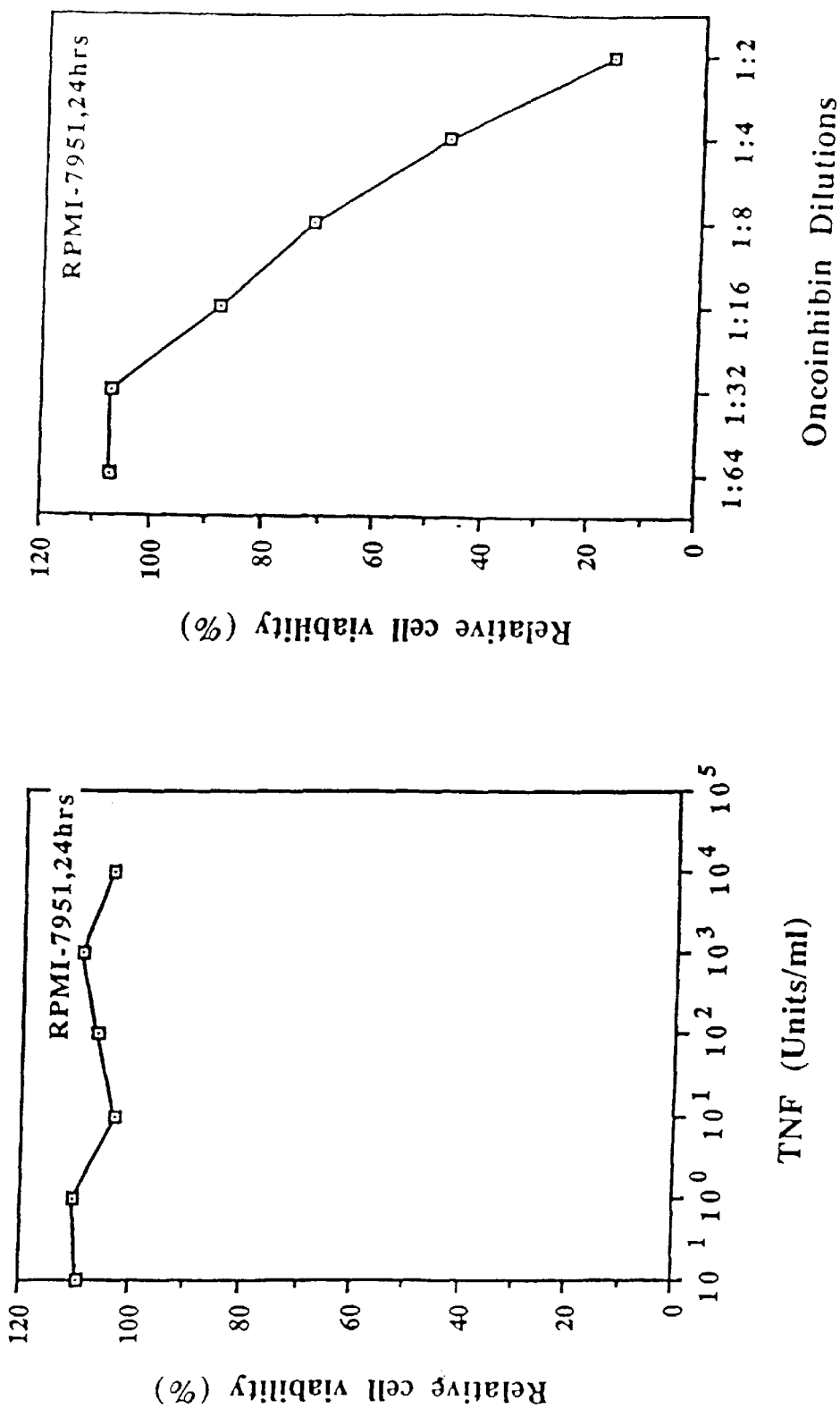

With reference to FIG. 9A and 9B, Oncoinhibin binding to and elution from anion exchange resins was examined.

One column (1 cm×5 cm) was packed with an anion exchange resin Q-Sepharose and then equilibrated with 20 mM Tris, pH 8.0 (equilibration buffer). A sample of Oncoinhibin dialyzed against the equilibration buffer was loaded onto the column with a flow rate of 0.5 ml/minute. The column was rinsed with the equilibration buffer and then resolved with a stepup gradients of NaCl (0–1 M). Various fractions were analyzed for protein concentration and for bioactivity.

DEAE Affigel Blue Chromatography: A second column (1 cm×5 cm) was packed with DEAE Affigel Blue resin and then equilibrated with 20 mM Tris, pH 8.0 (equilibration buffer). A sample of Oncoinhibin pre-equilibrated against the equilibration buffer by dialysis was loaded onto the column with a flow rate of 0.5 ml/minute. The column was rinsed with the equilibration buffer and then resolved with a step-up gradients of NaCl (0–1M). Various fractions were analyzed for protein concentration and for bioactivity.

FIGS. 9A and 9B show that Oncoinhibin binds and can be eluted from anion exchange resins. To both the Q-sepharose and DEAE affigel Blue resins, Oncoinhibin activity bound in 20 mM Tris, pH 8.0 buffer. The bound Oncoinhibin could be eluted with 0.2 M NaCl in 20 mM Tris buffer from DEAE affigel Blue and with 0.5 M NaCl from Q-sepharose.

Oncoinhibin inhibits the growth of wide variety of tumor cells. (Table III) The antiproliferative activity of Oncoinhibin was examined by tritiated thymidine incorporation.

TABLE III

Differences in tumor cell specificity between TNF and Oncoinhibin

| Cell Lines | Relative Cell Viability (%) | |
| --- | --- | --- |
| | TNF | Oncoinhibin |
| Erythroblastoid cell line (K562) | 94 | 2 |
| Histiocytic Lymphoma (U-937) | 54 | 1 |
| Histiocytic Lymphoma (U-937-CF- 1) | 13 | 0 |
| Promyelocytic Lymphoma (HL-60) | 100 | 1 |
| Burkitt Lymphoma (Raji) | 76 | 0 |
| T cell Lymphoma (Jurket) | 74 | 36 |
| Myelogenous Leukemia (KG-1) | 43 | 8 |
| Myelogenous Leukemia (KG-1a) | 60 | 13 |
| Myelogenous Leukemia (ML-1a) | 59 | 0.1 |
| Myelogenous Leukemia (ML-1b) | 35 | 0.1 |
| Monocytic Leukemia (THP-1) | 81 | 1 |
| Breast Carcinoma (BT20) | 24 | 2 |
| Breast Carcinoma(BT20TNFR) | 60 | 3 |
| Breast Carcinoma(MCF7) | 1 | 0 |
| Breast Carcinoma (SK-BR3) | 52 | 0 |
| Breast Carcinoma (ZR-75-1) | 6 | 1 |
| Melanoma (RPMI 7951) | 73 | 0 |
| Melanoma (A375) | 76 | 0 |
| Epidermoid Carcinoma (A-431) | 82 | 0 |
| Cervical Carcinoma (ME-1 80) | 20 | 0 |
| Ovarian Carcinoma (OVCAR-3) | 27 | 1 |
| Cervical Carcinoma (HeLa) | 55 | 14 |
| Hepatoma (HepG-2) | 83 | 20 |
| Retinoblastoma (Weri-Rb-1) | 60 | 33 |
| Retinoblastoma (Y-79) | 92 | 46 |
| Glioblastoma (LG) | 84 | 2.3 |
| Murine Fibroblasts (NIH 3T3) | 11 | 35 |
| Murine Fibroblasts (LTR1 000) | 85 | 27 |
| Murine Fibroblasts (L929) | 0 | 1 |
| Normal Human Foreskin Fibroblasts | 311 | 189 |

Tumor cells (5000/well) were incubated with TNF (0.2 $\mu$g/ml) or Oncoinhibin (induced by phorbol ester and concentrated) for 72 hours at 37° C. and then relative cell viability (%) was determined by thymidine incorporation as described previously.

With reference to FIGS. 10A–D, the dose response effects of Oncoinhibin on some of the cell lines listed in Table VII were examined and compared to TNF. It is clear from the results shown in Table VII and FIG. 10 that, besides MCF-7, Oncoinhibin can inhibit the growth of several different types of leukemias, melanomas, carcinomas and hepatomas. The growth of murine cells was also inhibited. Thus, it appears that, unlike interferons, Oncoinhibin is not species-specific.

Figure 11:
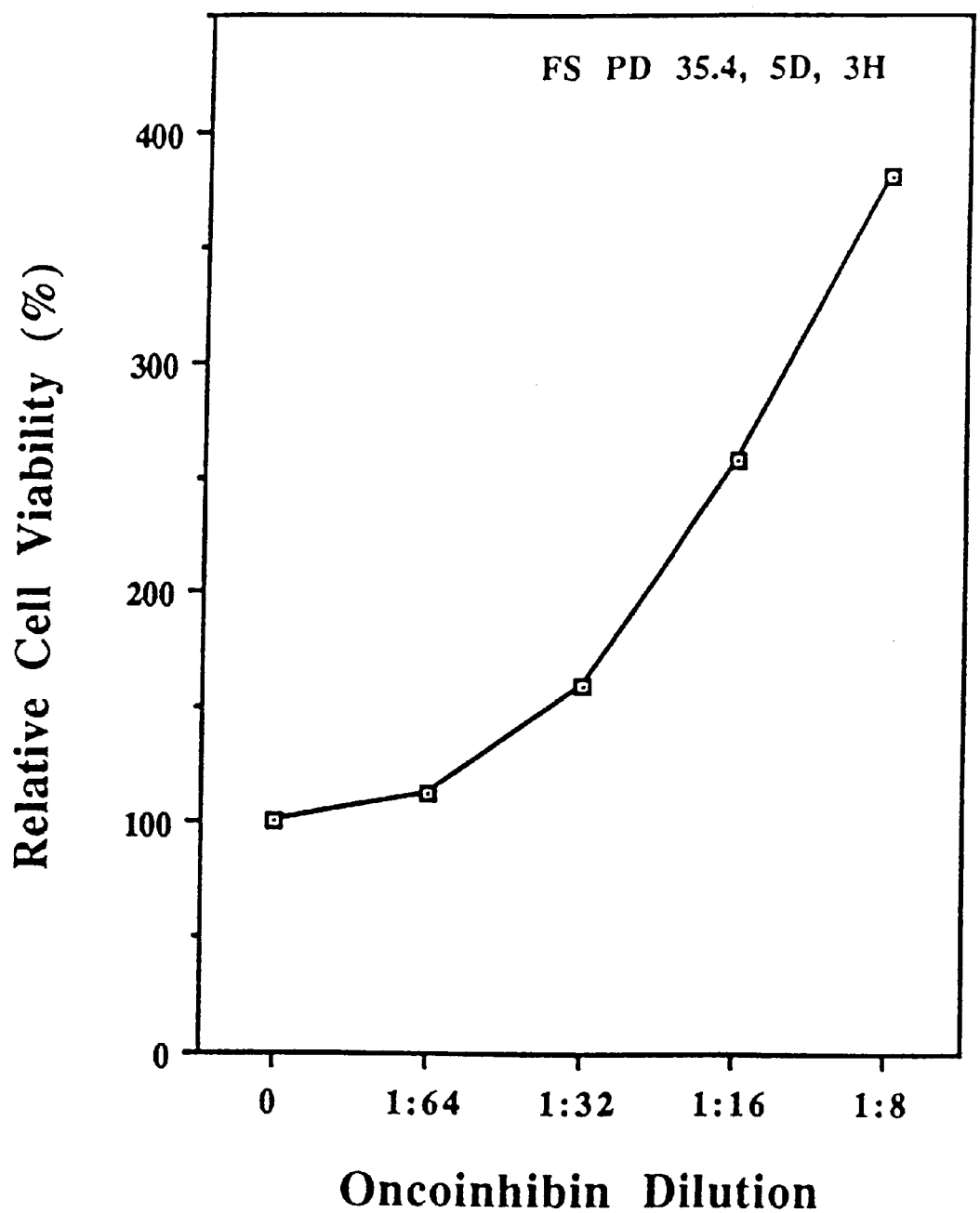
FIG. 11 shows dose dependent proliferative effects of Oncoinhibin on normal human foreskin fibroblasts.
Figure 12:
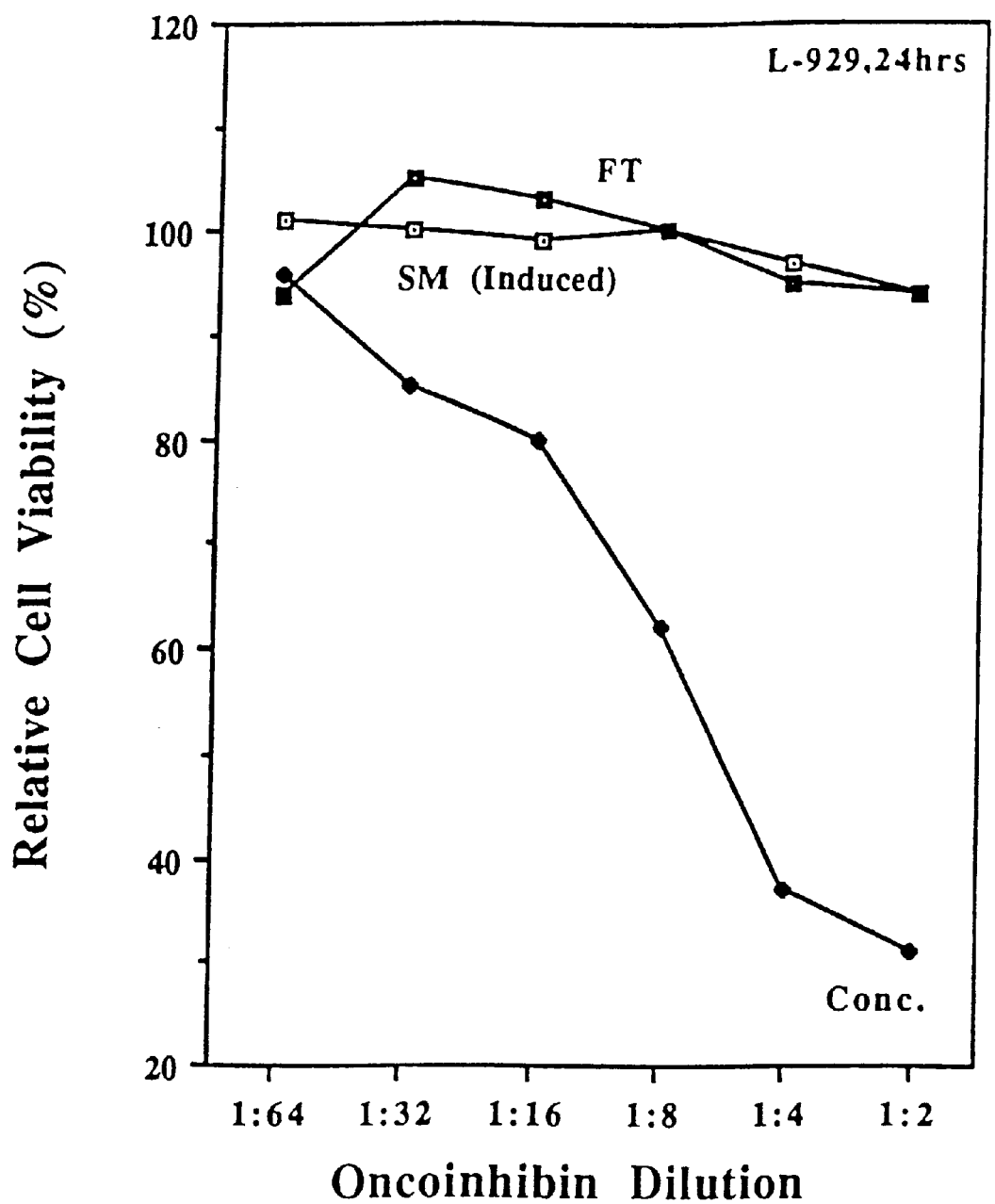
FIG. 12 shows the effect of Oncoinhibin on actinomycin D treated murine L-929 cells.

With reference to FIGS. 11 and 12, for growth assays, cells were plated for overnight in 0.1 ml of the medium (RPMI-1640 with 10% FBS) in 96-well Falcon plates. Thereafter, the medium was removed and a serial dilution of human Oncoinhibin was layered in 0.1 ml of the volume. After 72 hours of incubation at 37° C., the medium was removed and viable cells were monitored by crystal violet staining according to the procedure as described by B. B. Aggarwal, Human lymphotoxin, Meth. of Enzymol., 116:441–448 (1985), incorporated herein by reference. A dye uptake method to examine cell viability correlates with cell number determined by detachment with a trypsin solution and microscopic counting with hemocytometer. The percentage of relative cell viability was calculated as optical density in the presence of the test sample divided by optical density in the absence of the test sample (medium) multiplied by 100. For LT and TNF, cytotoxicity assays were carried out similar to growth inhibition assays except that $20\times10^3$ L-929 cells were treated with actinomycin D (1 $\mu$g/ml) along with the cytokine for 24 hours.

Cell Growth-Stimulatory Assays. Cell growth-stimulatory assays were carried out essentially according to the procedure described by Vilcek et al., J. Exp. Med. 163:632–643 (1986), incorporated herein by reference. Briefly, confluent human diploid foreskin fibroblasts at passage level 12–16 (corresponding to approximately population doubling levels 24–32) were used for cell growth stimulatory assays. To determine the effect of human Oncoinhibin, cells ($8\times10^3$/well) were plated in 0.1 ml of the medium (RPMI-1640+ 10% FBS) in 96-well Falcon plates. After overnight incubation in a $CO_2$ incubator at 37° C., the medium was removed and a serial dilution of the cytokine was layered in 0.2 ml of the volume. After 5 days incubation, media was decanted-off and cells were stained with crystal violet. All determinations were made in triplicate. Percent relative cell viability was calculated as indicated for growth-inhibitory assays.

For [$^3$H] TdR incorporation assays, human fibroblasts were cultured and treated with the cytokine for 5 days. During the last 24 hours, tritiated thymidine (6.7 Ci/mmole; New England Nuclear, Boston, MA) was added to each well (0.5 $\mu$Ci/well). Thereafter, the culture medium was removed, the wells were washed twice with phosphatebuffered saline and the cells were detached by the addition of a solution of trypsin (0.5%) with EDTA (5.3 mM). The cell suspension was then harvested with the aid of PHD cell harvester (Cambridge Technology Inc. Watertown, Mass.) and lysed by washing with distilled water. Radioactivity bound to the filter was measured in a liquid scintillation counter (Model 1600 TR; Packard Co., Meriden, Conn.). Thymidine incorporation in human fibroblast determined by this method correlates with cell growth. In tumor cell growth inhibition studies, cells were incubated with the cytokine for 3 days in a total of 0.1 ml final volume and then monitored for thymidine incorporation. With reference to FIG. 11, Oncoinhibin appears to stimulate the growth of normal human foreskin fibroblasts. While inhibiting the growth of tumor cells, Oncoinhibin enhanced the proliferation of normal human foreskin fibroblasts.

With reference to FIG. 12, similar to TNF and LT, Oncoinhibin cytolyses actinomycin D treated L-929 cells. The antitumor activity of Oncoinhibin against L-929 cells cannot be neutralized by either anti-LT or anti-TNF antibodies (Table IV). That is, no significant amounts of TNF or LT were detected by ELISA assay in Oncoinhibin preparations (Table V). Table III shows that several tumor cell types (e.g; SK-BR-3, HeLa, A-431, OVCAR-3, A375, and RPMI-7951) which are resistant to TNF/LT, are exquisitely sensitive to Oncoinhibin. Oncoinhibin can also be distinguished from TNF/LT on the basis of cell lines isolated for resistance to TNF/LT (NIH 3T3-LTR and BT-20 TNFR), were found to be sensitive to Oncoinhibin. (Table III)

TABLE IV

Lack of Neutralization of Oncoinhibin Activity by Monoclonal
Antibodies Against Tumor Necrosis Factor and Lymphotoxin*

| Sample | Antibody | RCV % | Neutralization % |
|---|---|---|---|
| Oncoinhibin | None | 58 | 0 |
| | +Anti-TNF | 58 | 0 |
| | +Anti-LT | 60 | 0 |
| | +Anti-TNF + Anti LT | 56 | 4 |
| TNF | None | 39 | 0 |
| | +Anti-TNF | 100 | 100 |
| | +Anti-LT | 44 | 5 |
| LT | None | 35 | 0 |
| | +Anti-LT | 90 | 90 |
| | +Anti-TNF | 38 | 0 |

*Oncoinhibin, TNF and LT were incubated with either Anti-TNF or Anti-LT antibodies at 37° C. for 1 hour and then directly assayed for remaining nonneutralized TNF or LT activity on Actinomycin D treated L-929 cells as described above.

TABLE V

Determination of Various Cytokines in a Crude Preparation of
Oncoinhibin Derived from K-562 Cells*

| Cytokine | Levels (pg/ml) |
|---|---|
| TNF-α | 3 ± 6 |
| TNF-β(LT) | 2 ± 0 |
| IL-1β | 0 |
| IL-6 | 155 ± 7 |
| IL-8 | >2000 |

Serum-free K-562 cell-conditioned media was used as a source of Oncoinhibin and the level of various cytokines were determined by standard ELISA assays (R&D System). ND is not determined TNF and LT are products of monocytes and lymphocytes, respectively, and inhibit the growth of a wide variety of cells. Similar to Oncoinhibin, lymphotoxin and TNF inhibit the growth of MCF-7 cells, but large concentrations of TNF and LT (10,000 units/ml) are needed.

To further confirm that Oncoinhibin is neither TNF nor LT, a northern blot analysis was performed to look for the gene for either of the cytokines. In the northern blot analysis, phorbol ester treated and untreated K-562 cell cultures seeded at $1\times10^6$ cells/ml in 75-cm flasks were incubated with protein kinase C activator for 24 hours and then harvested by centrifugation. Total RNA was extracted from cells by the guandinium isothiocyanatephenol-chloroform method shown by Chirgwin, et al., *Biochem.* 18:5294–5299 (1979) and Maniatis, et al., *Molecular Cloning* 188–209 (1982), incorporated herein by reference. Routinely, RNA with 260 nm/280 nm absorbance ratio of greater than 1.9 and yield of approximately 100 μg RNA per $20\times10^6$ cells was obtained.

For electrophoresis, 20 μg of RNA was fractionated on 0.8% agarose gels containing 2.2 M formaldehyde at 75–100 V for approximately 3 hours. Thereafter, gels were exposed to diethyl pyrocarbonate-treated water at 68° C. for 1 hour, and then the RNA transferred to Hybond nylon membranes (Amersham Corp., Arlington Heights, Ill. ). After transfer (3 hours), the filter was rinsed twice with SSC (SSC: 0.15 M sodium chloride, 15 mM sodium acetate, 15 mM sodium citrate, pH 7.0) and placed in a microseal bag.

Figure 13:
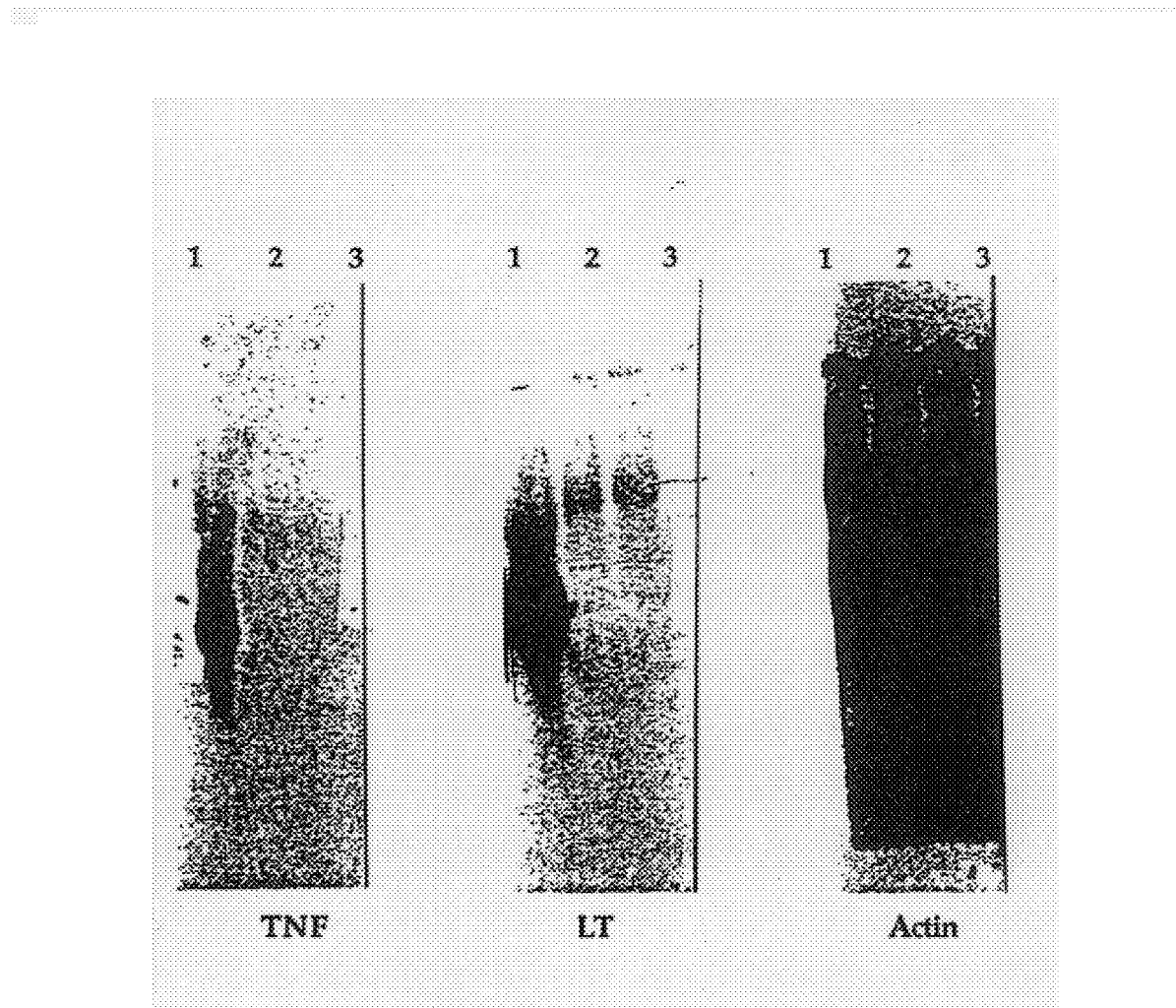
FIG. 13 shows a northern blot analysis for TNF and LT of K-562 cells untreated and treated with phorbol esters.

Prehybridization was carried out at 65° C. for 1 hour in a buffer containing 7% SDS, 500 mM sodium phosphate, 1 mM EDTA, pH 7.2 (hybridization buffer). Filters were then hybridized with TNF or LT cDNA probes (specific activity $2\times10^8$ cpm/μg DNA). After hybridization, membranes were washed several times at 65° C. in hybridization buffer containing salmon sperm DNA (200 μg/ml). The filters were exposed to Kodak XAR-5 film at −70° C. for 1–3 days. Procedures for sequential cycles of prehybridization, hybridization, washes and filter stripping were performed. Equal loading of lanes was demonstrated by examination of gels after ethidium bromide staining and also by rehybridization of same filters with cDNAs for either actin or glyceraldehyde 3-phosphate dehydrogenase (GAPDH). B and densitometry was performed by either scanning the filter for radioactive counts with blot analyzer Betascope 603 (Betagen Corp., Waltham, Mass.) or by scanning autoradiogram for optical density by using Scanning Densitometer (Helena Laboratories Inc. Beaumont, Tex.). As shown in FIG. 13, no expression of mRNA for either LT or TNF was observed in K-562 cells. Furthermore, gel filtration and SDS-PAGE experiments confirm that the molecular weight of Oncoinhibin is different from that of either TNF or LT.

Figure 19:
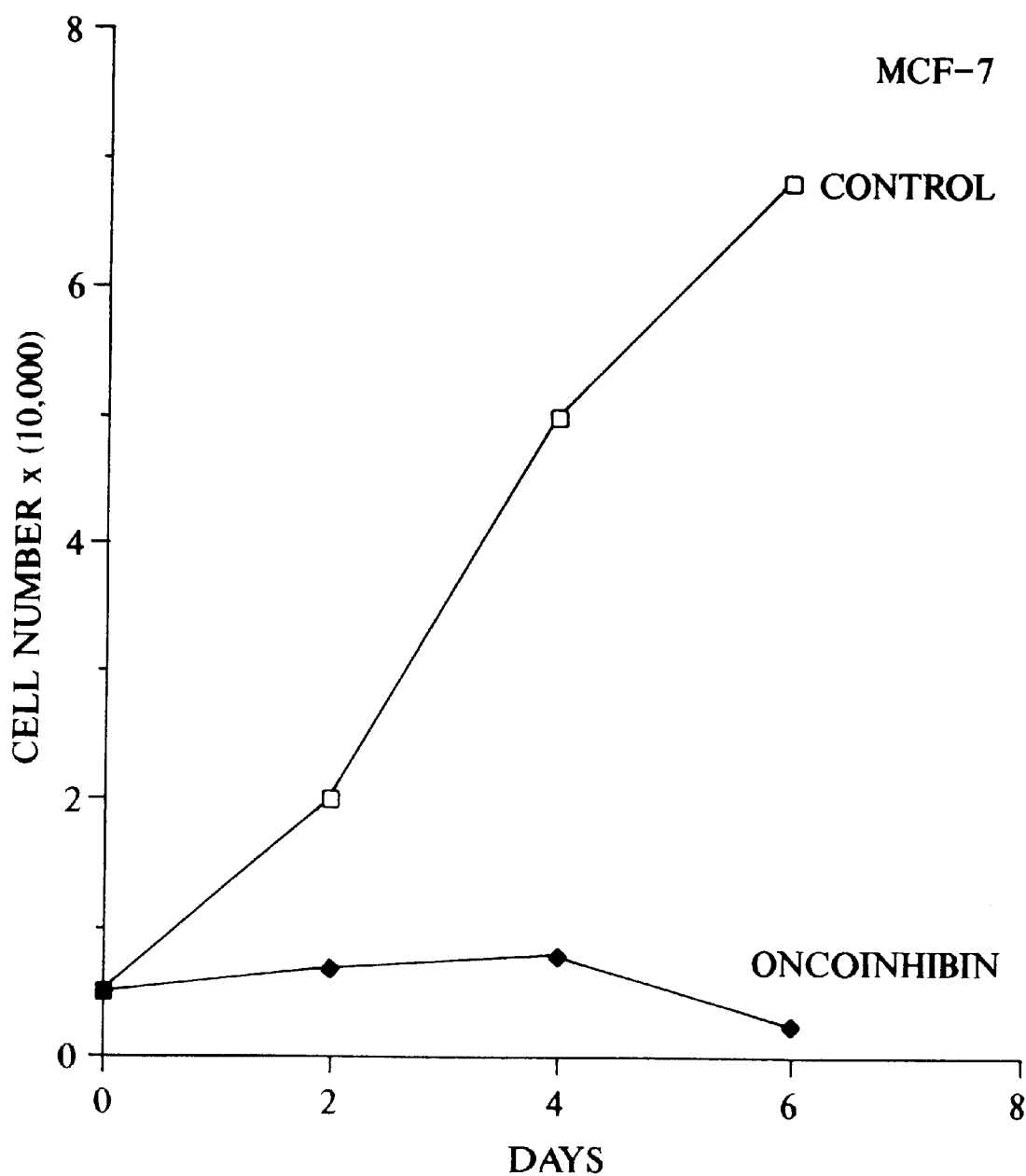
FIG. 19 shows the growth rate of human breast tumor MCF-7 cells in the absence and presence of Oncoinhibin.
Figure 20:
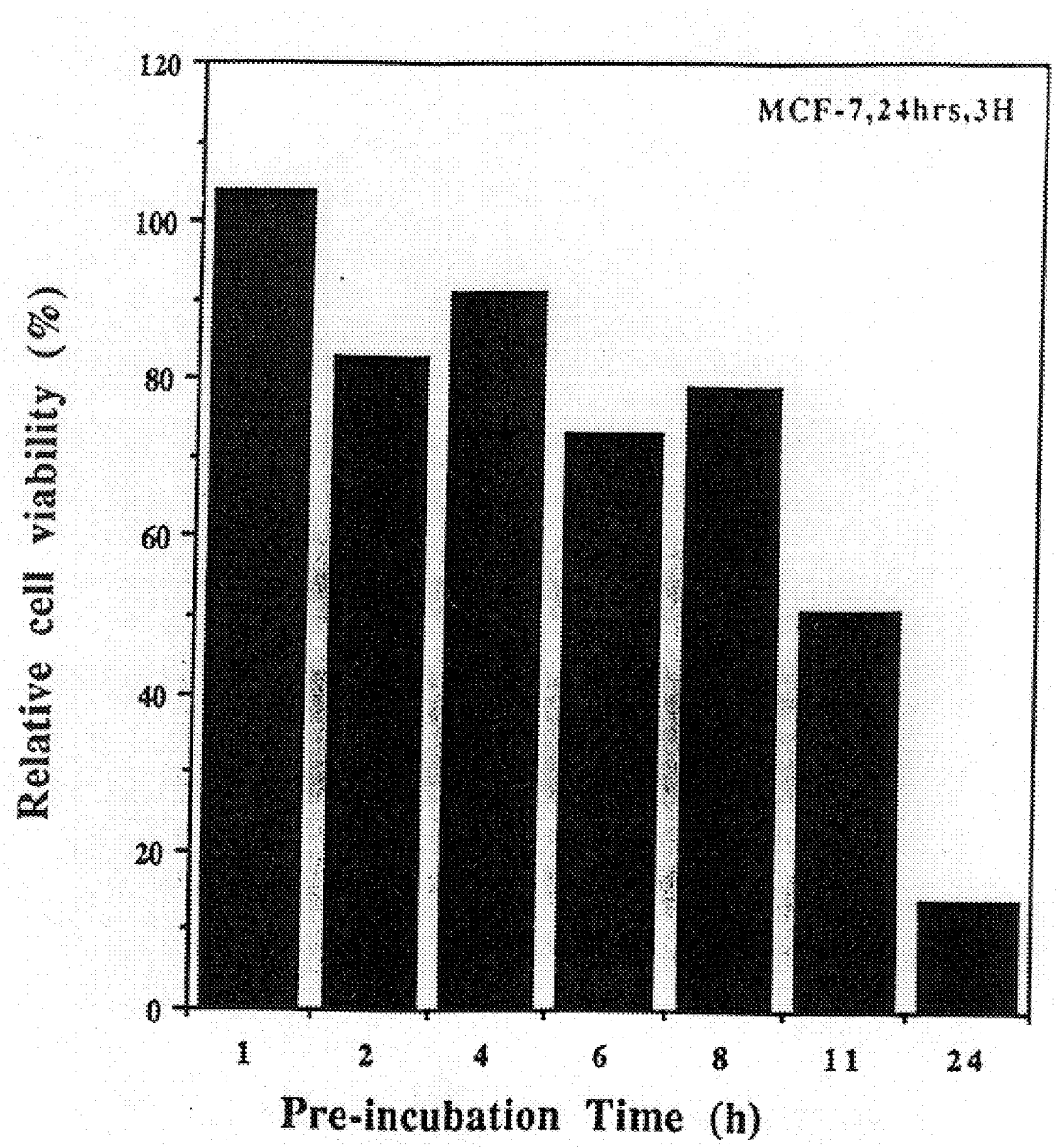
FIG. 20 shows the effect of time of exposure of MCF-7 cells to Oncoinhibin.

With reference to FIG. 19, human breast tumor cells grow rapidly in culture in the media. When Oncoinhibin was added to the culture, however, no growth of these cells was observed. In order to determine the time of exposure needed to inhibit the growth of these cells, the cells were exposed to Oncoinhibin for different times. With reference to FIG. 20, the growth-inhibitory effects of Oncoinhibin are terminated when the cytokine is removed from the media. These results suggest the need for continuous presence of the Oncoinhibin.

Figure 21:
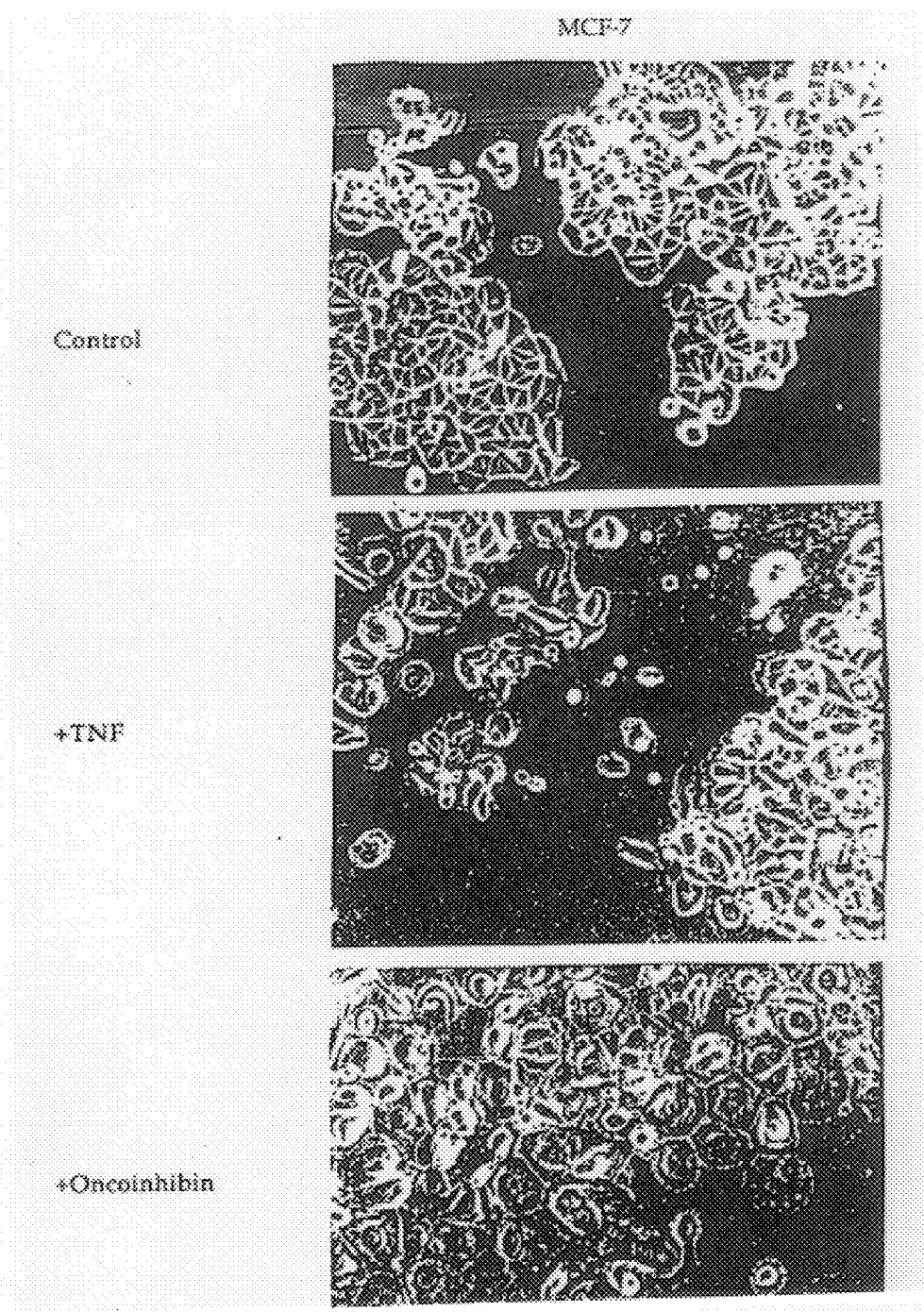
FIGS. 21A–21C show comparison of the effect of Oncoinhibin with TNF on the morphology of human breast tumor MCF-7 cells.

With reference to FIG. 21, the morphology of the MCF-7 cells was examined after treatment with Oncoinhibin and compared to TNF. The results indicate a difference in the method by which TNF and Oncoinhibin inhibit the growth of breast tumor cells. TNF induces rounding-up of the cells which leads to their detachment from the dish, while Oncoinhibin induces enlargement or swelling of cells. The latter may result from effects of Oncoinhibin on the permeability of the cells. Oncoinhibin also inhibits the colony formation of human breast tumor cells.

Oncoinhibin Stability Studies. Oncoinhibin was treated with organic solvent (acetonitrile or methanol or propanol), acidic solvents (HCl, trichloroacetic acid or acetic acid), alkaline solvents (NaOH, Ammonium hydroxide) or detergents (SDS, Tween 10) for two hours at room temperature, then dialyzed against 20 mM Tris-HCl, pH 8.0 overnight in a cold room and assayed for biological activity. (Tables VI and VIII).

For thermostability experiments, Oncoinhibin was exposed to different temperatures for different times and the biological activity was determined directly. The biological activity of Oncoinhibin was found to be stable to 80° C. for 60 minutes but approximately 50% loss of activity was observed when exposed to 100° C. for 30 minutes (Table VI).

TABLE VI

Thermostability of Oncoinhibin at Different Temperatures

| Temperature(° C.) | Time(min) | Activity Remaining U/Ml | % |
|---|---|---|---|
| 4 | 60 | 256 | 100 |
| 80 | 30 | 210 | 82 |
|  | 60 | 230 | 90 |
| 90 | 30 | 200 | 78 |
|  | 60 | 190 | 74 |
| 100 | 30 | 128 | 50 |
|  | 60 | 110 | 43 |

In Table VII, Oncoinhibin was treated with pronase E, trypsin, chymotrypsin and V8 Staph protease and then analyzed for its biological activity. The results indicate that Oncoinhibin activity can be completely abolished by pronase E, thus suggesting that it is a protein. Its activity was found to be partially sensitive to trypsin treatment and completely resistant to chymotrypsin and V8 protease. Deoxyribonuclease also had no effect on the activity of Oncoinhibin.

TABLE VII

Effect of Proteolytic Enzymes on the Activity of Oncoinhibin

| Enzymes | Conc. | Activity Remaining (%) |
|---|---|---|
| None | 10% (w/w) | 100 |
| Pronase E | 10% (w/w) | 0.2 |
| Trypsin | 10% (w/w) | 50 |
| V8 Staph. Protease | 10% (w/w) | 100 |
| Chymotrypsin | 10% (w/w) | 100 |
| Deoxyribonuclease | 10% (w/w) | 100 |

Oncoinhibin was incubated with various enzymes at 37° C. for 24 hours in 20 mM Tris buffer at pH 8.0, then reaction was stopped by addition of 10% serum and assayed for Oncoinhibin activity.

Stability of Oncoinhibin to Detergents: A sample of Oncoinhibin was treated with different concentrations of either SDS, a negatively charged detergent or Tween 20, a neutral detergent for 2 hours, dialyzed and then assayed for biological activity. Bovine serum albumin treated with the same detergent was used as a control. The results of these experiments is shown in Table V. No loss of biological activity was observed on treatment of the protein either with SDS or Tween 20. In case of SDS, it appears that there is a significant increase in the biological activity of Oncoinhibin in a dose-dependent manner. The increase was not significant with Tween 20.

TABLE VIII

Effect of Detergent, pH and Organic Solvents on the Stability of Oncoinhibin

| Agent | Conc. | Activity Remaining U/ml | % |
|---|---|---|---|
| Detergent Stability: |  |  |  |
| Sodium dodecyl sulfate | None | 19 | 100 |
|  | 0.01% | 23 | 124 |
|  | 0.05% | 45 | 243 |
|  | 0.10% | 61 | 330 |
|  | 0.50% | 59 | 319 |
| Tween-20 | 0.01% | 24 | 130 |
|  | 0.05% | 24 | 130 |
|  | 0.10% | 16 | 88 |
| pH Stability: |  |  |  |
| Glycine pH2.0 | 0.1M | 240 | 300 |
| Acetic acid pH2.4 | 1.0M | 256 | 320 |
| Sodium acetate pH4.0 | 0.1M | 83 | 104 |
| Sodium acetate pH6.0 | 0.1M | 76 | 95 |
| Tris-HCL pH8.0 | 0.02M | 80 | 100 |
| NaHCO3 pH10.0 | 0.1M | 92 | 115 |
| NH40H pH11.4 | 1.0M | 185 | 231 |
| Organic Solvent Stability: |  | S/P |  |
| None | — | 42 | 100 |
| Methanol | 50% | 81/2 | 198 |
| Propanol | 50% | 56/3 | 140 |
| Acetone | 70% | 23/26 | 117 |
| Ethanol | 70% | 56/4 | 143 |
| Acetonitrile | 50% | 153/4 | 374 |

Oncoinhibin samples were treated at room temperature with the various agents for 1 hour in 20 mM Tris buffer pH 8.0, dialyzed overnight and then assayed for biological activity remaining. S and P represents supernatant and pellet fractions.

Stability of Oncoinhibin to reducing agents: Oncoinhibin was treated with different concentrations of dithiothreitol for 2 hours, then dialyzed and assayed for biological activity. The results of these experiments are shown in Table IX. It is clear that the activity of Oncoinhibin is unstable to the treatment of DTT. A 50% loss in activity with 1 mM DTT and 67% loss with 100 mM DTT was observed.

TABLE IX

Stability of Oncoinhibin to Various Treatments

| Agent | Conc. | Activity | Percent |
|---|---|---|---|
| Reducing Agents (DTT) | — | 256 | 100 |
|  | 1 mM | 128 | 50 |
|  | 10 mM | 96 | 38 |
|  | 100 mM | 84 | 33 |
| Trichloroacetic acid | 5% Sup. | 11 | 4 |
|  | Ppt. | 256 | 96 |
| Amm. Sulfate | 70% Sup. | 11 | 2 |
|  | Ppt. | 538 | 98 |

Oncoinhibin samples were treated with various agents, dialyzed and then assayed for biological activity.

Oncoinhibin can be concentrated by trichloroacetic acid and ammonium sulfate. Oncoinhibin was treated with different concentrations of either TCA or $NH_4SO_4$, centrifuged, resuspended, dialyzed and then assayed for biological activity. The results shown in Table IX indicate that all the activity of Oncoinhibin can be precipitated by either 5% TCA or by 70% (SAS) ammonium sulfate. Thus, these results also suggest the proteinaceous nature of Oncoinhibin.

Amphiregulin is glycoprotein that was isolated from phorbol ester-treated MCF-7 cells and inhibits the growth of A431 cells. Amphiregulin has an apparent molecular weight of 22.5 kDa. Both Oncoinhibin and amphiregulin inhibit the growth of tumor cells. Oncoinhibin, however, is not produced by phorbol-ester treated MCF-7 cells. Secondly, even though both Oncoinhibin and amphiregulin exhibit antiproliferative activity against A431 cells (Table III), amphiregulin, in contrast to Oncoinhibin, is inactive against human melanoma (A375), human adenocarcinoma of the breast (ZR-75-1 or MCF-7), human adenocarcinoma of the lung (A-549), human carcinoma of colon (H3347) human lymphoblastoid T cells (CEM), human EBV transformed B cells, human epidermal carcinoma of larynx (Hep 2), bovine fetal heart endothelial cells (CRL-1395), murine BALB/3T3, and mink lung (CCL-64) cells. Similar to Oncoinhibin, amphiregulin stimulates the proliferation of human fibroblasts. Besides human fibroblasts, amphiregulin also stimulates the growth of certain tumor cells including human pituitary tumor cells (CRL 7386), human ovarian carcinoma cells (HTB 77), African green monkey kidney cells (BSC-1) and rat kidney cells (NRK). The molecular weight of Oncoinhibin, however, is also significantly different from that of amphiregulin and the mature form of the latter is an 84 amino acid long protein.

Oncoinhibin is stable to both acidic and alkaline conditions at a pH range of 2.0–10.0 (Table VIII). Several cytokines have been reported which are stable to pH 2, including IFN, IL-2, IL-4, IL-8, CSF-1, GM-CSF, TGF-$\beta$, Oncostatin M and amphiregulin. Oncostatin M, amphiregulin, CSF-1 and IL-4 were also found stable to alkaline conditions (pH 12). Recently, lipolysis promoting factor (LPF), a protein with an approximate molecular weight of 6 kDa, has been isolated from A375 melanoma cell line which is stable to heat 96° C. for 10 minutes), protease K (10 $\mu$g/ml), trypsin, pronase, RNase, DNase and periodate oxidation. LPF can be precipitated by trichloroacetic acid (10%) without any loss of biological activity. Oncoinhibin was found to be stable to heat up to 80° C. for 30 minutes and only partial activity was lost at 100° C. (Table VI). A trypsin 10% (w/w) treatment of Oncoinhibin for 24 hours at 37° C. lead to a partial loss of biological activity. This is similar to that observed with CSF-1, GM-CSF and LT. The biological activity of Oncoinhibin was also found stable to 0.5% SDS.

Oncoinhibin is distinct from Tumor Killing Factor (TKF), a cytokine identified from human macrophage-monocyte hybridoma in that TKF is a basic protein (pI 8–9.0), has an apparent molecular weight of 56 kDa by gel filtration and can be eluted from Conconavaline Asepharose with 0.4 M alpha-methyl mannoside.

Figure 14A:
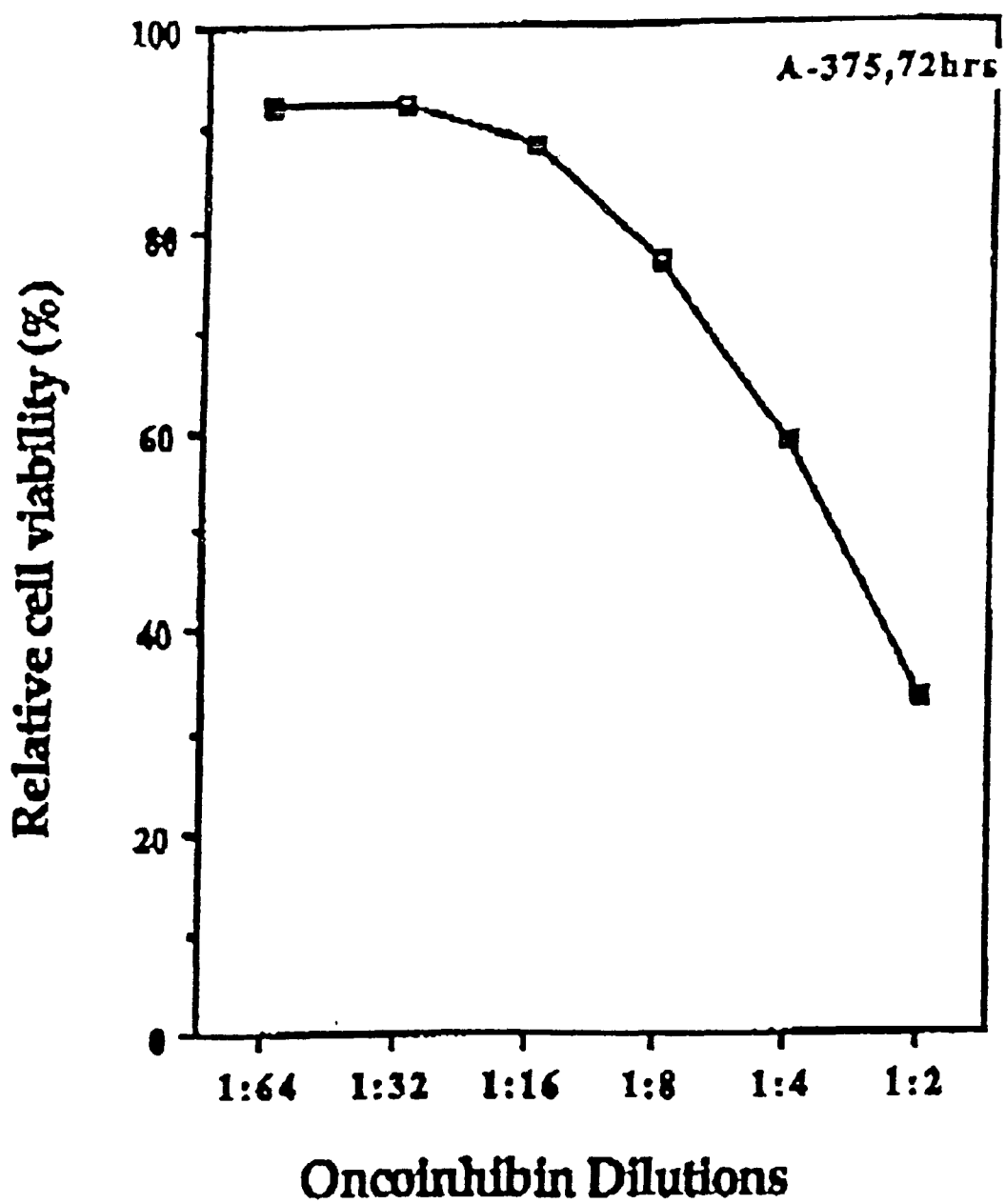
FIGS. 14A and 14B show the comparison of growth inhibitory effects of Oncoinhibin (14A) and oncostatin M (14B) on human melanoma A375 cells.
Figure 14B:
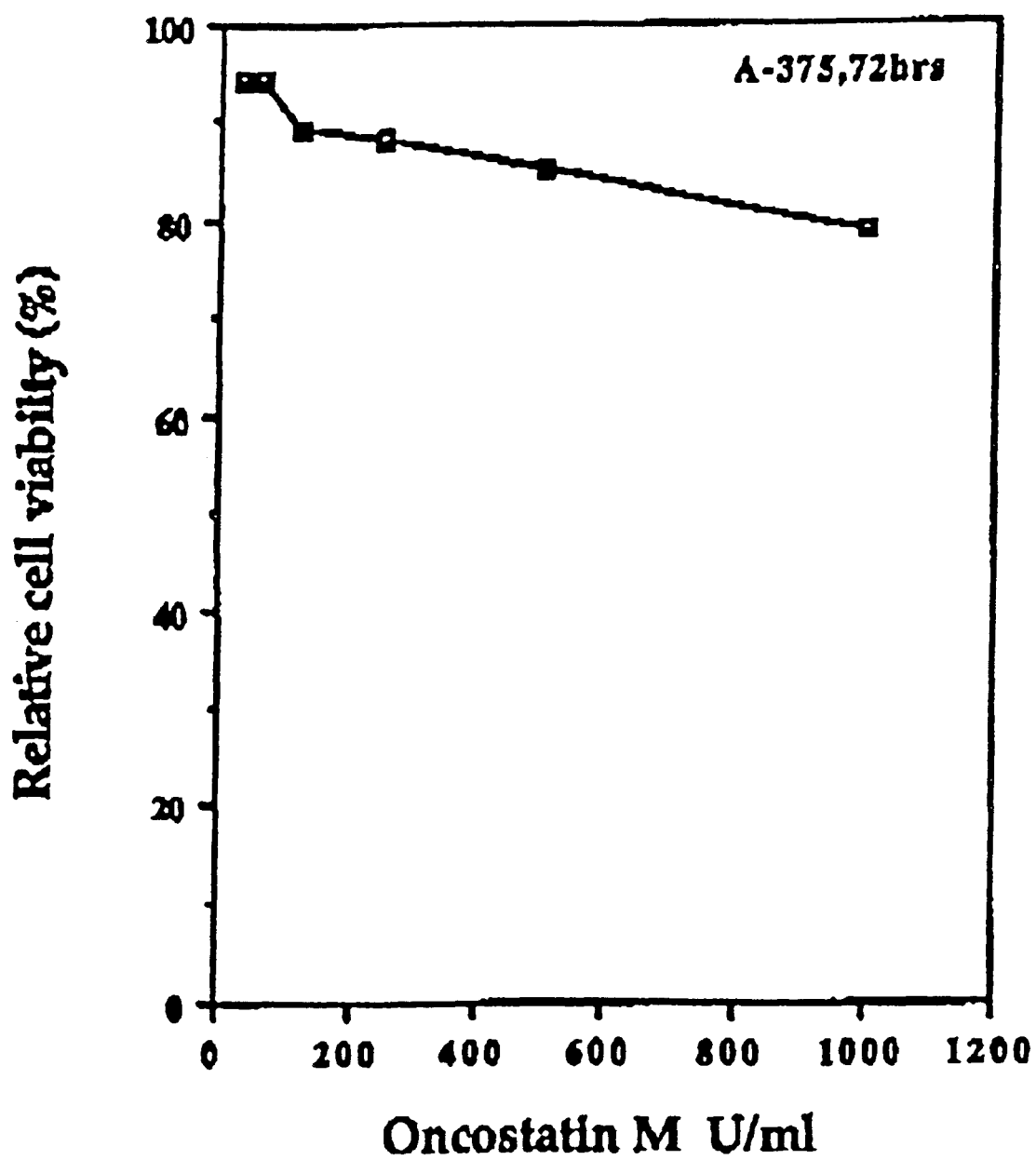

Oncostatin M is a cytokine isolated from U-937 cells treated with phorbol ester and inhibits the growth of human melanoma cell line A375 in a thymidine incorporation assay. Unstimulated U-937 cells do not express the gene or secrete this activity. Phytohemagglutininactivated human peripheral blood T lymphocytes also express the gene and secrete this cytokine. Oncostatin M is a glycoprotein with a molecular weight of 28 kDa by SDS-PAGE and 18 kDa by gel filtration. It synergizes with TGF-$\beta$ but not with interferons. Oncostatin M has been shown to inhibit the proliferation of HTB 10 neuroblastoma cells, A-549 lung carcinoma cells, as well as A375 and SKMEL-28 melanoma cells; it does not, however, inhibit the proliferation of L-929 cells. In contrast, Oncoinhibin is produced by K-562 cells (not by U-937 cells) both in the presence as well as in the absence of phorbol ester and affects L-929 cells. Moreover, in contrast to Oncoinhibin, oncostatin M is a relatively weak inhibitor of A375 cells (FIG. 14).

Transforming growth factor-$\beta$ (TGF-$\beta$) is cytokine which is a homodimer with a molecular weight of 25 kDa on SDS-PAGE and inhibits the growth of several cell types of epithelial and mesenchymal origin including human vascular endothelial cells, T and B lymphocytes. A-549, MCF-7 cells are also inhibited by TGF-$\beta$ in an autocrine manner. However unlike Oncoinhibin, TGF-$\beta$ is produced by a wide variety of cells including platelets, bone tissue and lymphocytes, and requires acid-activation before its activity can be examined. In addition, TGF-$\beta$ has a molecular weight of 12.5 kDa on SDS-PAGE under reduced conditions.

Cytokine ELISA assays: A commercially available (R&D Systems) quantitative "sandwich" enzyme immunoassay technique was used to examine the presence of known cytokines (TNF, LT, IL-1, IL-6 and IL-8) in the Oncoinhibin preparation. The standard protocol provided by the supplier was used. Briefly, a monoclonal antibody specific for different cytokines was coated onto the microtiter plates and allowed to set up overnight to immobilize the antibodies. Then the samples were pipetted into the wells and the cytokine if any is captured by the immobilized antibody. After washing away any unbound sample proteins, an enzyme-linked polyclonal antibody specific for a given cytokine was added to the wells and allowed to bind the cytokine which was bound during the first incubation. Following a wash to remove any unbound polyclonal antibody-enzyme reagent, a substrate solution was added to the wells and color developed in proportion to the amount of cytokine bound in the initial step. Along with the samples tested, a series of wells were prepared using known concentrations of the cytokine standards. A curve plotting the optical density versus the concentration of cytokine in these standard wells was prepared by comparing the optical density of the samples to this standard curve. The concentration of the cytokine in the unknown samples was then calculated (Table V).

Interleukin-1 is a cytokine produced by activated monocytes and fibroblasts, has a molecular weight of 17 kDa and inhibits the growth of tumor cell lines including ovarian carcinoma, A375 melanoma, K-562 and certain breast tumor cell lines. Oncoinhibin, however, differs from Interleukin-1 with respect to its source, molecular weight and tumor specificity. Crude preparations of Oncoinhibin were examined for the presence of IL-I by ELISA. The results shown in Table V demonstrate a lack of presence of the IL-I protein in our Oncoinhibin preparation.

Figure 15A:
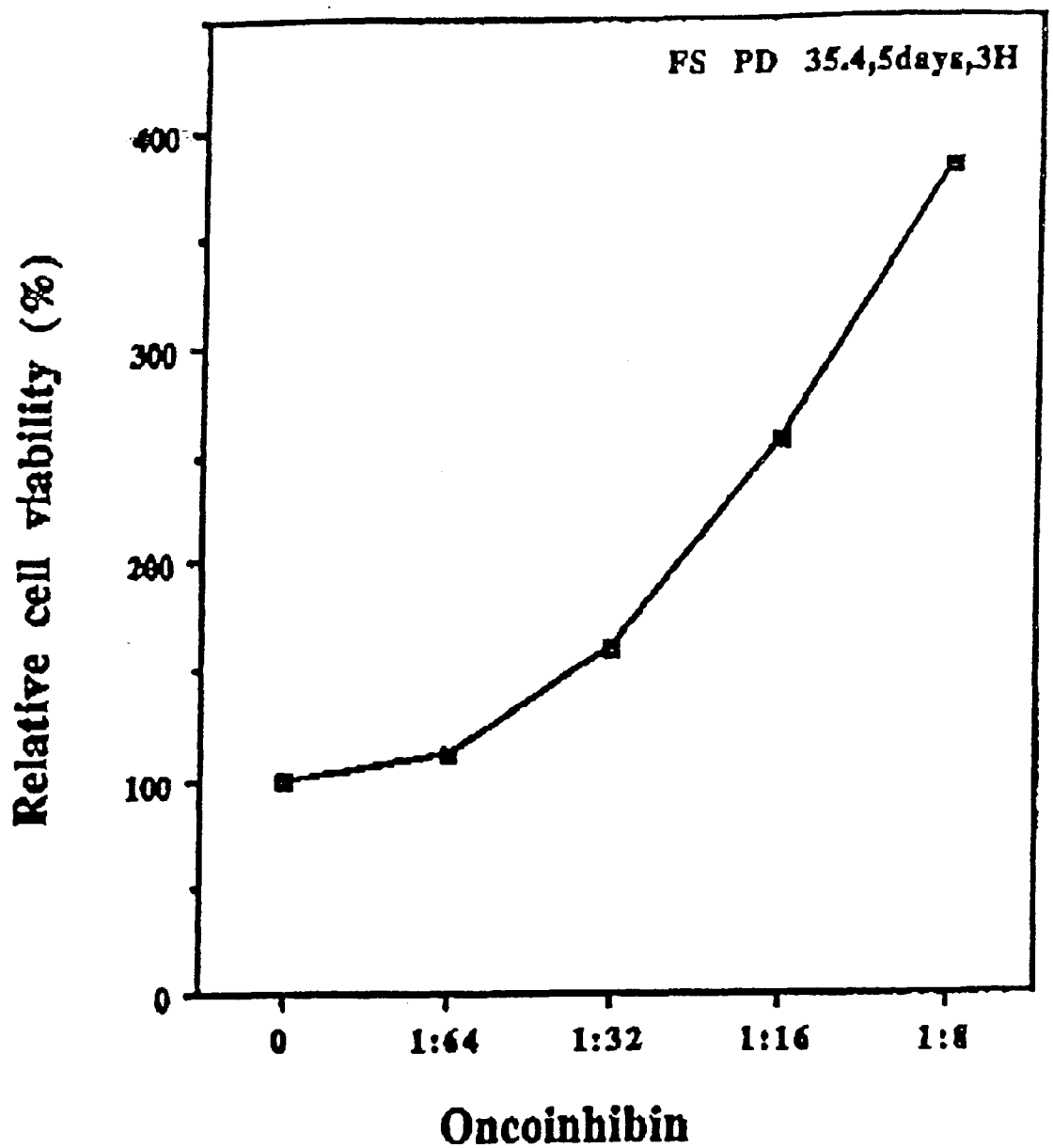
FIGS. 15A and 15B show the growth inhibitory effects of oncostatin M and IL-6 on normal fibroblasts.
Figure 15B:
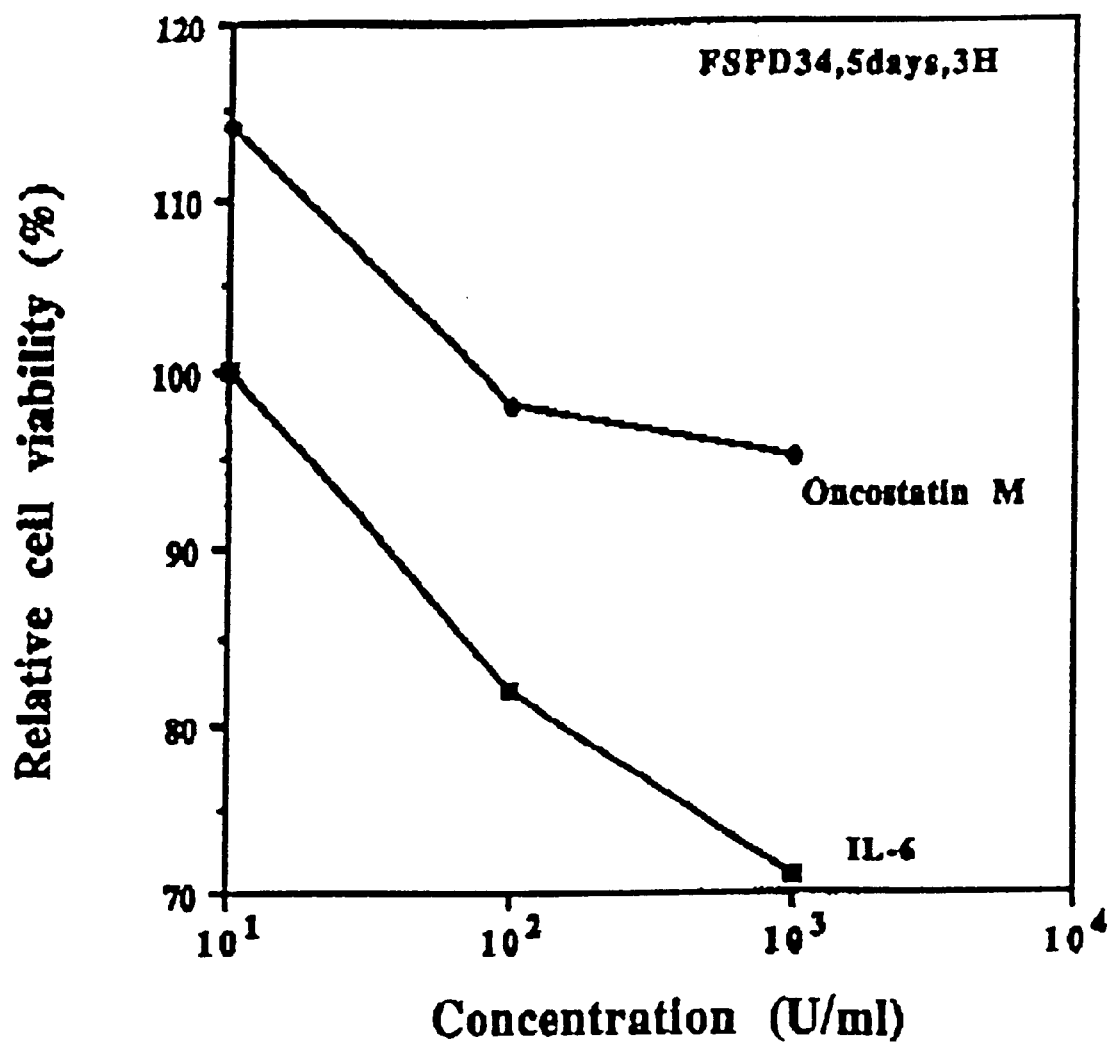
Figure 16A:
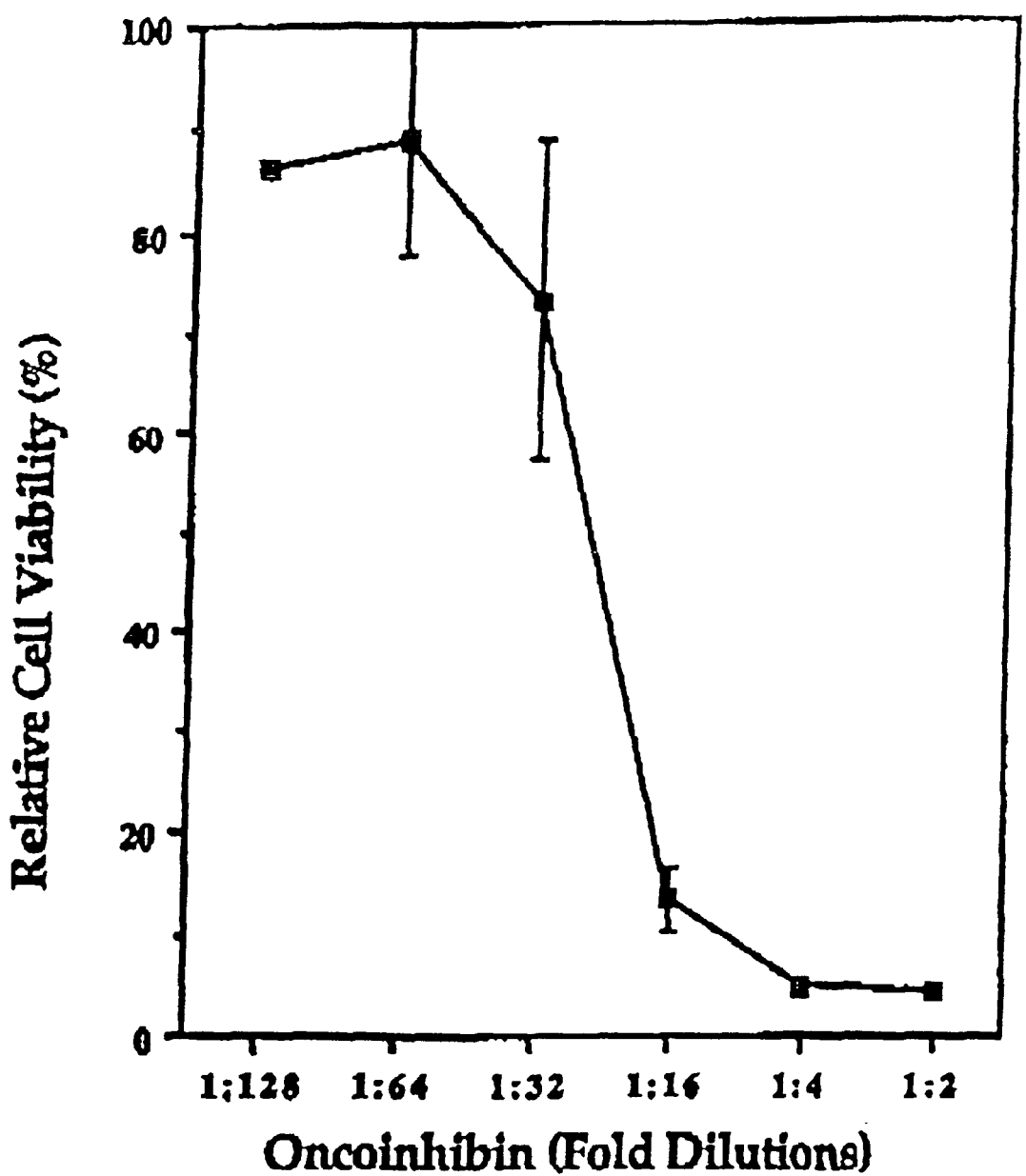
FIGS. 16A and 16B show the effect of IL-6 on human breast tumor (MCF-7) cells.
Figure 16B:
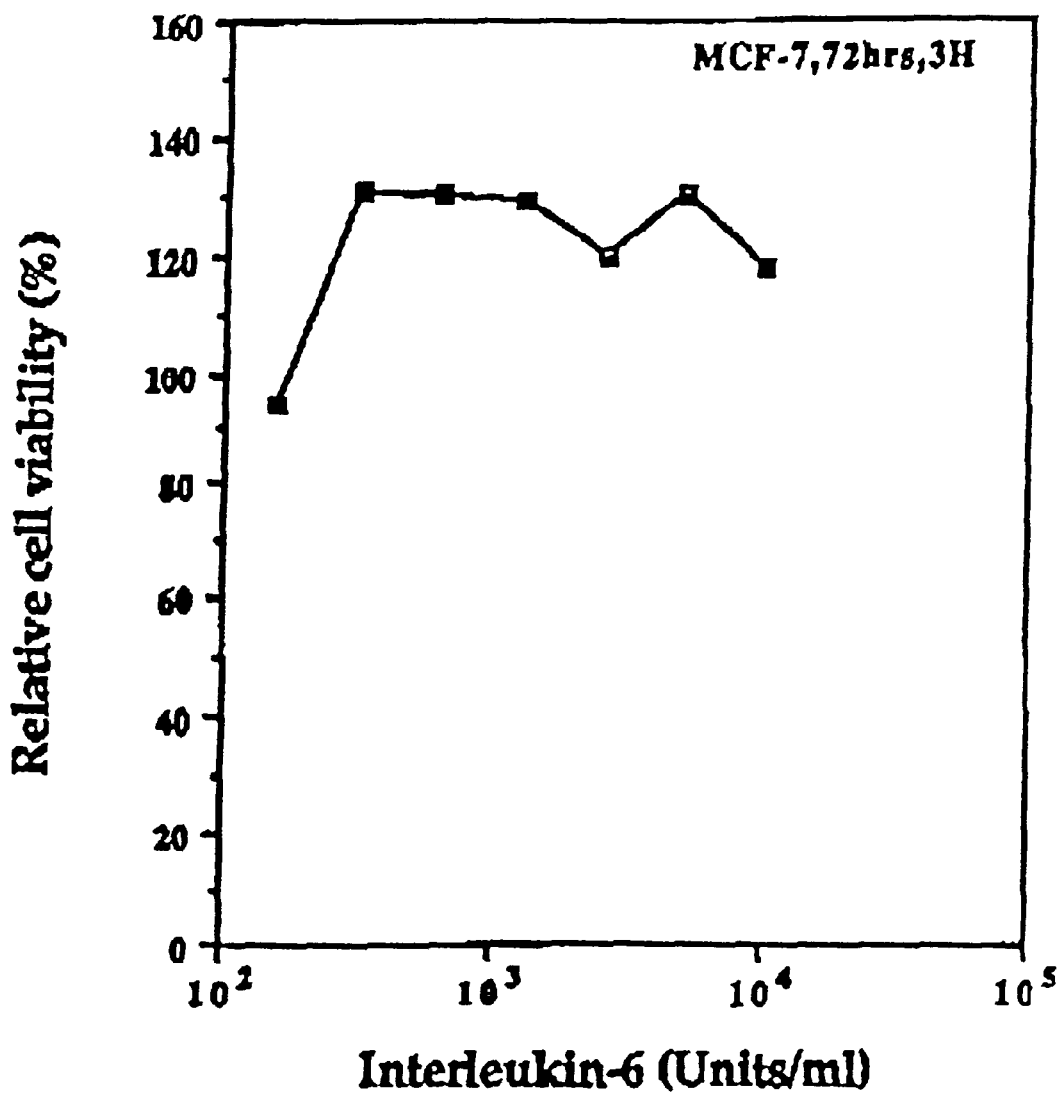

Interleukin-6 is cytokine produced by a wide variety of different cell types in response to highly diverse stimuli and has a molecular weight of 26 kDa on SDS-PAGE. Specifically, IL-6 is also produced by normal human fibroblasts, U-937, human melanoma cell lines A375, RPMI-7951 etc. IL-6 inhibits the growth of myeloid leukemia and breast carcinoma cell lines. Based on the source, method of induction and tumor cell target specificity, IL-6 appears to be a different cytokine from that of Oncoinhibin. Moreover, MCF-7 cells routinely used as a target for Oncoinhibin are insensitive to the effects of Interleukin-6 (FIG. 16). Also in contrast to Oncoinhibin, IL-6 was found to inhibit the growth of normal human fibroblasts (FIG. 15).

Figure 17:
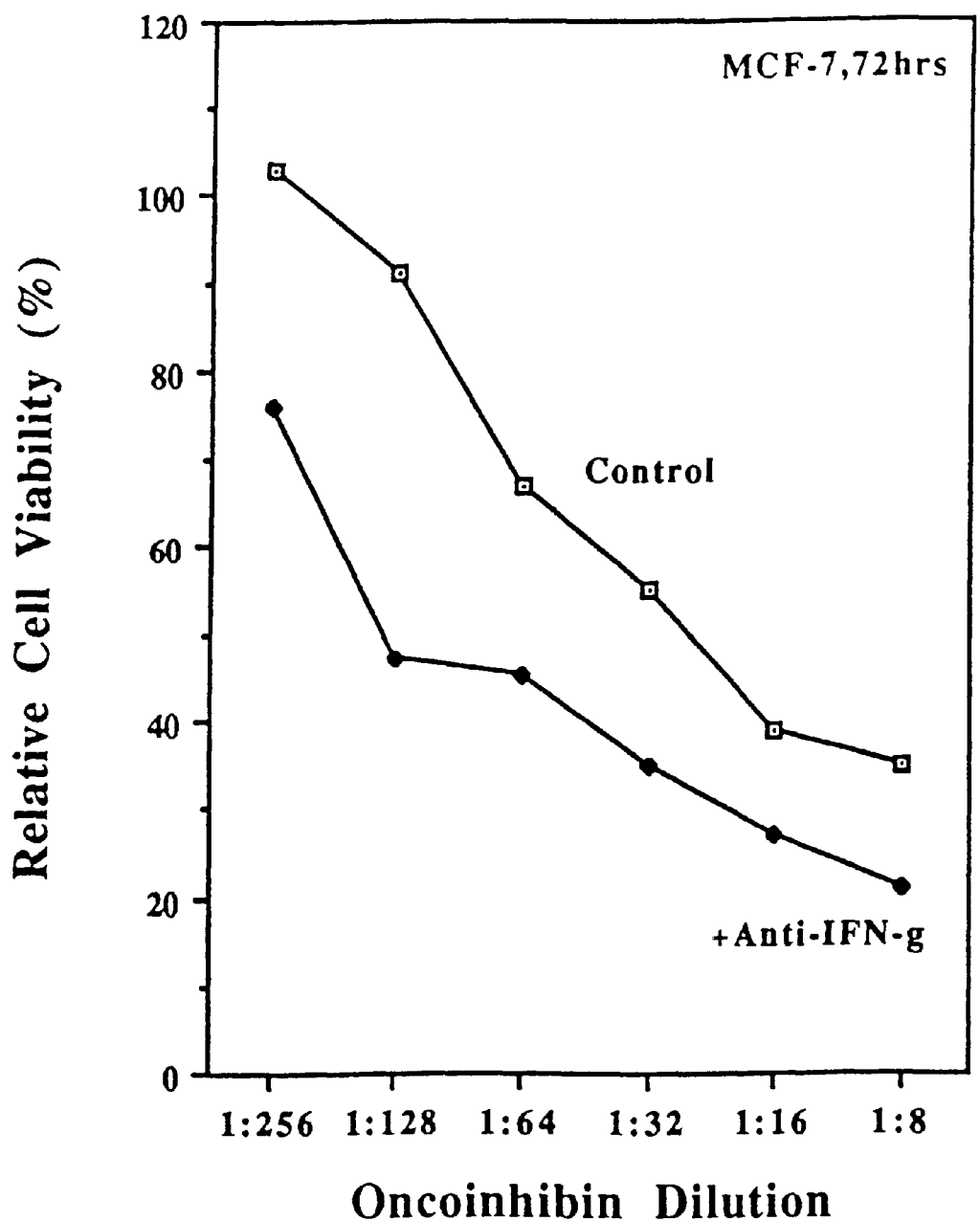
FIG. 17 depicts the effects of antibodies against interferon-γ on the Oncoinhibin activity on human breast tumor cells (MCF-7).
Figure 18A:
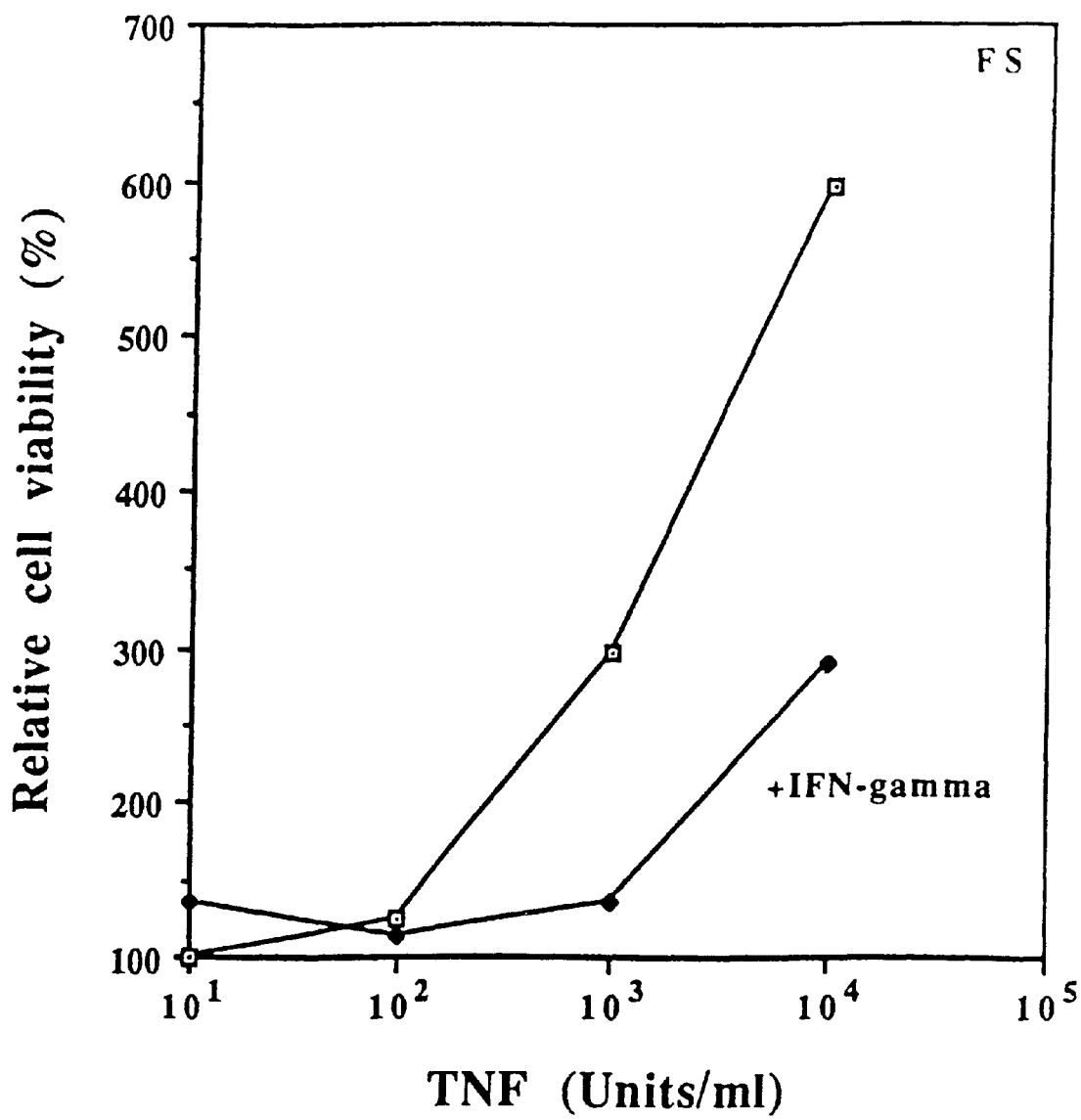
FIGS. 18A and 18B show the inhibitory effects of interferon-γ on TNF (upper panel) but not Oncoinhibin (lower panel) on human foreskin fibroblasts.
Figure 18B:
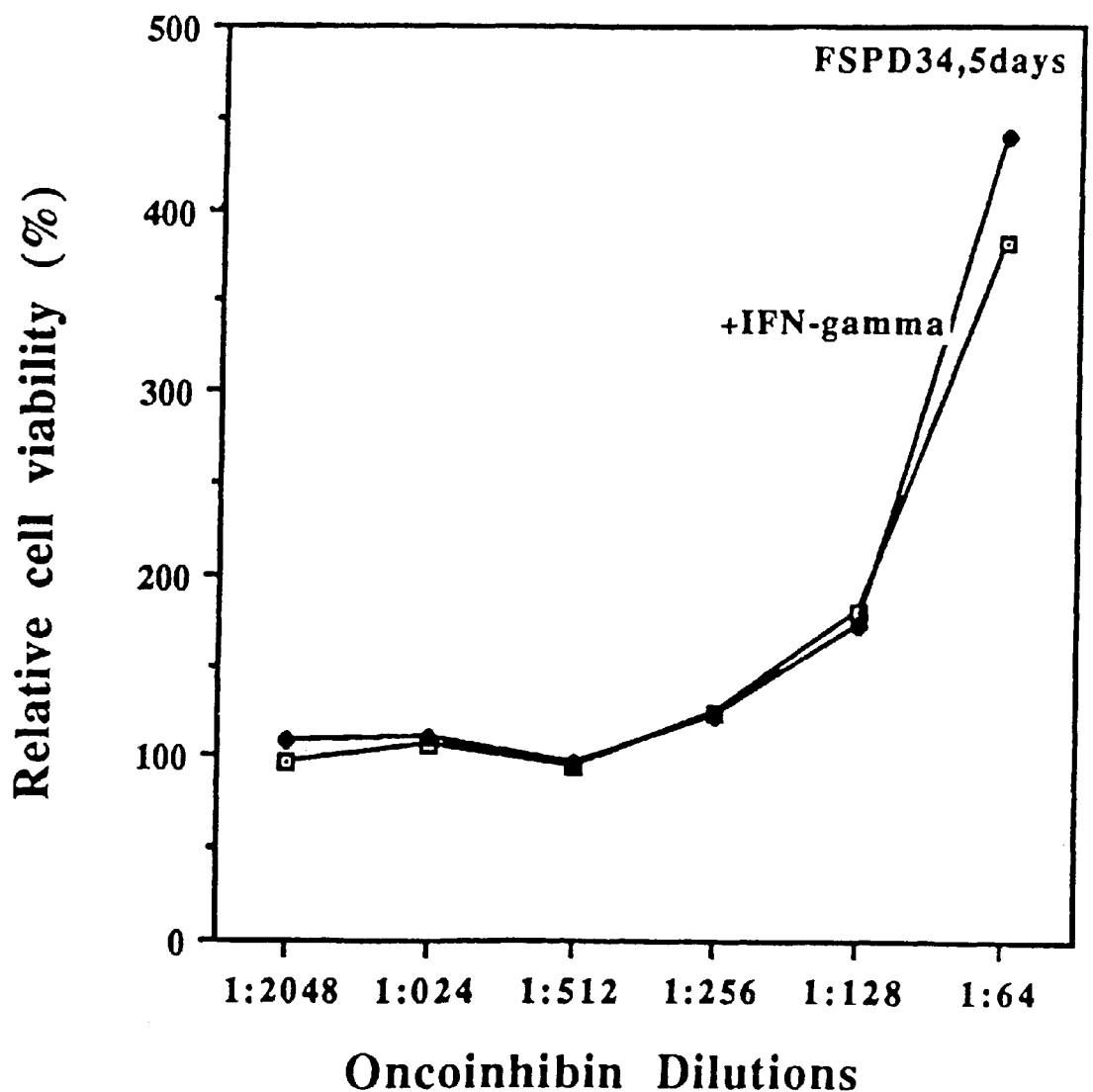

Interferon-$\gamma$ a cytokine with a molecular weight of 20–25 kDa on SDS-PAGE, is produced by T-lymphocytes when activated with various mitogens and inhibits the growth of certain tumor cell lines. This cytokine is highly sensitive to acidic pH conditions. Oncoinhibin differs from interferon-$\gamma$ with respect to its source, method of induction and pH stability. Interferon-$\gamma$ also differs from Oncoinhibin with respect to its effect on normal human fibroblasts. Oncoinhibin stimulates the proliferation whereas interferon-$\gamma$ inhibits the TNF-induced fibroblast proliferation but not produced by Oncoinhibin (FIG. 18). Moreover, antibodies to interferon-γ do not reduce the activity of Oncoinhibin but enhance it (FIG. 17).

Figure 22:
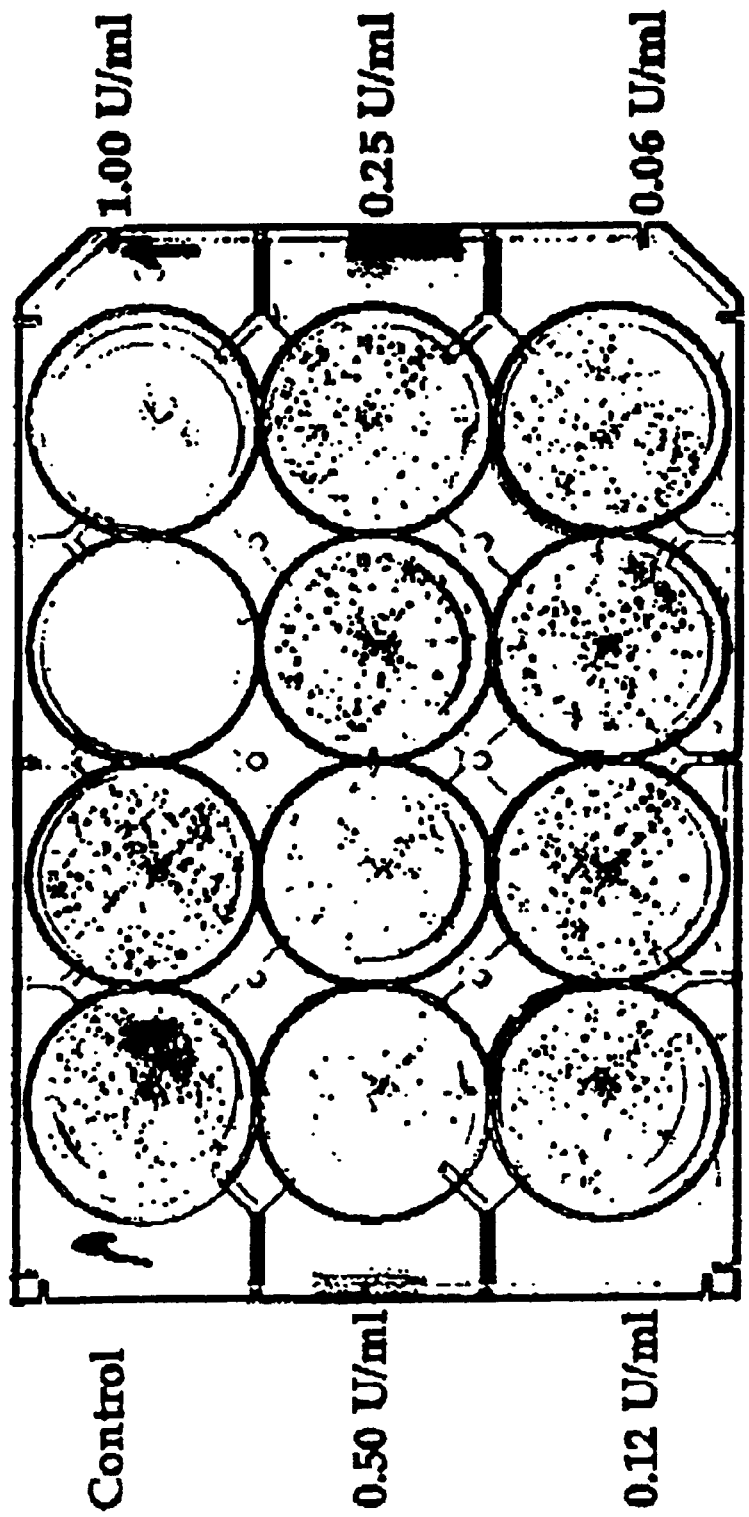
FIG. 22 shows that Oncoinhibin inhibits colony formation of tumor cells. MCF-7 cells (1000 cells/well) were plated into 12 well Falcon plates. After 24 hours, the medium was removed and serial dilutions of the Oncoinhibin were added. After 10 days, incubation at 37° C., medium was removed and colonies were visualized by crystal violet staining.

The present invention clearly illustrates that Oncoinhibin has antitumor properties. The present invention shows that Oncoinhibin inhibits the growth of tumor cells as determined by cell viability, thymidine incorporation and by the use of vital dye crystal violet. In addition, FIG. 22 shows that the formation of colonies by human breast tumor cells MCF-7 is also completely inhibited by Oncoinhibin in a dose-dependent manner.

Figure 23A:
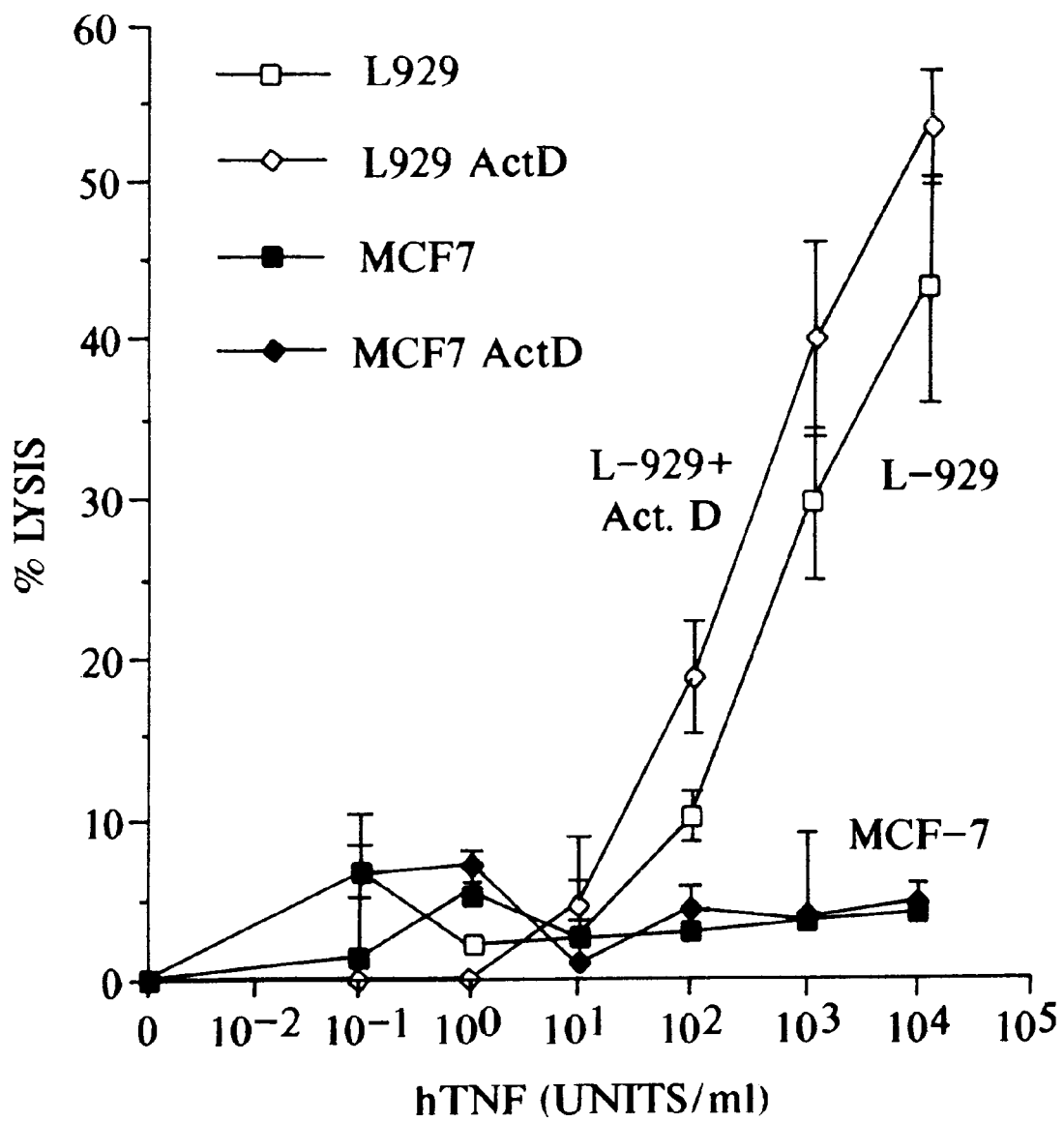
FIG. 23 shows that Oncoinhibin is cytostatic and not cytotoxic. MCF-7 and L-929 cells were incubated for 3 hours with and. without actinomycin D (1 $\mu$g/ml), then washed, trypsinized and labeled, with $^{51}$Cr for 45 minutes. Thereafter cells were washed three times and plated $2.5 \times 10^4$ cells in 96 well plates. After adherence for 2 hours, medium was changed to fresh media containing different concentrations of either tumor necrosis factor (upper panel) or Oncoinhibin (lower panel). After overnight incubation at 37° C., the release of $^{51}$Cr was determined in the supernatants.
Figure 23B:
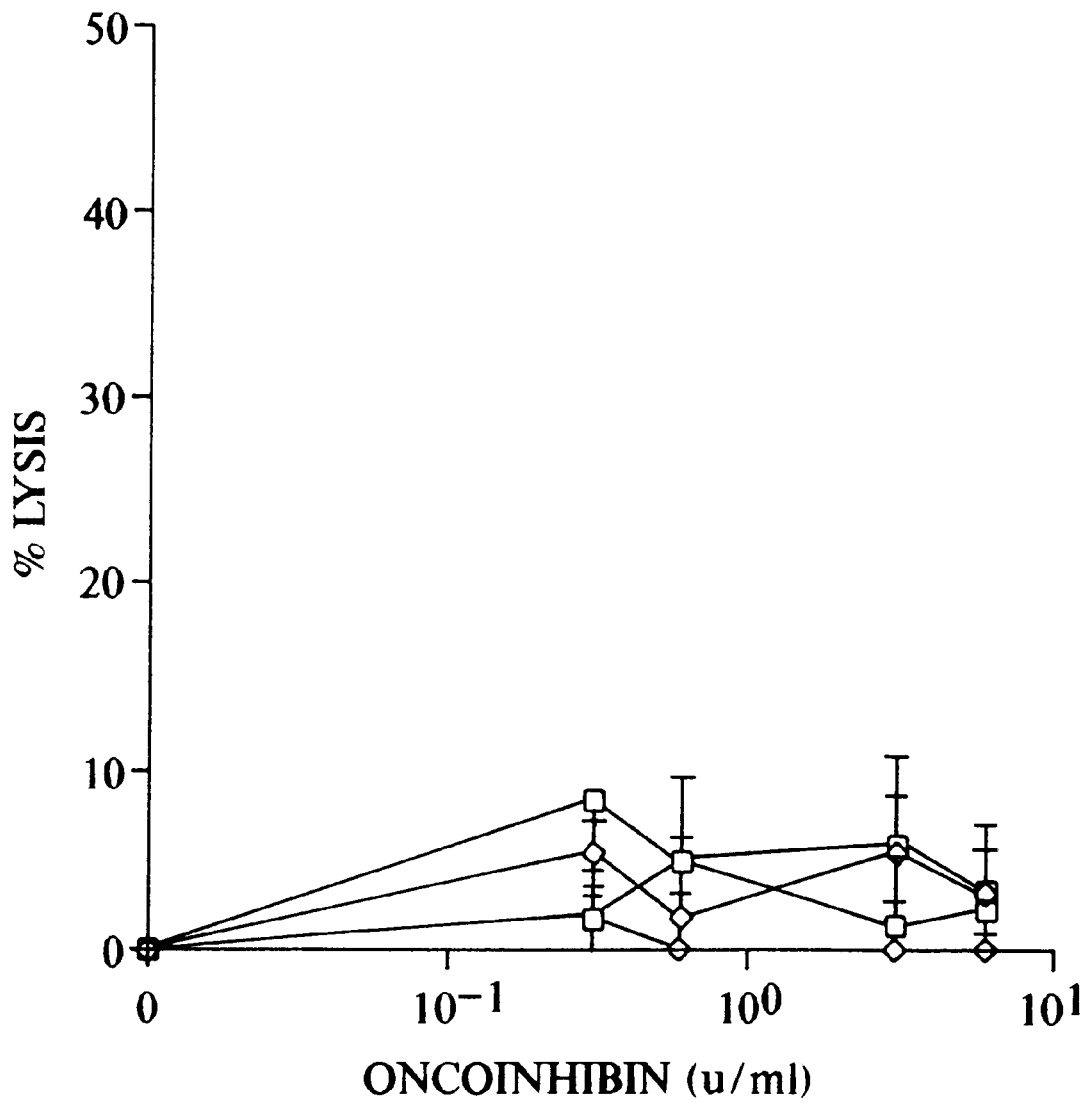

The present invention also illustrates that Oncoinhibin is cytostatic rather cytotoxic. That is, tumor cells can be inhibited by an agent either by being toxic to the cells or by inhibiting cell proliferation or both. Whether an agent is cytotoxic to cells is determined by its ability to induce release of chromium from chromium-prelabeled cells. When this was examined for Oncoinhibin on L-929 cells (FIG. 23), it was found that under the conditions that tumor necrosis factor caused the release of chromium, Oncoinhibin was ineffective. These results illustrate that Oncoinhibin is inhibitory to the cells by a cytostatic as opposed to a cytotoxic mechanism. These results also distinguish Oncoinhibin from tumor necrosis factor.

Figure 24:
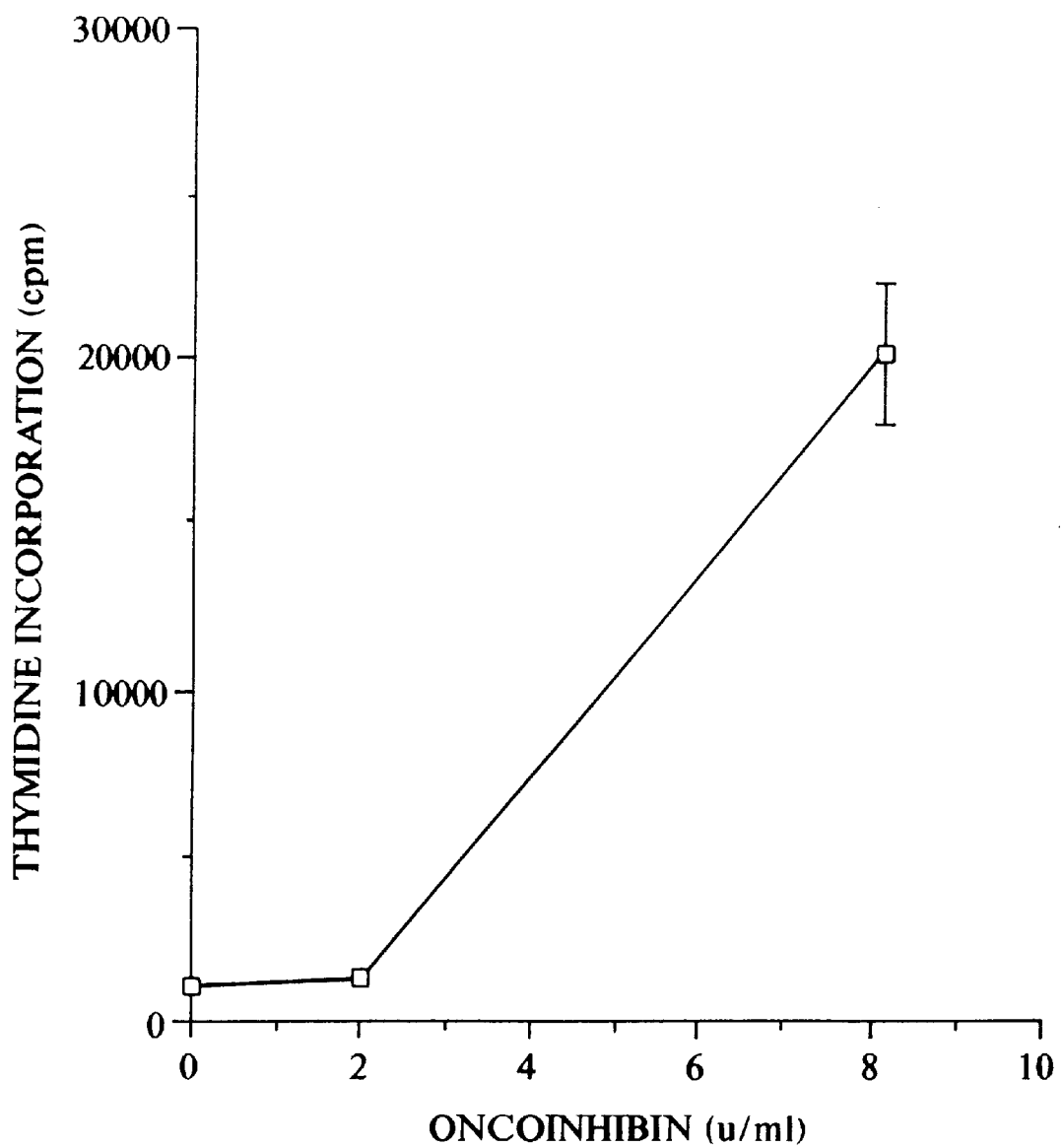
FIG. 24 shows that Oncoinhibin stimulates the proliferation of peripheral blood lymphocytes. Peripheral blood lymphocytes freshly isolated from normal human subjects were plated at $10^5$ cells in 0.2 ml of complete RPNI 1640 medium. Cells were incubated with different concentrations of Oncoinhibin for 72 hours at 37° C. and pulsed with $^3$H thymidine (0.5 $\mu$Ci/well) during last 8 hours.

The present invention also demonstrates that Oncoinhibin displays immunomodulatory activities. To further illustrate Oncoinhibin's immunomodulatory activity, its effect was first examined on the proliferation of peripheral blood lymphocytes (PBL). As shown in FIG. 24, Oncoinhibin was found to induce proliferation of peripheral blood lymphocytes. In this respect, Oncoinhibin's effects are similar to interleukin-2 (IL-2).

Figure 25A:
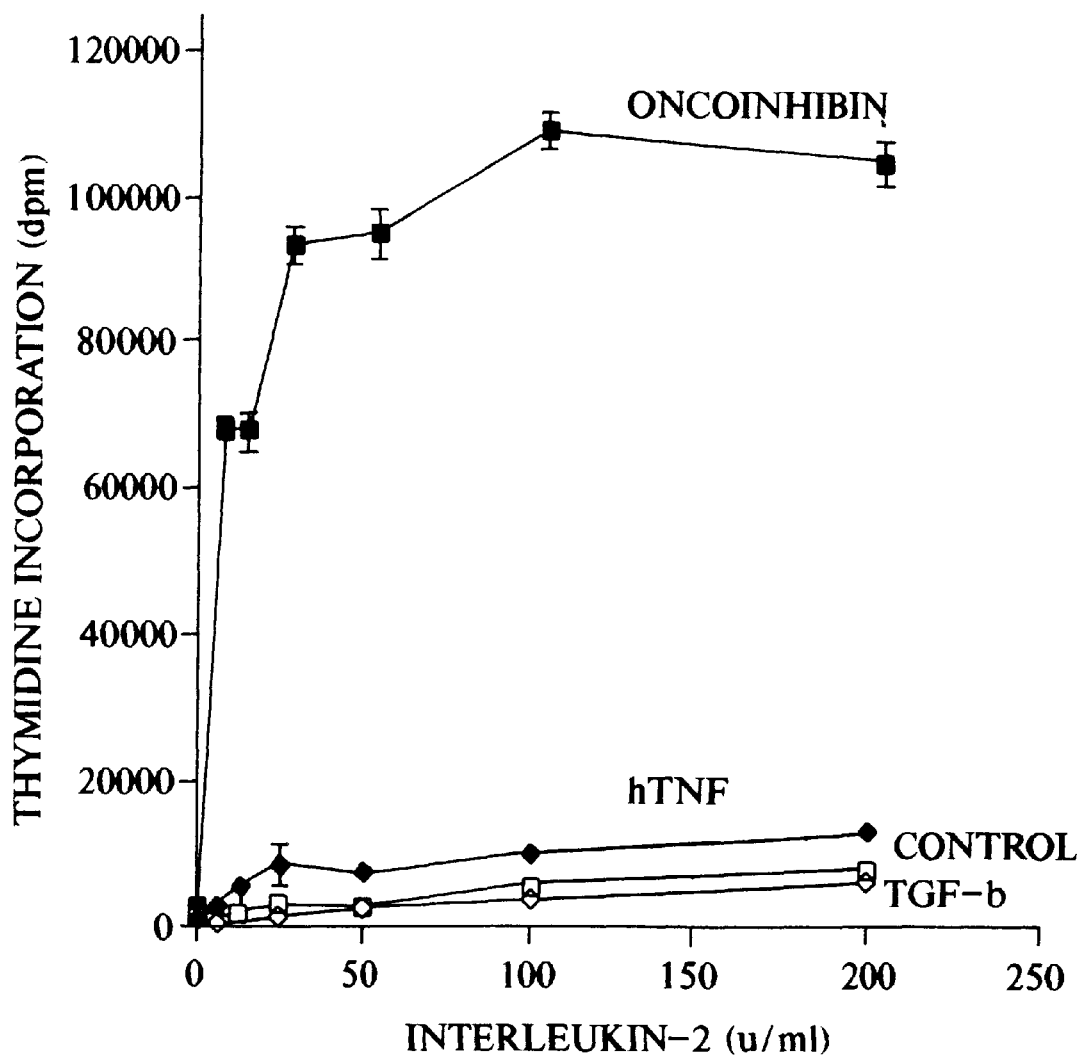
FIG. 25 shows that Oncoinhibin synergizes with specific (IL-2; upper panel) and nonspecific (Con A; lower panel) mitogens for proliferation of peripheral blood lymphocytes. Peripheral blood lymphocytes freshly isolated from normal human subjects were plated at $10^5$ cells in 0.2 ml of complete RPMI 1640 medium. Cells were incubated with different concentrations of either IL-2 or Con A with or without Oncoinhibin, tumor necrosis factor or Transforming Growth Factor-$\beta$ (TGF-$\beta$) for 72 hours at 37° C. and pulsed with $^3$H thymidine (0.5 $\mu$Ci/well) during last 18 hours.
Figure 25B:
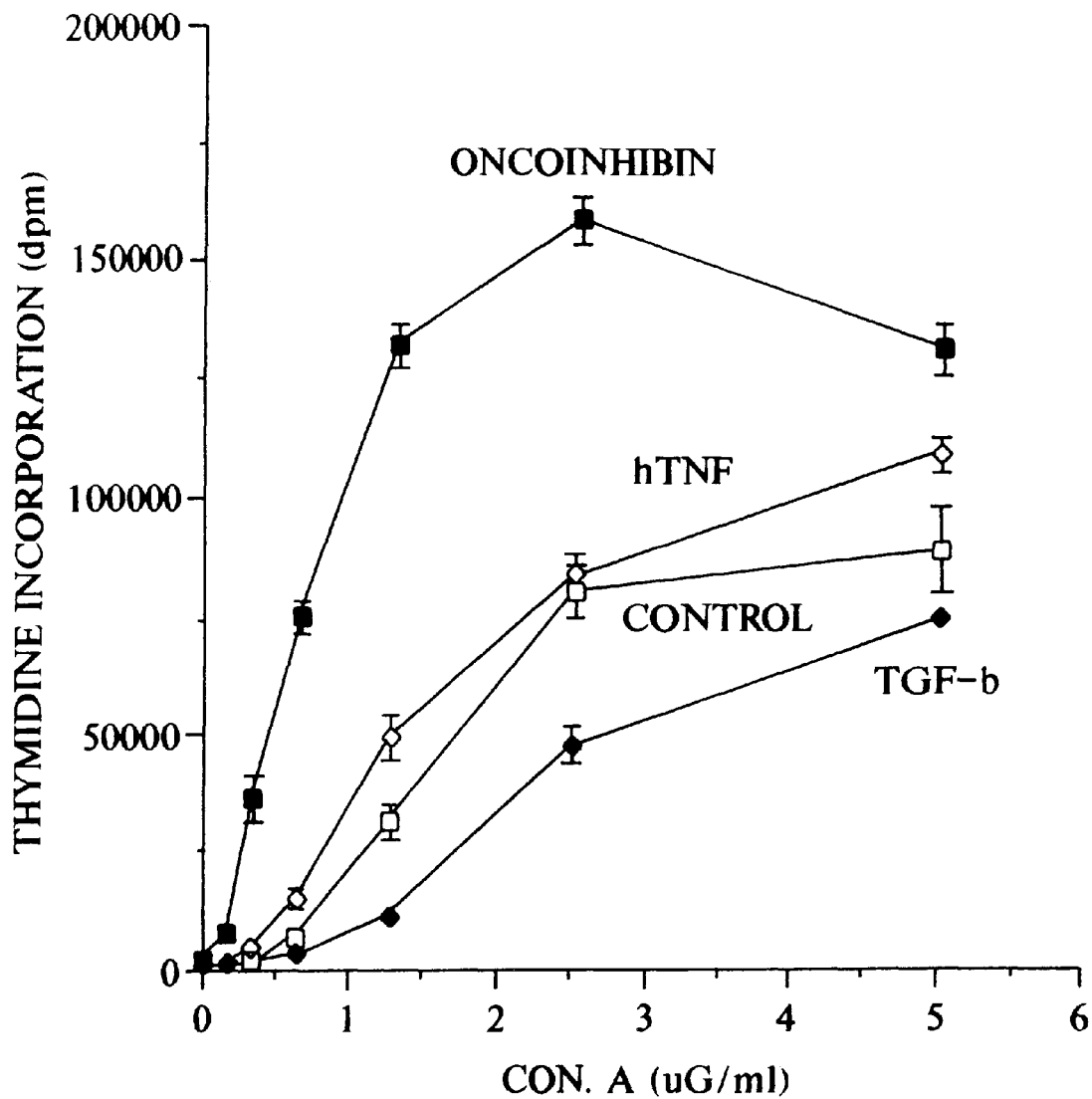
Figure 26:
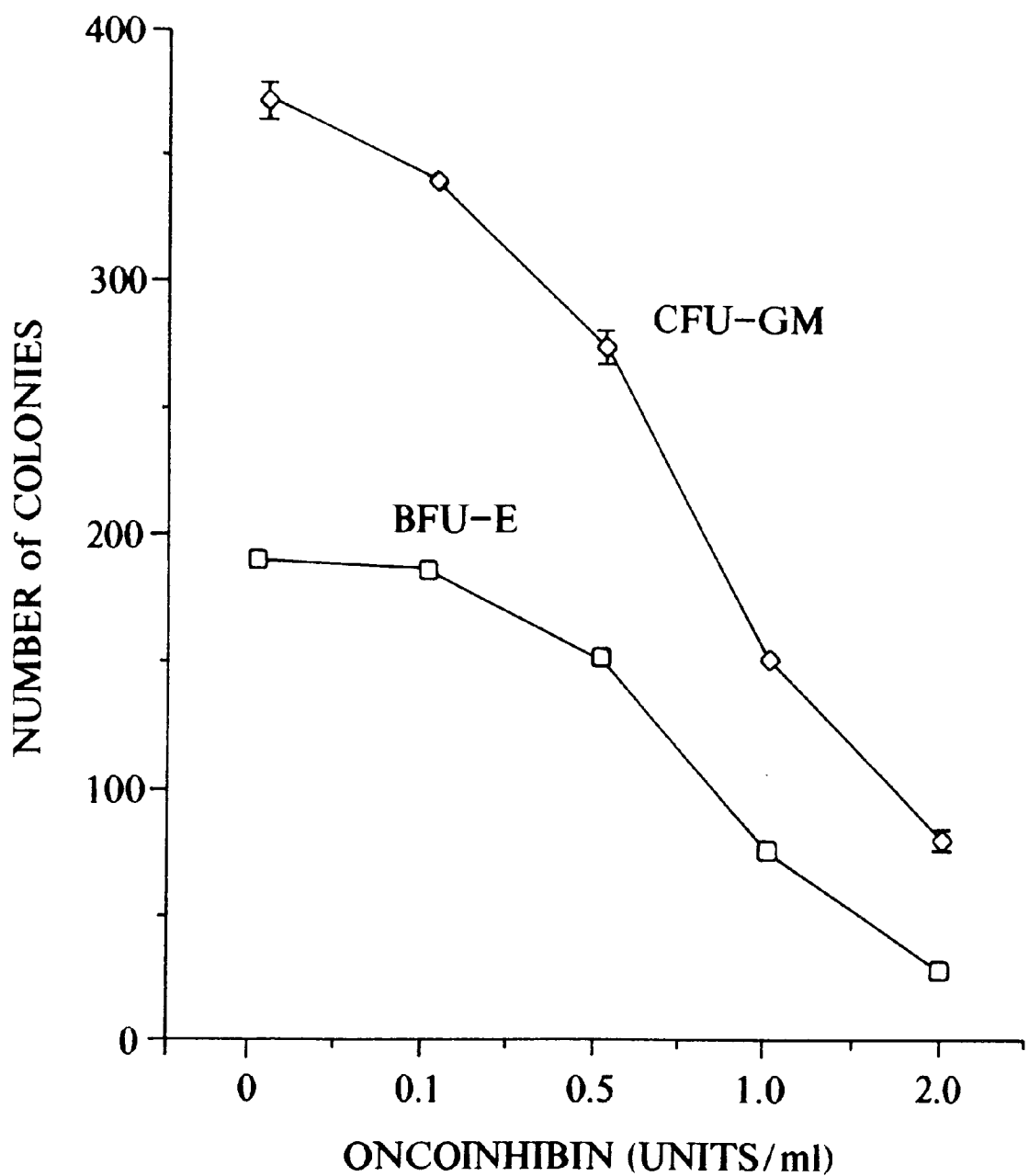
FIG. 26 shows that Oncoinhibin inhibits CFU-GM and BFU-E formation.

Oncoinhibin's ability to synergize with specific (IL-2) and nonspecific (Con A) mitogens for proliferation of peripheral blood lymphocytes was also examined. As shown in FIG. 25, both IL-2 and ConA were found to potentiate the effect of Oncoinhibin in a dosedependent manner. Oncoinhibin affects the proliferation of other blood cell types. As shown in FIG. 26, Oncoinhibin inhibited the formation of CFU-GM and BFU-E colonies.

Figure 27:
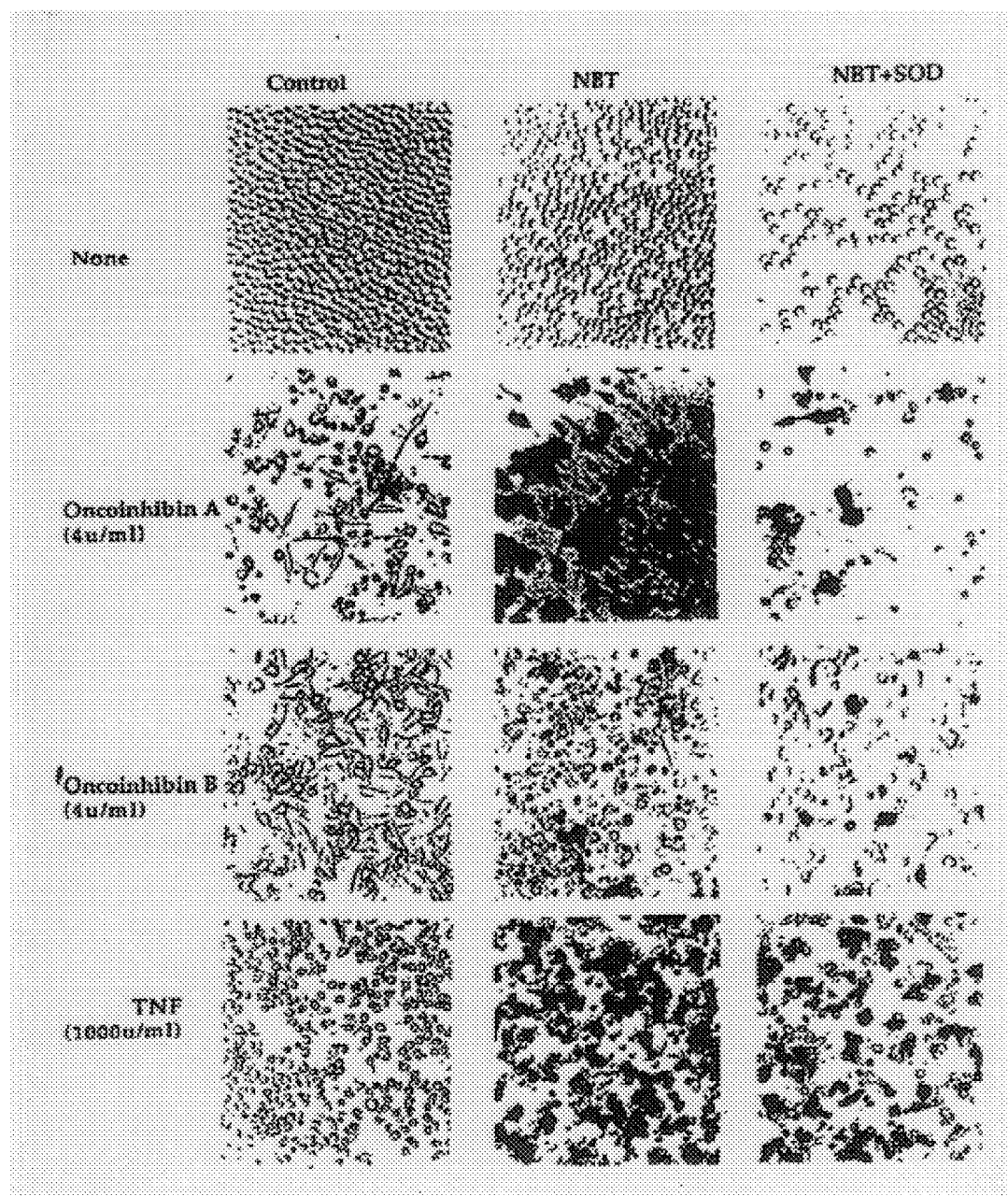
FIG. 27 shows that Oncoinhibin induces differentiation of myeloid cells. ML-la cells were plated into 96 well plates and then treated with either media, or Oncoinhibin A (uninduced) or Oncoinhibin B (PMA-induced) or tumor necrosis factor for 72 hours. Thereafter, where indicated 0.1% nitrotetrazolium blue (NBT) or 1200 units/ml of superoxide dismutase (SOD) were added to the wells. After 60 minutes, cells photographed to demonstrate the morphological changes.

Oncoinhibin ability to induce differentiation of myeloid cells was also examined. FIG. 27 indicates that Oncoinhibin induced the differentiation of human myeloid cell line, ML-la. Oncoinhibin preparation prepared without phorbol ester induction (sample B) was as effective as that with phorbol ester (sample A). Thus, this effect of Oncoinhibin is not due to phorbol ester, a known inducer of myeloid differentiation. Taken together, the present invention indicates that Oncoinhibin has strong immuno-modulatory activity and that this activity may also contribute to the in vivo antitumor effects of Oncoinhibin.

Figure 28A:
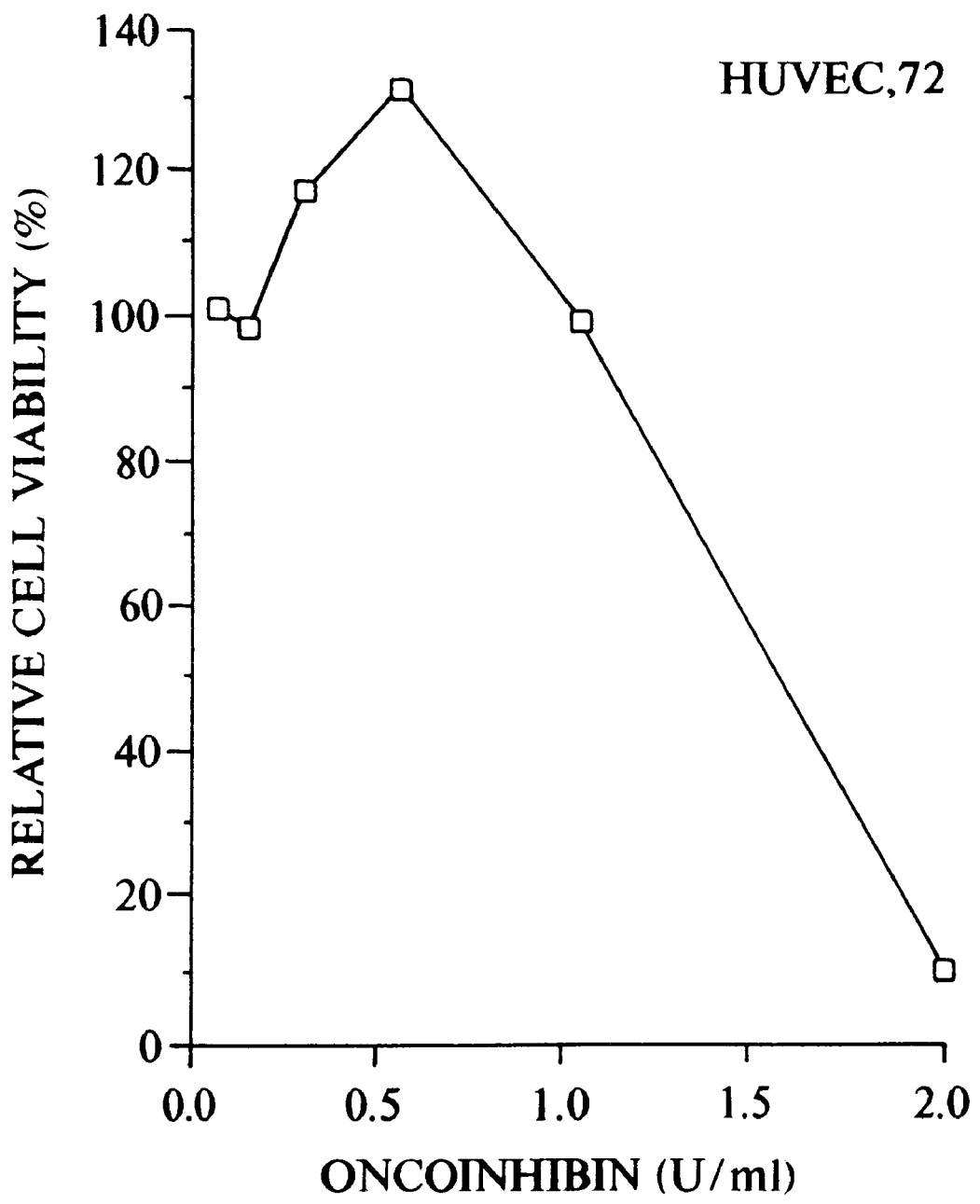
FIG. 28 shows that Oncoinhibin inhibits the growth of endothelial cells. Human endothelial (upper panel) and bovine endothelial (lower panel) cells (5000 cells/well) in 0.1 ml media were plated in 96-well plates. The next day, the media was removed and serial dilutions of Oncoinhibin were added to each well and incubated at 37° C. for 72 hours. During last 24 hours, $^3$H thymidine (0–5 $\mu$Ci/well) was added, cells were then trysinized, harvested and counted for thymidine incorporation by 9600 matrix beta counter.
Figure 28B:
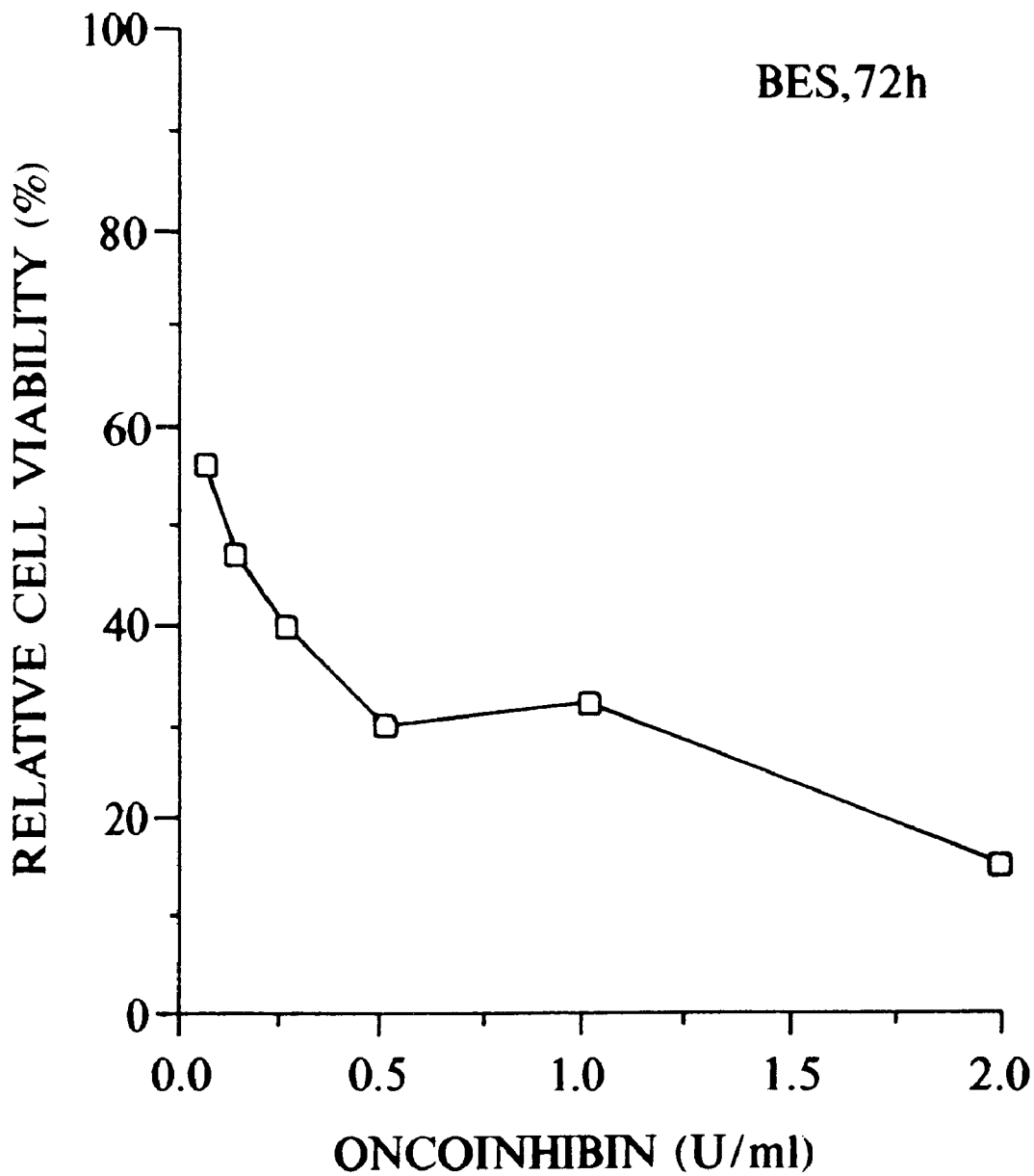

The present invention also demonstrates that Oncoinhibin displays anti-angiogenic property. To illustrate the anti-angiogenic effects of Oncoinhibin, its ability to inhibit the growth of human and bovine vascular endothelial cells was examined. As shown in FIG. 28, Oncoinhibin inhibited the proliferation of both type of endothelial cells in a dose-dependent manner. Since proliferation of endothelial cells leading to blood vessel formation in solid tumors is critical for the growth of the tumor, this may also contribute to the antitumor actions of Oncoinhibin.

Thus, the present invention provides a novel cytokine exhibiting diverse antineoplastic activity. The cytokine, Oncoinhibin, is secreted by human erythroblastoid cells and has a molecular weight of approximately 28 kDa on SDS-PAGE. Production of Oncoinhibin appears to be enhanced in the presence of phorbol ester. Oncoinhibin appears to be stable to a wide range of substances and stable in a wide pH range and to a high temperature.

Due to its diverse neoplastic activity, it is contemplated that Oncoinhibin will be of therapeutic use in the treatment of a wide variety of neoplastic diseases, including carcinomas and lymphomas. Oncoinhibin may be supplied to humans or other animals as part of a pharmaceutical composition that would contain a pharmaceutically acceptable carrier. Due to its diverse antineoplastic activity, Oncoinhibin will be useful in preventing recurrence of neoplastic diseases. In addition, administration of Oncoinhibin to hosts having a neoplastic cells will likely extend the survival time of the host. Alternatively, neoplastic cells could be treated with Oncoinhibin in vitro, e.g., the treatment and purging of bone marrow containing neoplastic cells. These methods of treating neoplastic cells as described herein are well known in the art of cancer chemotherapy and consequently a person having ordinary skill in this art could, without undue experimentation, determine the appropriate dosages and routes of administration of Oncoinhibin.

Oncoinhibin may also be useful as a novel immunomodulator. Oncoinhibin activates lymphocytes, monocytes and neutrophils to kill tumor cells. In addition, Oncoinhibin may be therapeutically useful as a growth factor. Oncoinhibin stimulates the growth of normal cells.

In conclusion, it is seen that the present invention and the embodiments disclosed herein are well adapted to carry out the objectives and obtain the end set forth in this application. Certain changes can be made in the method and apparatus without parting from the spirit and scope of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

What is claimed is:

1. A method of treating a disease in an individual in need of such treatment, comprising the step of administering a pharmaceutical composition comprising a pharmacologically effective dose of a human Oncoinhibin protein and a pharmaceutically acceptable carrier, said disease selected from the group consisting of carcinoma and a lymphoma.

2. The method of claim 1, said carcinoma selected from the group consisting of breast carcinomas, melanomas, cervical carcinomas, ovarian carcinomas, and hepatomas.

3. A method of treating a neoplastic cell comprising administering a pharmacologically effective dose of a pharmaceutical composition comprising a human Oncoinhibin protein and a pharmaceutically acceptable carrier to said cell.

4. The method of claim 3, wherein said neoplastic cell is selected from the group consisting of lymphomas, breast carcinomas, melanomas, cervical carcinomas, ovarian carcinomas, and hepatomas.

5. The method of claim 3, wherein said neoplastic cell occurs in a human or animal.

6. The method of treating of claim 3, wherein said composition contacts said neoplastic cell in vitro.

* * * * *

UNITED STATES PATENT AND TRADEMARK OFFICE
CERTIFICATE OF CORRECTION

PATENT NO.   : 5,993,798  
DATED        : November 30, 1999  
INVENTOR(S)  : Bharat B. Aggarwal Page 1 of 2

It is certified that error appears in the above-identified patent and that said Letters Patent is hereby corrected as shown below:

Column 1:
Line 64, "is' should read --are--.

Column 2:
Line 24, please delete the period at the end of the line and replace it with a colon.
Line 25 "illustrates" should read --Illustrate--.

Column 3:
Line 15, please delete the period after the word "and"
Line 49, please insert the word --were-- between the words "cells" and "photographed".

Column 6:
Line 67, "was" should read --were--.

Column 7:
Line 1, "(1 cmx5 cm)" should read --(cm x 5 cm)--.

UNITED STATES PATENT AND TRADEMARK OFFICE
CERTIFICATE OF CORRECTION

PATENT NO. : 5,993,798
DATED : November 30, 1999
INVENTOR(S) : Bharat B. Aggarwal It is certified that error appears in the above-identified patent and that said Letters Patent is hereby corrected as shown below:

Column 8:
Line 38, "days" should read --days'--.
Line 48, "phosphatebuffered" should read --phosphate-buffered--.

Column 13:
Line 46, "Asepharose" should read --A-sepharose-.

Column 16:
Line 34, please delete the word "the".

Signed and Sealed this

Nineteenth Day of June, 2001

Attest:

NICHOLAS P. GODICI
Attesting Officer  Acting Director of the United States Patent and Trademark Office